United States Patent [19]
Elhammer et al.

[11] Patent Number: 6,096,512
[45] Date of Patent: Aug. 1, 2000

[54] CLONED DNA ENCODING A UDP-GALNAC: POLYPEPTIDE, N-ACETYLGALACTOSAMINYLTRANSFERASE

[75] Inventors: Ake P. Elhammer; Fred L. Homa, both of Kalamazoo, Mich.

[73] Assignee: Pharmacia & Upjohn Company, Kalamazoo, Mich.

[21] Appl. No.: 08/967,506

[22] Filed: Nov. 11, 1997

Related U.S. Application Data

[60] Division of application No. 08/602,830, filed as application No. PCT/US94/02552, Mar. 17, 1994, abandoned, which is a continuation-in-part of application No. 08/063,186, May 14, 1993, abandoned.

[51] Int. Cl.[7] ............................. C12N 15/54; C12P 21/00
[52] U.S. Cl. ...................... 435/68.1; 435/70.1; 435/71.1; 435/71.2; 435/72; 435/74; 435/97; 435/440; 435/455; 435/471; 435/476
[58] Field of Search ................................. 435/68.1, 70.1, 435/71.1, 71.2, 72, 74, 97, 440, 455, 471, 476; 536/23.2

[56] References Cited

U.S. PATENT DOCUMENTS

| | | | |
|---|---|---|---|
| 4,521,592 | 6/1985 | Dahmén et al. | 536/4.1 |
| 4,657,849 | 4/1987 | Kallenius et al. | 435/7 |
| 4,665,060 | 5/1987 | Mardh et al. | 514/61 |
| 4,762,824 | 8/1988 | Kallenius et al. | 514/54 |
| 4,801,583 | 1/1989 | Petitou et al. | 514/54 |
| 4,810,784 | 3/1989 | Larm | 536/20 |
| 4,851,338 | 7/1989 | Mardh et al. | 435/34 |
| 5,047,335 | 9/1991 | Paulson et al. | 435/69.1 |
| 5,324,663 | 6/1994 | Lowe | 435/320.1 |

FOREIGN PATENT DOCUMENTS

| | | |
|---|---|---|
| WO 91/03484 | 3/1991 | WIPO . |
| WO 91/06635 | 5/1991 | WIPO . |
| WO 91/12340 | 8/1991 | WIPO . |

OTHER PUBLICATIONS

Aubert, J.–P., Biserte, G. and M–H Loucheux–Lefebvre, "Carbohydrate–Peptide Linkage in Glycoproteins," *Arch. Biochem. Biophys.,* 175:410–418 (1976).

Bourdon, M.A., Krusius, T., Campbell, S., Schwartz, N.B., and E. Ruoslahti, "Identification and synthesis of a recognition signal for the attachment of glycosaminoglycans to proteins," *Proc. Natl. Acad. Sci. USA,* 84:3194–3198 (1987).

Briand, J.P., Andrews, S.P., Jr., Cahill, E., Conway, N.A., and J.D. Young, "Investigation of the Requirements for O–Glycosylation by Bovine Submaxillary Gland UDP–N–Acetylgalactosamine: Polypeptide N–Acetylgalactosamine Transferase Using Synthetic Peptide Substrates," *J. Biol. Chem.,* 256(23):12205–12207 (1981).

Bushway, A. A., and T. W. Keenan, "Characterization of a Soluble Glycolipid Galactosyltransferase Which Occurs in Bovine Milk," *Biochim. Biophys. Acta,* 572:146–152 (1979).

Carlson, D.M., "Structures and Immunochemical Properties of Oligosaccharides Isolated from Pig Submaxillary Mucins," *J. Biol. Chem.,* 243(3):616–626 (1968).

Chen, W., and O. P. Bahl, "Recombinant Carbohydrate Variant of Human Choriogonadotropin β–Subunit (hCGβ) Descarboxyl Terminus (115–145)," *J. Biol. Chem.,* 266(10):6246–6251 (1991).

Chou, P.Y., and G.D. Fasman, "Empirical Predictions of Protein Conformation," *Ann. Rev. Biochem.,* 47:251–276 (1978).

Cruz, T.F., and M.A. Moscarello, "Identification of the Major Sites of Enzymic Glycosylation of Myelin Basic Protein," *Biochim. Biophys. Acta,* 760:403–410 (1983).

Davis, C. G., Elhammer, A., Russell, D.W., Schneider, W.J., Kornfeld, S., Brown, M.S., and J.L. Goldstein, "Deletion of Clustered O–Linked Carbohydrates Does Not Impair Function of Low Density Lipoprotein Receptor in Transfected Fibroblasts," *J. Biol. Chem.,* 261(6):2828–2838 (1986).

Deschuyteneer, M., Eckhardt, A.E., Roth, J. and R.L. Hill, "The Subcellular Localization of Apomucin and Nonreducing Terminal N–Acetylgalactosamine in Porcine Submaxillary Glands," *J. Biol. Chem.,* 263(5):2452–2459 (1988).

Devereux, J., Haeberli, P. and O. Smithies, "A comprehensive set of sequence analysis programs for the VAX," *Nucleic Acids Res.,* 12(1):387–395 (1984).

Domingo, D. L., and I. S. Trowbridge, "Characterization of the Human Transferrin Receptor Produced in a Baculovirus Expression System," *J. Biol. Chem.,* 263(26):13386–13392 (1988).

Dunphy, W. G., Brands, R., and J.E. Rothman, "Attachment of Terminal N–Acetylglucosamine to Asparagine–Linked Oligosaccharides Occurs in Central Cisternae of the Golgi Stack," *Cell,* 40:463–472 (1985).

Eisenberg, D., "Three–Dimensional Structure of Membrane and Surface Proteins," *Ann. Rev. Biochem.,* 53:595–623 (1984).

Elhammer, A.P. et al., "The Specificity of UDP–GalNAc: Polypeptide N–Acetylgalactosaminyltransferase as Inferred from a Database of in Vivo Substrates and from the in Vitro Glycosylation of Proteins and Peptides," *J. of Biological Chemistry,* 268(14):10029–10038 (1993).

Elhammer, A. P. & S. Kornfeld,"Purification and Characterization of UDP–N–Acetylgalactosamine: Polypeptide N–Acetylgalactosaminyltransferase from Bovine Colostrum and Murine Lymphoma BW5147 Cells," *J. of Biological Chemistry,* 261(12):5249–5255 (1986).

(List continued on next page.)

*Primary Examiner*—Rebecca E. Prouty
*Attorney, Agent, or Firm*—Thomas A. Wootton; James D. Darnley, Jr.

[57] ABSTRACT

The present invention relates to a method for the isolation and expression of a glycosyltransferase enzyme for use in the synthesis of oligosaccharide or polysaccharide structures on glycoproteins, glycolipids, or as free molecules. The gene coding for the enzyme N-acetylgalactosaminyltransferase and the polypeptide sequence of the acceptor peptide for the enzyme N-acetylgalactosaminyltransferase have been isolated and used for the control of glycosylation of a protein.

11 Claims, 15 Drawing Sheets-

OTHER PUBLICATIONS

Elhammer, A.P., and S. Kornfeld, "Two Enzymes Involved in the Synthesis of O–linked Oligosaccharides are Localized on Membranes of Different Densities in Mouse Lymphoma BW5147 Cells," *J. Cell Biol.*, 98:327–331 (1984).

Fraser, M.J., The Baculovirus–Infected Insect Cell as a Eukaryotic Gene Expression System, *Current Topics Microbiol. Immunol.*, 158:131–172 (1992).

Garnier, J., Osguthorpe, D.J., and B. Robson, "Analysis of the Accuracy and Implications of Simple Methods for Predicting the Secondary Structure of Globular Proteins," *J. Mol. Biol.*, 120:97–120 (1978).

Goldin, A. L., Sandri–Goldin, R.M., Levine, M., and J.C. Glorioso, "Cloning of Herpes Simplex Virus Type 1 Sequences Representing the Whole Genome," *J. Virol.*, 38(1):50–58 (1981).

Gooley, A.A., Classon, B.J., Marschalek, R., and K.L. Williams, "Glycosylation Sites Identified by Detection of Glycosylated Amino Acids Released From Edman Degradation: The Identification of Xaa–Pro–Xaa–Xaa as a Motif for Thr–O–Glycosylation," *Biochem. Biophys. Res. Commun.*, 178(3):1194–1201 (1991).

Hagopian, A., and E.H. Eylar, "Glycoprotein Biosynthesis: Studies on the Receptor Specificity of the Polypeptidyl: N–Acetylgalactosaminyl Transferase from Bovine Submaxillary Glands," *Arch. Biochem. Biophys.*, 128:422–433 (1968).

Hagopian, A., Westall, F.C., Whitehead, J.S., and E.H. Eylar, "Glycosylation of the A1 Protein from Myelin by a Polypeptide N–Acetylgalactosaminyltransferase," *J. Biol. Chem.*, 246(8): 2519–2523 (1971).

Haltiwanger, R.S., Holt, G.D. and G.W. Hart, "Enzymatic Addition of O–GlcNAc to Nuclear and Cytoplasmic Proteins," *J. Biol. Chem.*, 265(5):2563–2568 (1990).

Hanover, J.A., Elting, J., Mintz, G.R. and W.J. Lennarz, *J. Biol. Chem.*, 257(17):10172–10177 (1982).

Hardy, M.R., Townsend, R.R. and Y.C. Lee, "Monosaccharide Analysis of Glycoconjugates by Anion Exchange Chromatography with Pulsed Amperometric Detection," *Anal. Biochem.*, 170:54–62 (1988).

Hart, G.W., Holt, G.D. and R.S. Haltiwanger, "Nuclear and cytoplasmic glycosylation: novel saccharide linkages in unexpected places," *TIBS*, 13:380–384 (1988).

Heinrikson, R.L., Sterner, R. and C. Noyes, "On the Subunit Structure of Yeast Inorganic Pyrophosphatase," *J. Biol. Chem.*, 248(7):2521–2528 (1973).

Hill, Jr., H.D., Schwyzer, M., Steinman, H.M. and R.L. Hill, "Ovine Submaxillary Mucin," *J.Biol. Chem.*, 252(11):3799–3804 (1977).

Homa, F.L. et al., "Isolation and Expression of a cDNA Clone Encoding a Bovine UDP–GalNAc: Polypeptide N–Acetylgalactosaminyltransferase," *J. of Biological Chemistry*, 268(17):12609–12616 (1993).

Database Embl.—Homa, F.L. et al., "Isolation and expression of cDNA clone encoding a bovine UDP–GalNAc: polypeptide, N–acetylgalactosaminyltransferase," AN:L07780, May 7, 1993.

Homa, F. L., Otal, T.M., Glorioso, J.C. and M. Levine, "Transcriptional Control Signals of a Herpes Simplex Virus Type 1 Late (λ2) Gene Lie within Bases −34 to +124 Relative to 5' Terminus of the mRNA," *Mol. Cell. Biol.*, 6(11):3652–3666 (1986).

Hsieh, P., and P. W. Robbins, "Regulation of Asparagine–linked Oligosaccharide Processing," *J. Biol. Chem.*, 259(4):2375–2382 (1984).

Hughes, R.C., Bradbury, A.F. and D.G. Smyth, "Substrate Recognition by UDP–N–Acetyl–α–D–Galactosamine: Polypeptide N–Acetyl–α–D–Galactosaminyltransferase. Effects of Chain Length and Disulphide Bonding of Synthetic Peptide Substrates," *Carbohydr. Res.*, 178:259–269 (1988).

Jensenius, J.–C., Andersen, I., Hau, J., Crone, M. and C. Koch, "Eggs: Conveniently Packaged Antibodies. Methods for Purification of Yolk IgG," *J. Immunol. Meth.*, 46:63–68 (1981).

Jentoft, N., "Why are proteins O–glycosylated?" *Trends Biochem. Sci.*, 15:291–294 (1990).

Joziasse, D. H., "Mammalian glycosyltransferases: genomic organization and protein structure," *Glycobiology*, 2:271–277 (1992).

Kabsch, W., and C. Sander, "Dictionary of Protein Secondary Structure: Pattern Recognition of Hydrogen–Bonded and Geometrical Features," *Biopolymers*, 22:2577–2637 (1983).

Kaushansky, K., Lopez, J.A. and C.B. Brown, "Role of Carbohydrate Modification in the Production and Secretion of Human Granulocyte Macrophage Colony–Stimulating Factor in Genetically Engineered and Normal Mesenchymal Cells," *Biochemistry*, 31:1881–1886 (1992).

Kuroda, K., Hildegard, G., Geyer, R., Doerfler, W. and H–D Klenk, "The Oligosaccharides of Influenza Virus Hemagglutinin Expressed in Insect Cells by a Baculovirus Vector," *Virology*, 174:418–429 (1990).

Kyte, J., and R. F. Doolittle, "A Simple Method for Displaying the Hydropathic Character of a Protein," *J. Mol. Biol.*, 157:105–132 (1982).

Laemmli, U. K., "Cleavage of Structural Proteins During the Assembly of the Head of Bacteriophage T4," *Nature*, 227:680–685 (1970).

Larsen, R. D., Rajan, V. P., Ruff, M. M., Kukowska–Latallo, J., Cummings, R. D., and J. B. Lowe, "Isolation of a cDNA encoding a murine UDPgalactose: β–D–galactosyl–1, 4–N–acetyl–D–glucosaminide α–1,3–galactosyltransferase: Expression cloning by gene transfer," *Proc. Natl. Acad. Sci.*, 86:8227–8231 (1989).

Nagata, Y., Yamashiro, S., Yodoi, J., Lloyd, K. O., Shiku, H., and K. Furukawa, "Expression Cloning of β1,4N–Acetylgalactosaminyltransferase cDNAs That Determine the Expression of $G_{M2}$ and $G_{D2}$ Gangliosides," *J. Biol. Chem.*, 267(17):12082–12089 (1992).

Nakashima, H., Nishikawa, K., and T. Ooi, "The Folding Type of a Protein is Relevant to the Amino Acid Composition," *J. Biochem.*, 99:153–162 (1986).

O'Connell, B., Tabak, L.A. and N. Ramasubbu, "The Influence of Flanking Sequences on O–Glycosylation," *Biochem. Biophys. Res. Commun.*, 180(2):1024–1030 (1991).

O'Connell, B.C., Hagen, F.K., and L.A. Tabak, "The Influence of Flanking Sequence on the O–Glycosylation of Threonine in Vitro," *J. Biol. Chem.*, 267(35):25010–25018 (1992).

O'Connell, B.C., & L.A. Tabak, "Separation of Glycopeptides from in Vitro O–Glycosylation Reactions Using C18 Cartridges," *Anal. Biochem.*, 210:423–425 (1993).

Parodi, A. J., Blank, E. W., Peterson, J., and R. Ceriani, "Glycosyl transferases in mouse and human milk fat globule membranes," *Mol. Cell. Biochem.*, 58:157–163 (1984).

Paulson, J. C., Beranek, W. E., and R. L. Hill, "Purification of a Sialyltransferase from Bovine Colostrum by Affinity Chromatography on CDP–agarose," *J. Biol. Chem.,* 252(7):2356–2362 (1977).

Paulson, J. C., Glycoproteins: what are the sugar chains for? *Trends Biochem. Sci.,* 14:272–275 (1989).

Paulson, J. C., and K. J. Colley, "Glycosyltransferases," *J. Biol. Chem.,* 264(30):17615–17618 (1989).

Piller, V., Piller, F., Klier, F.G., and M. Fukuda, "O–Glycosylation of luekosialin in K562 cells–Evidence for initiation and elongation in early Golgi compartments," *Eur. J. Biochem.,* 183:123–135 (1989).

Piller, V., Piller, F., and M. Fukuda, *J. Biol. Chem.,* 265(16):9264–9271 (1990).

Pisano, A., Redmond, J.W., Williams, K.L., & A.A. Gooley, "Glycosylation sites identified by solid–phase Edman degradation: O–linked glycosylation motifs on human glycophorin A," Glycobiology 3(5):429–435 (1993).

Poorman, R.A., Tomasselli, A.G., Heinrikson, R.L., and F.J. Kézdy, "A Cumulative Specificity Model for Proteases from Human Immunodeficiency Virus Types 1 and 2, Inferred from Statistical Analysis of an Extended Substrate Data Base," *J. Biol. Chem.,* 266(22):14554–14561 (1991).

Prieels, J.–P., Maes, E., Dolmans, M., and J. Leonis, "Heterogeneity of Human Milk β(1–4)–D–Galactosyltransferase," *Eur. J. Biochem.,* 60:525–531 (1975).

Prockop, D.J., Kivirikko, K.I., Tuderman, L., and N.A. Guzman, "The Biosynthesis of Collagen and its Disorders," *New Engl. J. Med.,* 301(1):13–23 (1979).

Rademacher, T.W., Parekh, R.B., and R.A. Dwek, Ann. Rev., *Biochem.,* 57:785–838 (1988).

Rodén, L. and R. Smith, "Structure of the Neutral Trisaccharide of the Chondroitin 4–Sulfate–Protein Linkage Region," *J. Biol. Chem.,* 241(24):5949–5954 (1966).

Roseman, S., "The Synthesis of Complex Carbohydrates by Multigylcosyltransferase Systems and Their Potential Function in Intercellular Adhesion," *Chem. Phys. Lipids,* 5:270–297 (1970).

Roth, J., "Cytochemical Localization of Terminal N–Acetyl–D–galactosamine Residues in Cellular Compartments of Intestinal Goblet Cells: Implications for the Topology of O–Glycosylation," *J. Cell Biol.,* 98:399–406 (1984).

Russo, R. N., Shaper, N. L., and J. H. Shaper, "Bovine β1–4–Galactosyltransferase: Two Sets of mRNA Transcripts Encode Two Forms of the Protein with Different Amino- –terminal Domains," *J. Biol. Chem.,* 265(6):3324–3331 (1990).

Sadler, J.E. (1984), "Biosynthesis of Glycoproteins: Formation of O–Linked Oligosaccharides," *Biology of Carbohydrates,* Ginsburg, V., and Robbins, P.W., Eds., vol. 2, pp. 199–213, John Wiley and Sons, New–York NY.

Sanger, F., Nicklen, S., and A. R. Coulson, "DNA sequencing with chain–terminating inhibitors," *Proc. Natl. Acad. Sci. USA,* 74(12):5463–5467 (1977).

Sarkar, M., Hull, E., Nishikawa, Y., Simpson, R. J., Moritz, R. L., Dunn, R., and H. Schachter, "Molecular cloning and expression of cDNA encoding the enzyme that controls conversion of high–mannose to hybrid and complex N–glycans: UDP–N–acetylglucosamine: α–3–D–mannoside β–1, 2–N–acetylglucosaminyltransferase I," *Proc. Natl. Acad. Sci.,* 88:234–238 (1991).

Schachter, H. and I. Brockhausen, "The Biosynthesis of Serine (Threonine)–N–Acetylgalactosamine–Linked Carbohydrate Moieties," *Glycoconjugates,* Allen, H.J. and E.C. Kisailus, Eds. 263–332 Marcel Dekker Inc., New York, Basel, Hong Kong (1992).

Schmid, K., Hediger, M.A., Brossmer, R., Collins, J.H., Haupt, H., Marti, T., Offner, G.D., Schaller, J., Takagaki, K., Walsh, M.T., Schwick, H.G., Rosen, F.S., and E. Remold–O'Donnell, "Amino acid sequence of human plasma galactoglycoprotein: Identity with the extracellular region of DC43 (sialophorin)," *Proc. Natl. Acad. Sci. USA,* 89:663–667 (1992).

Scocca, J. R., and S. S. Krag, "Sequence of a cDNA That Specifies the Uridine Diphosphate N–Acetyl–D–glucosamine: Dolichol Phosphate N–Acetylglucosamine–1–phosphate Transferase from Chinese Hamster Ovary Cells," *J. Biol. Chem.,* 265(33):20621–20626 (1990).

Shaper, J.H., & N.L. Shaper, "Enzymes associated with glycosylation," Curr. Opin. Struct. Biol. 2:701–709 (1992).

Stoolman, L.M., "Adhesion Molecules Controlling Lymphocyte Migration," *Cell,* 56:907–910 (1989).

Sugiura, M., Kawasaki, T. and I. Yamashina, "Purification and Characterization of UDP–GalNAc: Polypeptide N–Acetylgalactosamine Transferase from an Ascites Hepatoma, AH 66," J. Biol. Chem., 257:9501–9507 (1982).

Summers, M. D., and Smith, G. E. (1986),*A manual of methods for baculovirus vectors and insect cell culture procedures.* College Station: Texas Agricultural Experimental Station.

Svensson, E. C., Soreghan, B., and J. C. Paulson, "Organization of the β–Galactoside α2,6–Sialyltransferase Gene," *J. Biol. Chem.,* 265(34):20863–20868 (1990).

Tessier, D.C., Thomas, D.Y., Khouri, H.E., Laliberté, F., & T. Vernet, "Enhanced secretion from insect cells of a foreign protein fused to the honeybee melittin signal peptide," *Gene,* 98:177–183 (1991).

Thomsen, D. R., Post, L. E., and Å. P. Elhammer, "Structure of O–Glycosidically Linked Oligosaccharides Synthesized by the Insect Cell Line Sf9," *J. Cell. Biochem.,* 43:67–79 (1990).

Thomsen, D.R., Meyer, A.L., & Post, L.E. in *Insect Cell Culture and Engineering*—"Applications of Insect Cell Gene Expression in Pharmaceutical Research" (Goosen, M.F.A., Daugulis, A.J., & Faulkner, P., Eds.) pp.105–138, Marcel Dekker, Inc., New York, Basel, Hong Kong (1993).

Toone, E.J., Simon, E.S., Bednarski, M.D. and G.M. Whitesides, "Enzyme–Catalyzed Synthesis of Carbohydrates," *Tetrahedron Report,* 45(17):5365–5422 (1989).

Tooze, S.A., Tooze, J., and G. Warren, "Site of Addition of N–Acetyl–galactosamine to the E1 Glycoprotein of Mouse Hepatitis Virus–A59," *J. Cell Biol.,* 106:1475–1487 (1988).

Ulmer, J.B., and G.E. Palade, "Targeting and processing of glycophorins in murine erythroleukemia cells: Use of brefeldin A as a perturbant of intracellular traffic," *Proc. Natl. Acad. Sci. USA,* 86:6992–6996 (1989).

Wang, Y., Abernethy, J.L., Eckhardt, A.E., and R.L. Hill, "Purification and Characterization of a UDP–GalNAc: Polypeptide N–Acetylgalactosaminyltransferase Specific for Glycosylation of Threonine Residues," *J. Biol. Chem.,* 267(18):12709–12716 (1992).

Wang, X., O'Hanlon, T. P., Young, R. F., and J. T. Y. Lau, "Rat β–galactoside α2,6–sialyltransferase genomic organization: alternate promoters direct the synthesis of liver and kidney transcripts," *Glycobiology,* 1(1):25–31 (1990).

Wang, Y., Agrwal, N., Eckhardt, A.E., Stevens, R.D., & R.L. Hill, "The Acceptor Substrate Specificity of Porcine Submaxillary UDP–GalNAc: Polypeptide N–Acetylgalactosaminyltransferase is Dependent on the Amino Acid Sequences Adjacent to Serine and Threonine Residues," *J. Biol. Chem.* 268(31):22979–22983 (1993).

Wathen, M. W., Aeed, P. A., and Å. P. Elhammer, "Characterization of Oligosaccharide Structures on a Chimeric Respiratory Syncytial Virus Protein Expressed in Insect Cell Line Sf9," *Biochemistry,* 30:2863–2868 (1991).

Weinstein, J., Lee, E. U., McEntee, K., Lai, P.–H., and J. C. Paulson, "Primary Structure of β–Galactoside α2,6–Sialyltransferase," *J. Biol. Chem.,* 262(36):17735–17743 (1987).

Wen, D. X., Svensson, E. C., and J. C. Paulson, "Tissue–specific Alternative Splicing of the β–Galactoside α2,6–Sialyltransferase Gene," *J. Biol. Chem.,* 267(4): 2512–2518 (1992).

Wertz, G.W., Krieger, M., and L.A. Ball, "Structure and Cell Surface Maturation of the Attachment Glycoprotein of Human Respiratory Syncytial Virus in a Cell Line Deficient in O Glycosylation," *J. Virol.,* 63(11):4767–4776 (1989).

Wessel, D., & U.I. Flugge, "A Method for the Quantitative Recovery of Protein in Dilute Solution in the Presence of Detergents and Lipids," *Anal. Biochem.,* 138:141–143 (1984).

Young, J.D., Tsuchiya, D., Sandlin, D.E., and M.J. Holroyde, "Enzymic O–Glycosylation of Synthetic Peptides from Sequences in Basic Myelin Protein," *Biochemistry,* 18:4444–4448 (1979).

A. Hagopian et al., "Glycoprotein Biosynthesis: Purification, and Characterization of a Polypeptide: N–acetylgalactosaminyl Transferase From Bovine Submaxillary Glands" Chem. Absts. 70 (15): 29, Abst. No. 64521 citing Arch. Biocem Biophys. 129 (2): 515–524, Apr. 1969.

```
  1               5                  10                 15                 20                 25                 30              34
GLY LEU PRO ALA GLY VAL LEU GLU ASP VAL GLN LYS PRO HIS GLU GLY PRO GLY LYS PRO VAL VAL ILE PRO LYS VAL GLU ASP GLN GLU LYS

5'-GCX GGX GAN GTX CTZ GAR CC-3'  OLIGO A                                 OLIGO C   3'- TTN CTN CTR GTN CTN TTN-5'
                                                                          OLIGO E   5'- TC ATT CCT AAA GAG GAC C-3'
                      5'-CAR AAR CCX CAN GAR GG-3'  OLIGO B
                      5'-CAA AAG CCT CAT GAA GGT CC-3'  OLIGO D
                                                                                    X=G+A+T+C
                                                                                    N=T+C
                                                                                    R=A+G
                                                                                    Y=C+G
                                                                                    Z=A+T
```

FIG. 2A

```
                              EcoRI
CAAGTTCAGCCTGGTTAAGTCCAAGCTGAATTCTTTTGCTTTTTACCCTGGAAGAAATAC  λgt10
5'-CAAGTTCAGCCTGGTTAAGTCC-3'                3'-CGAAAAATGGGACCTTCTTTATG-5'

OLIGO F                                      OLIGO G
```

FIG. 2B

GGAACTAACCCTGAAGTTAGAATTGGATTACTTCATTGACTTAAAGTGCC ATG AGA AAA TTT GCA TAC TGC AAG GTG GTC CTA GCC ACC TCC TTG ATT TGG GTA CTC TTG GAT    115
                                                  Met Arg Lys Phe Ala Tyr Cys Lys Val Val Leu Ala Thr Ser Leu Ile Trp Val Leu Leu Asp    21

ATG TTC CTG CTG TAC TTC AGT GAA TGC AAC AAA TGT GAT GAA AAA GAG AGA GAA CTT CCT GCT GGG GAT GTT CTA GAG CCA GTA CAA AAG CCT CAT    217
Met Phe Leu Leu Tyr Phe Ser Glu Cys Asn Lys Cys Asp Glu Lys Glu Arg Glu Leu Pro Ala Gly Asp Val Leu Glu Pro Val Gln Lys Pro His    55

GAA GGT CCT GGA GAA ATG GGG AAA CCA GTC ATT CCT CTA AAA GAG GAT CAA GAA ATG AAA GAG ATG TTT AAA ATC AAT CAG TTC AAT TTA ATG GCA AGT    319
Glu Gly Pro Gly Glu Met Gly Lys Pro Val Ile Pro Leu Lys Glu Asp Gln Glu Met Lys Glu Met Phe Lys Ile Asn Gln Phe Asn Leu Met Ala Ser    89

GAG ATT GCA CTC AGA TCT CTA CCA GAT GTT AGA TTA GAA GGG TGT AAA ACA GTG TAT CCA GAT AAC CTT CCT ACA ACC AGT GTG GTG ATT GTT    421
Glu Ile Ala Leu Arg Ser Leu Pro Asp Val Arg Leu Glu Gly Cys Lys Thr Val Tyr Pro Asp Asn Leu Pro Thr Thr Ser Val Val Ile Val    123

TTC CAC AAT GAG GCT TGG TCA CGA CTT CTG CAT AGC GTC ATT AAT CGC TCA CCA AGG CAC ATG CTA GAA GAA ATT GTT CTA GTA GAT GAT GCC    523
Phe His Asn Glu Ala Trp Ser Arg Leu Leu His Ser Val Ile Asn Arg Ser Pro Arg His Met Leu Glu Glu Ile Val Leu Val Asp Asp Ala    157

AGT GAA AGA GAC TTT AAA AGA CTA GAG AGT TAC GTC AAA TTA CCC CGT GTT CAC GTC ATT CGA ATG GAG CAG TCT GGA TTG ATC AGA    625
Ser Glu Arg Asp Phe Lys Arg Leu Glu Ser Tyr Val Lys Leu Pro Arg Val His Val Ile Arg Met Glu Gln Ser Gly Leu Ile Arg    191

GCT AGG TTA AAA GGT GCT GTG TCT AAA GGT GTC CAA GTG ATC ACC TTT TTA GAC GCG CAC TGT GAG TGC ACA GTG GGG CTG TGG CCT CTC TTA GCC AGG    727
Ala Arg Leu Lys Gly Ala Val Ser Lys Gly Val Gln Val Ile Thr Phe Leu Asp Ala His Cys Glu Cys Thr Val Gly Trp Leu Pro Leu Ala Arg    225

ATC AAA CAT GAC CTC AAC TTT CGC GTC GTC TGT CCC GTT CCT ATA GAT GTG CAA AGA GAA ATG GAC AGA GGT AAA GAC ACT CTT GAC TCT GAA ATG GCC GGT TAC ACC TAT GCC GGG TTC    829
Ile Lys His Asp Leu Asn Phe Arg Val Val Cys Pro Ile Ile Asp Val Ile Ser Asp Arg Gln Arg Arg Lys Gly Met Asp Arg Phe Glu Tyr Met Ala Gly Ser Asp Met Thr Tyr Gly Gly Phe    259

AAC TGG AAG CTC AAC TTC CGC TGG TAT CCT GTT CCC CAA AGA ATT CAG GAA ATT TGG GGA GAA AGT GAT GGT GAC ACT CCT GTC AGA CTC CGG ACA ACA ATG GCA GGA    931
Asn Trp Lys Leu Asn Phe Arg Trp Tyr Pro Val Pro Gln Arg Ile Gln Glu Ile Trp Gly Glu Ser Asp Val Asp Thr Pro Val Arg Leu Pro Thr Met Ala Gly    293

GGC CTT TTT TCA ATA GAC AGA GAT TAC TTT CAG GAA ATT GGA ACA TAT GAT GCT GGA ATG GAT ATT TGG GGA GGA GAA AAC CTA GAA ATT TCC TTT AGG ATT    1033
Gly Leu Phe Ser Ile Asp Arg Asp Tyr Phe Gln Glu Ile Gly Thr Tyr Asn Ala Gly Met Asp Ile Trp Gly Gly Glu Asn Leu Glu Ile Ser Phe Arg Ile    327

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
       (A) LENGTH: 34 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:1:

Gly Leu Pro Ala Gly Asp Val Leu Glu Pro Val Gln Lys Pro His Glu
 1               5                  10                  15

Gly Pro Gly Glu Met Gly Lys Pro Val Val Ile Pro Lys Glu Asp Gln
                20                  25                  30

Glu Lys (2) INFORMATION FOR SEQ ID NO:2:

(i) SEQUENCE CHARACTERISTICS:
       (A) LENGTH: 20 base pairs
       (B) TYPE: nucleic acid
       (C) STRANDEDNESS: single (D) TOPOLOGY: linear (ii) MOLECULE TYPE: cDNA (xi) SEQUENCE DESCRIPTION: SEQ ID NO:2:

GCNGGNGAYG TNCTWGARCC                                                   20

(2) INFORMATION FOR SEQ ID NO:3:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

CARAARCCNC AYGARGG                                                      17

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

TTYCTYCTRG TYCTYTTY                                                     18

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

CAAAAGCCTC ATGAAGGTCC                                                   20

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

TCATTCCTAA AGAGGACC                                                     18

(2) INFORMATION FOR SEQ ID NO:7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA -continued (xi) SEQUENCE DESCRIPTION: SEQ ID NO:7:

CAAGTTCAGC CTGGTTAAGT CC                                                22

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

CGAAAAATGG GACCTTCTTT ATG                                               23

(2) INFORMATION FOR SEQ ID NO:9:

(i) SEQUENCE CHARACTERISTICS:
        (A) LENGTH: 559 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

```
Met Arg Lys Phe Ala Tyr Cys Lys Val Val Leu Ala Thr Ser Leu Ile
 1               5                  10                  15

Trp Val Leu Leu Asp Met Phe Leu Leu Tyr Phe Ser Glu Cys Asn
                20                  25                  30

Lys Cys Asp Glu Lys Lys Glu Arg Gly Leu Pro Ala Gly Asp Val Leu
         35                  40                  45

Glu Pro Val Gln Lys Pro His Glu Gly Pro Gly Glu Met Gly Lys Pro
     50                  55                  60

Val Val Ile Pro Lys Glu Asp Gln Glu Lys Met Lys Glu Met Phe Lys
 65                  70                  75                  80

Ile Asn Gln Phe Asn Leu Met Ala Ser Glu Met Ile Ala Leu Asn Arg
                 85                  90                  95

Ser Leu Pro Asp Val Arg Leu Glu Gly Cys Lys Thr Lys Val Tyr Pro
            100                 105                 110

Asp Asn Leu Pro Thr Thr Ser Val Val Ile Val Phe His Asn Glu Ala
        115                 120                 125

Trp Ser Thr Leu Leu Arg Thr Val His Ser Val Ile Asn Arg Ser Pro
    130                 135                 140

Arg His Met Leu Glu Glu Ile Val Leu Val Asp Asp Ala Ser Glu Arg
145                 150                 155                 160

Asp Phe Leu Lys Arg Pro Leu Glu Ser Tyr Val Lys Lys Leu Lys Val
                165                 170                 175

Pro Val His Val Ile Arg Met Glu Gln Arg Ser Gly Leu Ile Arg Ala
            180                 185                 190

Arg Leu Lys Gly Ala Ala Val Ser Lys Gly Gln Val Ile Thr Phe Leu
        195                 200                 205

Asp Ala His Cys Glu Cys Thr Val Gly Trp Leu Glu Pro Leu Leu Ala
    210                 215                 220

Arg Ile Lys His Asp Arg Lys Thr Val Val Cys Pro Ile Ile Asp Val
225                 230                 235                 240

Ile Ser Asp Asp Thr Phe Glu Tyr Met Ala Gly Ser Asp Met Thr Tyr
                245                 250                 255
```

```
Gly Gly Phe Asn Trp Lys Leu Asn Phe Arg Trp Tyr Pro Val Pro Gln
            260                 265                 270

Arg Glu Met Asp Arg Arg Lys Gly Asp Arg Thr Leu Pro Val Arg Thr
            275                 280                 285

Pro Thr Met Ala Gly Gly Leu Phe Ser Ile Asp Arg Asp Tyr Phe Gln
            290                 295                 300

Glu Ile Gly Thr Tyr Asp Ala Gly Met Asp Ile Trp Gly Gly Glu Asn
305                 310                 315                 320

Leu Glu Ile Ser Phe Arg Ile Trp Gln Cys Gly Gly Thr Leu Glu Ile
                325                 330                 335

Val Thr Cys Ser His Val Gly His Val Phe Arg Lys Ala Thr Pro Tyr
            340                 345                 350

Thr Phe Pro Gly Gly Thr Gly Gln Ile Ile Asn Lys Asn Asn Arg Arg
            355                 360                 365

Leu Ala Glu Val Trp Met Asp Glu Phe Lys Asn Phe Phe Tyr Ile Ile
            370                 375                 380

Ser Pro Gly Val Thr Lys Val Asp Tyr Gly Asp Ile Ser Ser Arg Leu
385                 390                 395                 400

Gly Leu Arg His Lys Leu Gln Cys Arg Pro Phe Ser Trp Tyr Leu Glu
                405                 410                 415

Asn Ile Tyr Pro Asp Ser Gln Ile Pro Arg His Tyr Phe Ser Leu Gly
                420                 425                 430

Glu Ile Arg Asn Val Glu Thr Asn Gln Cys Leu Asp Asn Met Ala Arg
                435                 440                 445

Lys Glu Asn Glu Lys Val Gly Ile Phe Asn Cys His Gly Met Gly Gly
            450                 455                 460

Asn Gln Val Phe Ser Tyr Thr Ala Asn Lys Glu Ile Arg Thr Asp Asp
465                 470                 475                 480

Leu Cys Leu Asp Val Ser Lys Leu Asn Gly Pro Val Thr Met Leu Lys
                485                 490                 495

Cys His His Leu Lys Gly Asn Gln Leu Trp Glu Tyr Asp Pro Val Lys
            500                 505                 510

Leu Thr Leu Gln His Val Asn Ser Asn Gln Cys Leu Asp Lys Ala Thr
            515                 520                 525

Asp Glu Asp Ser Gln Val Pro Ser Ile Arg Asp Cys Ser Gly Ser Arg
            530                 535                 540

Ser Gln Gln Trp Leu Leu Arg Asn Val Thr Leu Pro Glu Ile Phe
545                 550                 555

(2) INFORMATION FOR SEQ ID NO:10:

(i) SEQUENCE CHARACTERISTICS:
        (A) LENGTH: 2294 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:10:

GGAACTAACC CTGAAGTTAG AATTGGATTA CTTTCATTTG ACTTAAAGTG CCATGAGAAA      60

ATTTGCATAC TGCAAGGTGG TCCTAGCCAC CTCCTTGATT TGGGTACTCT TGGATATGTT     120

CCTGCTGCTT TACTTCAGTG AATGCAACAA ATGTGATGAA AAAAAGAGA GAGGACTTCC      180

TGCTGGGGAT GTTCTAGAGC CAGTACAAAA GCCTCATGAA GGTCCTGGAG AAATGGGGAA     240
```

```
ACCAGTCGTC ATTCCTAAAG AGGATCAAGA AAAGATGAAA GAGATGTTTA AAATCAATCA      300

GTTCAATTTA ATGGCAAGTG AGATGATTGC ACTCAACAGA TCTCTACCAG ATGTTAGATT      360

AGAAGGGTGT AAAACAAAGG TGTATCCAGA TAACCTTCCT ACAACCAGTG TGGTGATTGT      420

TTTCCACAAT GAGGCTTGGA GCACACTTCT GCGAACTGTC CATAGCGTCA TTAATCGCTC      480

ACCAAGGCAC ATGCTAGAAG AAATTGTTCT AGTAGATGAT GCCAGTGAAA GAGACTTTTT      540

AAAAAGACCT CTAGAGAGTT ACGTGAAAAA ATTAAAAGTA CCCGTTCACG TCATTCGAAT      600

GGAGCAGCGT TCTGGATTGA TCAGAGCTAG GTTAAAAGGT GCTGCTGTGT CTAAAGGCCA      660

AGTGATCACC TTTTTAGACG CGCACTGTGA GTGCACAGTG GGGTGGCTGG AGCCTCTCTT      720

AGCCAGGATC AAACATGACA GGAAGACAGT GGTCTGTCCC ATCATAGATG TGATCAGTGA      780

TGACACTTTC GAGTACATGG CAGGTTCTGA CATGACCTAT GGCGGGTTCA ACTGGAAGCT      840

CAACTTTCGC TGGTATCCTG TTCCCCAAAG AGAAATGGAC AGAAGGAAAG GTGATCGGAC      900

TCTTCCTGTG AGAACACCTA CAATGGCAGG AGGCCTTTTT TCAATAGACA GAGATTACTT      960

TCAGGAAATT GGAACATATG ATGCTGGAAT GGATATTTGG GGAGGAGAAA ACCTAGAAAT     1020

TTCCTTTAGG ATTTGGCAGT GTGGAGGAAC TTTGGAGATT GTTACTTGCT CACATGTTGG     1080

ACATGTGTTT CGGAAAGCTA CACCCTACAC GTTTCCAGGA GGCACGGGGC AGATTATCAA     1140

TAAAAATAAC AGACGACTTG CAGAAGTATG GATGGATGAA TTCAAGAATT TCTTCTATAT     1200

AATTTCTCCA GGTGTTACAA AGGTAGATTA TGGAGATATA TCATCAAGAC TTGGTCTAAG     1260

GCACAAACTC CAATGCAGAC CATTCTCTTG GTACCTAGAG AATATTTATC CTGATTCTCA     1320

GATTCCTCGT CACTATTTCT CTTTGGGAGA GATACGAAAT GTGGAAACAA ATCAGTGTCT     1380

AGATAACATG GCTAGAAAAG AGAATGAAAA AGTTGGAATT TTTAACTGTC ATGGTATGGG     1440

AGGTAATCAG GTTTTCTCTT ACACTGCCAA CAAAGAAATT AGAACAGATG ACCTTTGCTT     1500

GGATGTCTCC AAACTTAATG GCCCAGTCAC AATGCTCAAA TGCCACCACC TAAAAGGCAA     1560

CCAGCTTTGG GAGTATGACC CGGTGAAGTT GACCCTGCAG CATGTGAACA GTAACCAGTG     1620

CCTGGACAAA GCCACAGACG AGGACAGCCA GGTGCCCAGC ATCAGAGACT GCAGCGGAAG     1680

CCGATCCCAG CAGTGGCTTC TTCGGAACGT CACCCTTCCA GAAATATTCT GAGACCAAAT     1740

TTACAAAAAA AGGAAAACGT AAGGACTGAC TGGGCTACCT CAGCATACAT TTCTGCCACA     1800

TTCTTAAGTA GCAAAAAAAG GAAAAGTGCT TTCCTTCTGC AGGATGTAAG GTTTATCAGC     1860

CATTAAAACT TTATAGACTG CCCTCGCTTC CACTAGCTGT GAACCAGCCT TCCTGTCCCA     1920

GGACGTGCAA CTACGTAGTA GCGAGACTGT GCACACTGAT GTTTACAAGA TTGAAAGAGT     1980

CGGTCATCAA GAATCCTCGT AAAGAATACT CAGACTGAAA CAGTCTGCGA ACTGTGCTTT     2040

CCAGAGAGCT GCGCCTTTTA TGGTTTGCGT GCACAGCAGT GAGTTCCGCT GACTGTGCTG     2100

TCATAATGAA GAGACGTCTA AGATTTTTTT TCTGATTAGA ACTGGTAGCC AGTATATTAA     2160

ATACTGATAT AAAAATAAAT GAACTGGAAC CAGATTCAGA ATCATGAAAA CATTTTTACA     2220

ATTTAAAAAA AACAAAACTA TATTAAACAG GGTTTAAAGG AATTAAAACA AAAAAAAAA      2280

AAAAAAAAAA AAAA                                                       2294
```

(2) INFORMATION FOR SEQ ID NO:11:

(i) SEQUENCE CHARACTERISTICS:
        (A) LENGTH: 1680 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:11:

```
ATGAGAAAAT TTGCATACTG CAAGGTGGTC CTAGCCACCT CCTTGATTTG GGTACTCTTG      60

GATATGTTCC TGCTGCTTTA CTTCAGTGAA TGCAACAAAT GTGATGAAAA AAAAGAGAGA     120

GGACTTCCTG CTGGGGATGT TCTAGAGCCA GTACAAAAGC CTCATGAAGG TCCTGGAGAA     180

ATGGGGAAAC CAGTCGTCAT TCCTAAAGAG GATCAAGAAA AGATGAAAGA GATGTTTAAA     240

ATCAATCAGT TCAATTTAAT GGCAAGTGAG ATGATTGCAC TCAACAGATC TCTACCAGAT     300

GTTAGATTAG AAGGGTGTAA ACAAAGGTG TATCCAGATA ACCTTCCTAC AACCAGTGTG      360

GTGATTGTTT TCCACAATGA GGCTTGGAGC ACACTTCTGC GAACTGTCCA TAGCGTCATT     420

AATCGCTCAC CAAGGCACAT GCTAGAAGAA ATTGTTCTAG TAGATGATGC CAGTGAAAGA     480

GACTTTTTAA AAAGACCTCT AGAGAGTTAC GTGAAAAAAT TAAAAGTACC CGTTCACGTC     540

ATTCGAATGG AGCAGCGTTC TGGATTGATC AGAGCTAGGT TAAAAGGTGC TGCTGTGTCT     600

AAAGGCCAAG TGATCACCTT TTTAGACGCG CACTGTGAGT GCACAGTGGG GTGGCTGGAG     660

CCTCTCTTAG CCAGGATCAA ACATGACAGG AAGACAGTGG TCTGTCCCAT CATAGATGTG     720

ATCAGTGATG ACACTTTCGA GTACATGGCA GGTTCTGACA TGACCTATGG CGGGTTCAAC     780

TGGAAGCTCA ACTTTCGCTG GTATCCTGTT CCCCAAAGAG AAATGGACAG AAGGAAAGGT     840

GATCGGACTC TTCCTGTGAG AACACCTACA ATGGCAGGAG GCCTTTTTTC AATAGACAGA     900

GATTACTTTC AGGAAATTGG AACATATGAT GCTGGAATGG ATATTTGGGG AGGAGAAAAC     960

CTAGAAATTT CCTTTAGGAT TTGGCAGTGT GGAGGAACTT TGGAGATTGT TACTTGCTCA    1020

CATGTTGGAC ATGTGTTTCG GAAAGCTACA CCCTACACGT TTCCAGGAGG CACGGGGCAG    1080

ATTATCAATA AAAATAACAG ACGACTTGCA GAAGTATGGA TGGATGAATT CAAGAATTTC    1140

TTCTATATAA TTTCTCCAGG TGTTACAAAG GTAGATTATG GAGATATATC ATCAAGACTT    1200

GGTCTAAGGC ACAAACTCCA ATGCAGACCA TTCTCTTGGT ACCTAGAGAA TATTTATCCT    1260

GATTCTCAGA TTCCTCGTCA CTATTTCTCT TTGGGAGAGA TACGAAATGT GGAAACAAAT    1320

CAGTGTCTAG ATAACATGGC TAGAAAAGAG AATGAAAAAG TTGGAATTTT TAACTGTCAT    1380

GGTATGGGAG GTAATCAGGT TTTCTCTTAC ACTGCCAACA AAGAAATTAG AACAGATGAC    1440

CTTTGCTTGG ATGTCTCCAA ACTTAATGGC CCAGTCACAA TGCTCAAATG CCACCACCTA    1500

AAAGGCAACC AGCTTTGGGA GTATGACCCG GTGAAGTTGA CCCTGCAGCA TGTGAACAGT    1560

AACCAGTGCC TGGACAAAGC CACAGACGAG GACAGCCAGG TGCCCAGCAT CAGAGACTGC    1620

AGCGGAAGCC GATCCCAGCA GTGGCTTCTT CGGAACGTCA CCCTTCCAGA AATATTCTGA    1680
```

(2) INFORMATION FOR SEQ ID NO:12:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

```
Arg Thr Pro Pro Pro
1               5
```

(2) INFORMATION FOR SEQ ID NO:13:

(i) SEQUENCE CHARACTERISTICS:
    (A) LENGTH: 5 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:13:

Arg Ser Pro Pro Pro
1               5

(2) INFORMATION FOR SEQ ID NO:14:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Pro Pro Ala Ser Thr Ser Ala Pro Gly
1               5

(2) INFORMATION FOR SEQ ID NO:15:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Pro Pro Ala Ser Ser Ser Ala Pro Gly
1               5

(2) INFORMATION FOR SEQ ID NO:16:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

CAAGTTCAGC CTGGTTAAGT CCAAGCTGAA TTCTTTTGCT TTTTACCCTG GAAGAAATAC    60

(2) INFORMATION FOR SEQ ID NO:17:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Pro Pro Asp Ala Ala Ser Ala Ala Pro Leu Arg
1               5                   10

(2) INFORMATION FOR SEQ ID NO:18:

(i) SEQUENCE CHARACTERISTICS:
        (A) LENGTH: 1617 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:18:

```
ATGAAATTCT TAGTCAACGT TGCCCTTGTT TTTATGGTCG TGTACATTTC TTACATCTAT      60

GCGGATCCAA GCCCTGCTCT AGAGCCAGTA CAAAAGCCTC ATGAAGGTCC TGGAGAAATG     120

GGGAAACCAG TCGTCATTCC TAAAGAGGAT CAAGAAAAGA TGAAAGAGAT GTTTAAAATC     180

AATCAGTTCA ATTTAATGGC AAGTGAGATG ATTGCACTCA ACAGATCTCT ACCAGATGTT     240

AGATTAGAAG GGTGTAAAAC AAAGGTGTAT CCAGATAACC TTCCTACAAC CAGTGTGGTG     300

ATTGTTTTCC ACAATGAGGC TTGGAGCACA CTTCTGCGAA CTGTCCATAG CGTCATTAAT     360

CGCTCACCAA GGCACATGCT AGAAGAAATT GTTCTAGTAG ATGATGCCAG TGAAAGAGAC     420

TTTTTAAAAA GACCTCTAGA GAGTTACGTG AAAAAATTAA AAGTACCCGT TCACGTCATT     480

CGAATGGAGC AGCGTTCTGG ATTGATCAGA GCTAGGTTAA AAGGTGCTGC TGTGTCTAAA     540

GGCCAAGTGA TCACCTTTTT AGACGCGCAC TGTGAGTGCA CAGTGGGGTG GCTGGAGCCT     600

CTCTTAGCCA GGATCAAACA TGACAGGAAG ACAGTGGTCT GTCCCATCAT AGATGTGATC     660

AGTGATGACA CTTTCGAGTA CATGGCAGGT TCTGACATGA CCTATGGCGG GTTCAACTGG     720

AAGCTCAACT TTCGCTGGTA TCCTGTTCCC AAAGAGAAA TGGACAGAAG GAAAGGTGAT     780

CGGACTCTTC CTGTGAGAAC ACCTACAATG GCAGGAGGCC TTTTTTCAAT AGACAGAGAT     840

TACTTTCAGG AAATTGGAAC ATATGATGCT GGAATGGATA TTTGGGGAGG AGAAAACCTA     900

GAAATTTCCT TTAGGATTTG GCAGTGTGGA GGAACTTTGG AGATTGTTAC TTGCTCACAT     960

GTTGGACATG TGTTTCGGAA AGCTACACCC TACACGTTTC CAGGAGGCAC GGGGCAGATT    1020

ATCAATAAAA ATAACAGACG ACTTGCAGAA GTATGGATGG ATGAATTCAA GAATTTCTTC    1080

TATATAATTT CTCCAGGTGT TACAAAGGTA GATTATGGA ATATATCATC AAGACTTGGT    1140

CTAAGGCACA AACTCCAATG CAGACCATTC TCTTGGTACC TAGAGAATAT TTATCCTGAT    1200

TCTCAGATTC CTCGTCACTA TTTCTCTTTG GGAGAGATAC GAAATGTGGA AACAAATCAG    1260

TGTCTAGATA ACATGGCTAG AAAAGAGAAT GAAAAAGTTG GAATTTTTAA CTGTCATGGT    1320

ATGGGAGGTA ATCAGGTTTT CTCTTACACT GCCAACAAAG AAATTAGAAC AGATGACCTT    1380

TGCTTGGATG TCTCCAAACT TAATGGCCCA GTCACAATGC TCAAATGCCA CCACCTAAAA    1440

GGCAACCAGC TTTGGGAGTA TGACCCGGTG AAGTTGACCC TGCAGCATGT GAACAGTAAC    1500

CAGTGCCTGG ACAAAGCCAC AGACGAGGAC AGCCAGGTGC CCAGCATCAG AGACTGCAGC    1560

GGAAGCCGAT CCCAGCAGTG GCTTCTTCGG AACGTCACCC TTCCAGAAAT ATTCTGA      1617
```

(2) INFORMATION FOR SEQ ID NO:19:

(i) SEQUENCE CHARACTERISTICS:
        (A) LENGTH: 517 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:19:

```
Asp Pro Ser Pro Ala Leu Glu Pro Val Gln Lys Pro His Glu Gly Pro
1               5                   10                  15
```

```
Gly Glu Met Gly Lys Pro Val Ile Pro Lys Glu Asp Gln Glu Lys
             20              25              30
Met Lys Glu Met Phe Lys Ile Asn Gln Phe Asn Leu Met Ala Ser Glu
         35              40                  45
Met Ile Ala Leu Asn Arg Ser Leu Pro Asp Val Arg Leu Glu Gly Cys
     50              55              60
Lys Thr Lys Val Tyr Pro Asp Asn Leu Pro Thr Thr Ser Val Val Ile
 65              70              75                  80
Val Phe His Asn Glu Ala Trp Ser Thr Leu Leu Arg Thr Val His Ser
             85              90                  95
Val Ile Asn Arg Ser Pro Arg His Met Leu Glu Glu Ile Val Leu Val
            100             105             110
Asp Asp Ala Ser Glu Arg Asp Phe Leu Lys Arg Pro Leu Glu Ser Tyr
            115             120             125
Val Lys Lys Leu Lys Val Pro Val His Val Ile Arg Met Glu Gln Arg
            130             135             140
Ser Gly Leu Ile Arg Ala Arg Leu Lys Gly Ala Ala Val Ser Lys Gly
145             150             155                 160
Gln Val Ile Thr Phe Leu Asp Ala His Cys Glu Cys Thr Val Gly Trp
            165             170             175
Leu Glu Pro Leu Leu Ala Arg Ile Lys His Asp Arg Lys Thr Val Val
            180             185             190
Cys Pro Ile Ile Asp Val Ile Ser Asp Asp Thr Phe Glu Tyr Met Ala
            195             200             205
Gly Ser Asp Met Thr Tyr Gly Gly Phe Asn Trp Lys Leu Asn Phe Arg
            210             215             220
Trp Tyr Pro Val Pro Gln Arg Glu Met Asp Arg Arg Lys Gly Asp Arg
225             230             235                 240
Thr Leu Pro Val Arg Thr Pro Thr Met Ala Gly Gly Leu Phe Ser Ile
            245             250             255
Asp Arg Asp Tyr Phe Gln Glu Ile Gly Thr Tyr Asp Ala Gly Met Asp
            260             265             270
Ile Trp Gly Gly Glu Asn Leu Glu Ile Ser Phe Arg Ile Trp Gln Cys
            275             280             285
Gly Gly Thr Leu Glu Ile Val Thr Cys Ser His Val Gly His Val Phe
            290             295             300
Arg Lys Ala Thr Pro Tyr Thr Phe Pro Gly Gly Thr Gly Gln Ile Ile
305             310             315                 320
Asn Lys Asn Asn Arg Arg Leu Ala Glu Val Trp Met Asp Glu Phe Lys
            325             330             335
Asn Phe Phe Tyr Ile Ile Ser Pro Gly Val Thr Lys Val Asp Tyr Gly
            340             345             350
Asp Ile Ser Ser Arg Leu Gly Leu Arg His Lys Leu Gln Cys Arg Pro
            355             360             365
Phe Ser Trp Tyr Leu Glu Asn Ile Tyr Pro Asp Ser Gln Ile Pro Arg
            370             375             380
His Tyr Phe Ser Leu Gly Glu Ile Arg Asn Val Glu Thr Asn Gln Cys
385             390             395                 400
Leu Asp Asn Met Ala Arg Lys Glu Asn Glu Lys Val Gly Ile Phe Asn
            405             410             415
Cys His Gly Met Gly Gly Asn Gln Val Phe Ser Tyr Thr Ala Asn Lys
            420             425             430
```

-continued

```
Glu Ile Arg Thr Asp Asp Leu Cys Leu Asp Val Ser Lys Leu Asn Gly
        435                 440                 445

Pro Val Thr Met Leu Lys Cys His His Leu Lys Gly Asn Gln Leu Trp
        450                 455                 460

Glu Tyr Asp Pro Val Lys Leu Thr Leu Gln His Val Asn Ser Asn Gln
465                 470                 475                 480

Cys Leu Asp Lys Ala Thr Asp Glu Asp Ser Gln Val Pro Ser Ile Arg
                485                 490                 495

Asp Cys Ser Gly Ser Arg Ser Gln Gln Trp Leu Leu Arg Asn Val Thr
                500                 505                 510

Leu Pro Glu Ile Phe
            515
```

CLONED DNA ENCODING A UDP-GALNAC: POLYPEPTIDE, N-ACETYLGALACTOSAMINYLTRANSFERASE

CROSS-REFERENCE TO RELATED APPLICATIONS

This application is a divisional of U.S. Ser. No. 08/602,830 filed Nov. 13, 1995, now abandoned, which is the national phase of international application PCT/US94/02552, filed Mar. 17, 1994 which is a continuation-in-part of U.S. Ser. No. 08/063,186 filed May 14, 1993, now abandoned.

BACKGROUND OF THE INVENTION

The present invention relates to glycosyltransferase enzymes and the genes corresponding to such enzymes. In particular, the present invention relates to the enzyme N-acetylgalactosaminyltransferase. Specifically, the invention relates to the isolation and sequencing of the enzyme N-acetylgalactosaminyltransferase. The invention also relates to the construction of proteins capable of expressing the acceptor peptide for the enzyme N-acetylgalactosaminyltransferase.

Carbohydrates are an important class of biological compounds. In cells, carbohydrates function as structural components where they regulate viscosity, store energy, or are key components of cell surfaces. Nearly all site specific intercellular interactions involve cell surface carbohydrates. For example, union of sperm and egg as well as the implantation of fertilized egg are both mediated by cell surface carbohydrates. Likewise, a number of proteins that function as cell adhesion molecules, including GMP-140, ELAM-1, and lymphocyte adhesion molecules like Mel-14, exhibit structural features that mimic lectins, and are thought to bind specific cell surface carbohydrate structures (Stoolman, Cell (1989) 56:907–910). Glycosylated proteins as tumor-associated antigens are now being used to identify the presence of numerous carcinomas. Even isolated oligosaccharides have been found to exhibit biological activity on their own.

Specific galactose glycosaccharides are known to inhibit the agglutination of uropathogenic coliform bacteria with red blood cells (U.S. Pat. No. 4,521,592). Other oligosaccharides have been shown to possess potent antithrombic activity by increasing the levels of plasminogen activator (U.S. Pat. No. 4,801,583). This same biological activity has been used, by binding oligosaccharides, in conjunction with an amino glycoprotein, to medical instruments to provide medical surfaces which have anticoagulation effects (U.S. Pat. No. 4,810,784). Still other oligosaccharides have found utility as gram positive antibiotics and disinfectants (U.S. Pat. Nos. 4,851,338 and 4,665,060). Further, oligosaccharides have been used as bacteria receptor sites in the diagnosis and identification of specific bacteria (U.S. Pat. Nos. 4,657,849 and 4,762,824).

It is also well recognized that oligosaccharides have an influence on the protein or lipid to which they are conjugated (Rademacher et al., Ann. Rev., Biochem., (1988), 57:785). Specific oligosaccharides have been shown to influence proteins, stability, rate of proteolysis, rate of in vivo clearance from the bloodstream, thermal stability and solubility. Changes in the oligosaccharide portion of cell surface carbohydrates have been noted in cells which have become cancerous. Other oligosaccharide changes have been detected during cell differentiation (Toone et al., Tetrahedron Report (1989) 45(17):5365–5422). As such, the significance of oligosaccharides to biological function cannot be understated.

O-glycosidically linked (mucin type) oligosaccharides have been reported on a number of different types of glycoproteins (Sadler, (1984) Biology of Carbohydrates, (Ginsburg and Robbins, eds.) pp. 199–213, Vol. 2, John Wiley and Sons, New York). These structures have been assigned a diverse array of functions, ranging from quite specific such as being involved in cell—cell recognition and host-pathogen interaction, to more general such as providing protection from proteolytic degradation or supplying the appropriate charge and water binding properties to mucous secretions (Sadler (1984) Biology of Carbohydrates (supra); Paulson (1989) Trends Biochem. 20 Sci., 14:272–275; and Jentoft (1990) Trends Biochem. Sci., 15:291–294).

The initial reaction in O-linked oligosaccharide biosynthesis is the transfer of an N-acetylgalactosamine residue from the nucleotide sugar UDP-N-acetylgalactosamine to a serine or threonine residue on the protein acceptor. This reaction, which can occur post-translationally, is catalyzed by UDP-GalNAc:polypeptide, N-acetylgalactosaminyltransferase (hereinafter referred to as GalNAc-transferase or GalNAcT) an intracellular membrane bound enzyme believed to be localized in the secretory pathway.

The exact location(s) of GalNAc-transferase is still controversial. It has been reported that the initial addition of N-acetylgalactosamine to the acceptor protein can take place early (even co-translationally) in the rough endoplasmic reticulum (ER). Other authors have suggested that this reaction is a post-translational event occurring in later ER compartments and/or in the cis region of the Golgi complex (e.g. Hanover et al. (1982) J. Biol. Chem. 257:10172–10177; Roth (1984) J. Cell Biol. 98:399–406; Elhammer and Kornfeld (1984) J. Cell Biol. 98:327–331; Tooze et al. (1988) J. Cell Biol. 106:1475–1487; Deschuyteneer et al. (1988) J. Biol. Chem. 263:2452–2459; Ulmer and Palade (1989) Proc. Natl. Acad. Sci. (U.S.A.) 89:663–667; Wertz et al. (1989) J. Virol. 63:4767–4776; Piller et al. (1989) Eur. J. Biochem. 183:123–135; Piller et al. (1990) J. Biol. Chem. 265:9264–9271. Finally, evidence has also been presented for a model in which transfer of N-acetylgalactosamine to Ser/Thr may occur in several compartments in the secretory pathway, including compartments later than the Golgi complex (Schachter and Brockhausen (1992) Glycoconjugates, Allen and Kisailus, eds., pp. 263–332, Marcel Dekker Inc., New York). Elongation and termination of O-linked oligosaccharides is accomplished by sequential addition of individual monosaccharides by specific transferases (Roseman (1970) Chem. Phys. Lipids 5:270–280); current data suggest that these reactions are localized primarily in the Golgi apparatus (Schachter and Brockhausen, supra).

The fundamental role of oligosaccharides, particularly, O-glycosidically linked (mucin type) oligosaccharides, to biological function in molecular biology has made them the object of considerable research, in particular, considerable efforts have been made in organic synthesis to synthesize these materials. Although synthetic approaches to making carbohydrates are quite developed, this technique suffers notable difficulties which relate to the selective protection and deprotection steps required in the available synthetic pathways. These difficulties, combined with difficulties associated with isolating and purifying carbohydrates, and determining their structures, has made it essentially impossible for synthetic organic chemistry to economically produce valuable carbohydrates.

Enzyme-mediated catalytic synthesis would offer dramatic advantages over the classical synthetic organic pathways, producing very high yields of carbohydrates (e.g., oligosaccharides and/or polysaccharides) economically, under mild conditions in aqueous solutions, and without generating notable amounts of undesired side products. To date, such enzymes, which include glycosyltransferase, are however difficult to isolate, especially from eukaryotic, e.g., mammalian sources, because these proteins are only found in low concentrations, and tend to be membrane-bound. In addition to being difficult to isolate, the acceptor (peptide) specificity of GalNAc-transferase is poorly understood.

It has been reported that in at least three different proteins the acceptor sites glycosylated by the N-acetylglucosaminyltransferase have a common feature. This feature, which appears to lead to nuclear and cytoplasmic O-GlcNAc structures, is an acidic amino acid followed by serine, proline, and then a run of serines and threonines (Haltiwanger et al., 1990). A more narrowly defined acceptor site has been reported for the proteoglycan xylosyltransferase: the acceptor site for this enzyme consists of acidic amino acids closely followed by the tetrapeptide Ser-Gly-Xaa-Gly, where Xaa may be any amino acid (Bourdon et al. 1987). In spite of attempts to define it either by studying the amino acid sequences surrounding glycosylated serine and threonine residues of known location (Hagopian et al., 1971; Hill et al., 1977; Gooley et al., 1991) or by performing in vitro studies on synthetic peptides (Young et al., 1979; Briand et al., 1981; Hughes et al., 1988; Wang et al., 1992), these studies have yielded little conclusive information. In light of the above-noted considerable value of carbohydrates, there is accordingly a strongly felt need for an improved method for isolation of glycosyltransferase enzyme as well as for studies of the acceptor (peptide) specificity of the enzyme to facilitate its use in carbohydrate synthesis.

INFORMATION DISCLOSURE

Placement of a reference within the following Information Disclosure does not constitute an admission or acknowledgement that the reference constitutes "prior art" to the present application.

Aubert, J. -P., Biserte, G., and Loucheux-Lefebvre, M. -H. (1976) *Arch. Biochem. Biophys.*, 175, 410–418.

Bourdon, M. A., Krusius, T., Campbell, S., Schwartz, N. B., and Ruoslahti, E. (1987) *Proc. Natl. Acad. Sci. USA*, 84, 3194–3198.

Briand, J. P., Andrews, Jr., S. P., Cahill, E., Conway, N. A., and Young J. D. (1981) *J. Biol. Chem.*, 256, 12205–12207.

Bushway, A. A., and Keenan, T. W. (1979) *Biochim. Biophys. Acta*, 572, 146–152.

Carlson, D. M. (1968) *J. Biol. Chem.*, 616, 616–626.

Chen, W., and Bahl, O. P. (1991) *J. Biol. Chem.*, 266, 6246–6251.

Chou, P. Y., and Fasman G. D. (1978) *Ann. Rev. Biochem.*, 47, 251–276.

Cruz, T. F., and Moscarello, M. A. (1983) *Biochim. Biophys. Acta*, 760, 403–410.

Davis, C. G., Elhammer, Å. P., Russel, D. W., Schneider, W. J., Kornfeld, S., Brown, M. S., and Goldstein J. L. (1986) *J. Biol. Chem.*, 261, 2828–2838.

Deschuyteneer, M., Eckhardt, A. E., Roth, J., and Hill, R. L. (1988) *J. Biol. Chem.*, 263, 2452–2459.

Devereux, J., Haeberli, P., and Smithies, O. (1984) *Nucleic Acids Res.*, 12, 387–395.

Domingo, D. L., and Throwbridge, I. S. (1988) *J. Biol. Chem.*, 263, 13386–13392.

Dunphy, W. G., Brands, R., and Rothman, J. E. (1985) *Cell*, 40, 463–472.

Eisenberg, D. (1984) *Ann. Rev. Biochem.*, 53, 595–623.

Elhammer, Å. P, Poorman, R. A., Brown, E., Maggiora, L. L., Hoogerheide, J. G., & Kezdy, F. J. (1993) *J. Biol. Chem.* 268, 10029–10038.

Elhammer, Å. P., and Kornfeld S. (1984) *J. Cell Biol.*, 98, 327–331.

Elhammer, Å. P., and Kornfeld, S. (1986) *J. Biol. Chem.*, 261, 5249–5255.

Fraser, M. J. (1992) *Current Topics Microbiol. Immunol.* 158, 131–172.

Garnier, J., Osguthorpe, D. J., and Robson, B. (1978), *J. Mol. Biol.*, 120, 97–120.

Goldin, A. L., Sandri-Goldin, R. M., Levine, M., and Glorioso, J. C., (1981) *J. Virol.*, 38, 50–58.

Gooley, A. A., Classon, B. J., Marschalek, R., and Williams, K. L. (1988), *Biochem. Biophys. Res. Commun.*, 178, 1194–1201.

Hagopian, A., and Eylar, E. H. (1968), *Arch. Biochem. Biophys.*, 128, 422–433.

Hagopian, A., Westall, F. C., Whitehead, J. S., and Eylar, E. H. (1971), *J. Biol. Chem.*, 246, 2519–2523.

Haltiwanger, R. S., Holt, G. D., and Hart, G. W. (1990), *J. Biol. Chem.*, 265, 2563–2566.

Hanover, J. A., Elting, J., Mintz, G. R., and Lennarz, W. J. (1982), *J. Biol. Chem.*, 257, 10172–10177.

Hardy, M. R., Townsend, R.R., & Lee, Y. C. (1988) *Anal. Biochem.* 170, 54–62.

Hart, G. W., Holt, G. D. and Haltiwanger, R. S. (1988), *TIBS*, 13, 380–384.

Heinrikson, R. L., Sterner, R., Noyes, C., Cooperman, B. S., and Bruckmann, R. H. (1973), *J. Biol. Chem.*, 248, 2521–2528.

Hill, Jr., H. D., Schwyzer, M., Steinman, H. M., and Hill, R. L. (1977), *J.Biol. Chem.*, 252 3799–3804.

Homa, F. L., Otal, T. M., Glorioso, J. C., and Levine, M. (1986), *Mol. Cell. Biol.* 6, 3652–3666.

Homa, F. L., Hollander, T., Lehman, D. J., Thomsen, D., & Elhammer, Å. P. (1993)*J. Biol. Chem.* 268, 12609–12616.

Hsieh, P., and Robbins, P. W. (1984), *J. Biol. Chem.*, 259, 2375–2382.

Hughes, R. C., Bradbury, A. F., and Smyth, D. G. (1988), *Carbohydr. Res.*, 178, 259–269.

Jensenius, J. -C., Andersen, I., Hau, J., Crone, M., and Koch, C. (1981), *J. Immunol. Meth.*, 46, 63–68.

Jentoft, N. (1990), *Trends Biochem. Sci.*, 15, 291–294.

Joziasse, D. H. (1992), *Glycobiology*, 2, 271–277.

Kabsch, W., and Sander, C. (1983), *Biopolymers*, 22, 2577–2637.

Kaushansky, K., Lopez, J. A., and Brown, C. B. (1992), *Biochemistry*, 31, 1881–1886.

Kuroda, K., Geyer, H., Geyer, R., Doerfler, W., and Klenk, H. -D. (1990), *Virology*, 174, 418–429.

Kyte, J., and Doolittle, R. F. (1982), *J. Mol. Biol.*, 157, 105–322.

Laemmli, U. K. (1970), *Nature*, 227, 680–685.

Larsen, R. D., Rajan, V. P., Ruff, M. M., Kukowska-Latallo, J., Cummings, R. D., and Lowe, J. B. (1989), *Proc. Natl. Acad. Sci.*, 86, 8227–8231.

Nagata, Y., Yamashiro, S., Yodoi, J., Lloyd, K. O., Shiku, H., and Furukawa, K. (1992), *J. Biol. Chem.*, 267, 12082–12089.

Nakashima, H., Nishikawa, K., and Ooi, T. (1986), *J. Biochem.*, 99, 153–162.

O'Connel, B., Tabak, L. A., and Ramasubbu, N. (1991), *Biochem. Biophys. Res. Commun.*, 180, 1024–1030.

O'Connel, B., Hagen F., and Tabak, L. A. (1992), *J. Biol. Chem.*, 267, 25010–25018.

O'Connel, B. C., & Tabak, L. A. (1993) *Anal. Biochem.* 210, 423–425.

O'Reilly, D. R., Miller, L. K., & Luckow, V. A. (1992) *Baculovirus Expression Vectors. A Laboratory Manual.*, W. H. Freeman and Company, New York.

Parodi, A. J., Blank, E. W., Peterson, J., and Ceriani, R. (1984), *Mol. Cell. Biochem.*, 58, 157–163.

Paulson, J. C., Beranek, W. E., and Hill, R. L. (1977), *J. Biol. Chem.*, 252, 2356–2362.

Paulson, J. C. (1989), *Trends Biochem. Sci.*, 14, 272–275.

Paulson, J. C., and Colley, K. J. (1989), *J. Biol. Chem.*, 264, 17615–17618.

Piller, V., Piller, F., Klier, G., and Fukuda, M. (1989), *Eur. J. Biochem.*, 183, 123–135.

Piller, V., Piller, F., and Fukuda, M. (1990), *J. Biol. Chem.*, 265, 9264–9271.

Pisano, A, Redmond, J. W., Williams, K. L., & Gooley, A. A. (1993) *Glycobiology* 5, 429–435.

Poorman, R. A., Tomasselli, A. G., Heinrikson, R. L., and Kézdy, F. J. (1991), *J. Biol. Chem.*, 266, 14554–14561.

Prieels, J. -P., Maes, E., Dolmans, M., and Leonis, J. (1975), *J. Biochem.*, 60, 525–531.

Prockop, D. J., Kivirikko, K. I., Tuderman, L., and Guzman, N. A. (1979), *New Engl. J. Med.*, 301, 13–23.

Rodén, L. (1966), *J. Biol. Chem.*, 241, 5949–5954.

Roseman, S. (1970), *Chem. Phys. Lipids*, 5, 270–280.

Roth, J. (1984), *J. Cell Biol.*, 98, 399–406.

Russo, R. N., Shaper, N. L., and Shaper, J. H. (1990), *J. Biol. Chem.*, 265, 3324–3331.

Sadler, J. E. (1984), *Biology of Carbohydrates*, Ginsburg, V., and Robbins, P. W., Eds., Vol. 2, pp. 199–213, John Wiley and Sons, New-York N.Y.

Sanger, F., Nicklen, S., and Coulson, A. R. (1977), *Proc. Natl. Acad. Sci. USA*, 74, 5463–5467.

Sarkar, M., Hull, E., Nishikawa, Y., Simpson, R. J., Moritz, R. L., Dunn, R., and Schachter, H. (1991), *Proc. Acad. Natl. Sci.*, 88, 234–238.

Schachter, H., and Brockhausen, I. (1992), *Glycoconjugates*, Allen, H. J. and Kisailus, E. C., Eds., pp. 263–332, Marcel Dekker Inc. New York, Basel, Hong Kong.

Schmid, K., Hediger, M. A., Brossmer, R., Collins, J. H., Haupt, H., Marti, T., Offner, G. D., Schaller, J., Takagaki, K., Walsh, M. T., Scwick, H. G., Rosen, F. S., and Remold-O'Donnell, E. (1992), *Proc. Natl. Acad. Sci. USA*, 89 663–667.

Scocca, J. R., and Krag, S. S. (1990), *J. Biol. Chem.*, 265, 20621–20625.

Shaper, J. H., & Shaper, N. L. (1992) *Curr. Opin. Struct. Biol.* 2, 701–709.

Sugiura, M., Kawasaki, T., & Yamashina, I. (1982) *J. Biol. Chem.* 257, 9501–9507.

Summers, M. D., and Smith, G. E. (1986), *A manual of methods for baculovirus vectors and insect cell culture procedures.* College Station: Texas Agricultural Experimental Station.

Svenson, E. C., Soreghan, B., and Paulson, J. C. (1990), *J. Biol. Chem.*, 256, 20863–20868.

Tessier, D. C., Thomas, D. Y., Khouri, H. E., Laliberte', F., & Vernet, T. (1991) *Gene*, 98 177–183.

Thomsen, D. R., Post, L. E., and Elhammer, A. P. (1990), *J. Cell. Biochem.*, 43, 67–79.

Thomsen, D. R., Meyer, A. L., & Post, L. E. (1993) in *Insect Cell Culture and Engineering* (Gooosen, M. F. A., Daugulis, A. J., & Faulkner, P., Eds.) pp.105–138, Marcel Dekker, Inc., New York, Basel, Hong Kong.

Tooze, S. A., Tooze, J., and Warren, G. (1988), *J. Cell Biol.*, 106, 1475–1487.

Ulmer, J. B., and Palade, G. E. (1989), *Proc. Natl. Acad. Sci. USA* 86, 6992–6996.

Wang, Y., Abernethy, J. L., Eckhart, A. E., and Hill, R. L. (1992), *J. Biol. Chem.*, 267, 12706–12716.

Wang, X., O'Hanlon, T. P., Young, R. F., and Lau, J. T. Y. (1990), *Glycobiology*, 1, 25–31.

Wang, Y., Agrawal, N., Eckhardt, A. E., Stevens, R. D., & Hill, R. L. (1993) *J. Biol. Chem.* 268, 22979–22983.

Wathen, M., Aeed, P. A., and Elhammer, Å. P. (1991), *Biochemistry*, 30, 2863–2868.

Weinstein, J., Lee, E. U., McEntee, K., Lai, P. -H., and Paulson, J. C. (1987), *J. Biol. Chem.*, 262, 17735–17743.

Wen, D. X., Svenson, E. C., and Paulson, J. C. (1992), *J. Biol. Chem.*, 267, 2512–2518.

Wertz, G. W., Krieger, M., and Ball, A. (1989), *J. Virol.*, 63, 4767–4776.

Wessel, D., & Flugge, U. I. (1984) *Anal. Biochem.* 138, 141–143.

Young, J. D., Tsuchiya, D., Sandlin, D. E., and Holroyde, M. J. (1979), *Biochemistry*, 18 4444–4448.

SUMMARY OF THE INVENTION

The present invention is based upon the discoveries of the gene coding for the enzyme N-acetylgalactosaminyltransferase, the amino acid sequence of the enzyme N-acetylgalactosaminyltransferase, and the polypeptide sequence of the acceptor peptide for the enzyme N-acetylgalactosaminyltransferase. These discoveries allow for the control of glycosylation of a protein.

The present invention involves controlling the glycosylation of a protein, either within a cell or in vitro, by introducing into the DNA sequence encoding the protein at least one gene which is capable of expressing the acceptor peptide for the enzyme N-acetylgalactosaminyltransferase, expressing a protein having an acceptor cite for that enzyme, and exposing the expressed protein to that enzyme.

The present invention also provides a process for altering the glycosylation of a protein produced by a cell where the process involves introducing into the cell at least one gene which is capable of expressing the enzyme N-acetylgalactosaminyltransferase followed by expressing a sufficient amount of the enzyme in the cell to thereby alter the glycosylation of the protein in the cell.

The above discussed and many other features and attendant advantages of the present invention will become better understood by reference to the following detailed description when taken in conjunction with the accompanying drawings.

BRIEF DESCRIPTION OF THE DRAWINGS

FIGS. 2A–2C. N-terminal sequence of bovine colostrum GalNAc-transferase, sequence of oligonucleotide primers, restriction map for cDNA clones (pCR1000-91B and pCR1000-52A) containing the GalNAc-transferase and the sequencing strategy. (A) N-terminal amino acid sequence (34 amino acids) [SEQ ID NO:1] obtained from purified bovine colostrum GalNAc-transferase. The oligonucleotide (oligos A–E) [SEQ ID NOS:2–6, respectively] sequence of the primers and probes used in PCR reactions and Southern blot analysis are shown below the amino acid sequence. The degeneracy of oligonucleotides A, B and C are 512, 64 and 64, respectively. (B) Nucleotide sequence of the region surrounding the EcoRI cloning site of the λgt10 vector. Oligonucleotides F and G [SEQ ID NOS:7 and 8, respectively] were synthesized and used in PCR reactions with the bovine small intestine cDNA library cloned in λgt10 [SEQ. ID NO:16] (see text). (C) Restriction map of cDNA clones pCR1000-91B and pCR1000-52A. The protein coding region of the GalNAc-transferase protein is represented by the open box, the noncoding regions by the straight solid line and vector sequences by a solid box. The arrows beneath the 91B clone and above the 52A clone indicate the direction and extent of sequencing of the clones.

FIGS. 3A and 3B. Amino acid sequence [SEQ ID NO:9] of the cloned GalNAc-transferase inferred from the nucleotide sequence of cDNA clones 91B [SEQ ID NO:10] and 52A. The proposed transmembrane sequence is indicated by the solid boxed residues. Potential sites for N-linked glycosylation are indicated by the dashed boxed residues and predicted sites for O-linked glycosylation are marked with a dot under the appropriate amino acid. The N-terminus of the soluble bovine GalNAc-transferase (determined by N-terminal sequencing) is indicated by the arrow. The consensus poly A+ sequence (AATAAA) is indicated with a solid box and the sequence of the 93 bp insert of pCR1000-93I and the 621 bp insert of pCR1000-600 are indicated by the dashed underline (93I) or solid underline (600). The numbering of the nucleotide (upper) [SEQ ID NO:10] or amino acid sequence (lower) [SEQ ID NO:9] is indicated to the right of the sequence. The first ATG codon obtained from the 91B clone [SEQ ID NO:10] represents the beginning of the 1680 base pair nucleotide sequence for GalNAc-transferase [SEQ ID NO:11]. Genebank accession number L07780.

FIG. 12. The domain structure of bovine UDP-GalNAc:polypeptide, N-acetylgalactosaminyltransferase; construction of the secreted, soluble enzyme. GalNAcT denotes the full-length transferase; the domain structure of the molecule is high-lighted by the symbols described in the key. GalNAcTs denotes the soluble fusion molecule; the melittin signal sequence and 5 amino acids forming the linkage between the signal sequence and the GalNAc-transferase sequence, are represented by the solid bar. The arrow indicates the signal peptidase cleavage site.

FIG. 13. The nucleotide sequence of cloned, re-engineered (to a soluble enzyme) UDP- GalNAc:polypeptide, N-acetylgalactosaminyl-transferase. To express a secreted form of the bovine GalNAc-transferase, the sequences coding for the cytoplasmic and membrane spanning domains of the full-length cDNA (141 nucleotides) were replaced with sequences that code for the honeybee melittin signal peptide and five linker amino acids (78 nucleotides) [SEQ ID NO:18]. The honeybee melittin signal sequence was chosen since the intended expression system for the construct was baculovirus/Sf9 cells.

FIG. 14. Separation of soluble GalNAc-transferase on SDS-polyacrylamide electrophoresis. Silver staining detected only one protein band on the 10% polyacrylamide gel. A molecular mass of approximately 61 kDa could be detected by Coomassie Blue staining.

FIG. 15. The nucleotide sequence of UDP-GalNAc:polypeptide, N-acetylgalactosaminyl-transferase. The depicted nucleotide sequence [SEQ ID NO:11] codes for the enzyme N-acetylgalactosaminyltransferase.

FIG. 16. The amino acid sequence of UDP-GalNAc:polypeptide, N-acetylgalactosaminyl-transferase. The amino acid sequence of the enzyme N-acetylgalactosaminyltransferase [SEQ ID NO:9] is depicted.

FIG. 17. An amino acid sequence of a soluble form UDP-GalNAc:polypeptide, N-acetylgalactosaminyl-transferase. The amino acid sequence of a secreted form of the enzyme N-acetylgalactosaminyltransferase [SEQ ID NO:19] is depicted.

DETAILED DESCRIPTION OF THE PREFERRED EMBODIMENT

Figure 1A:
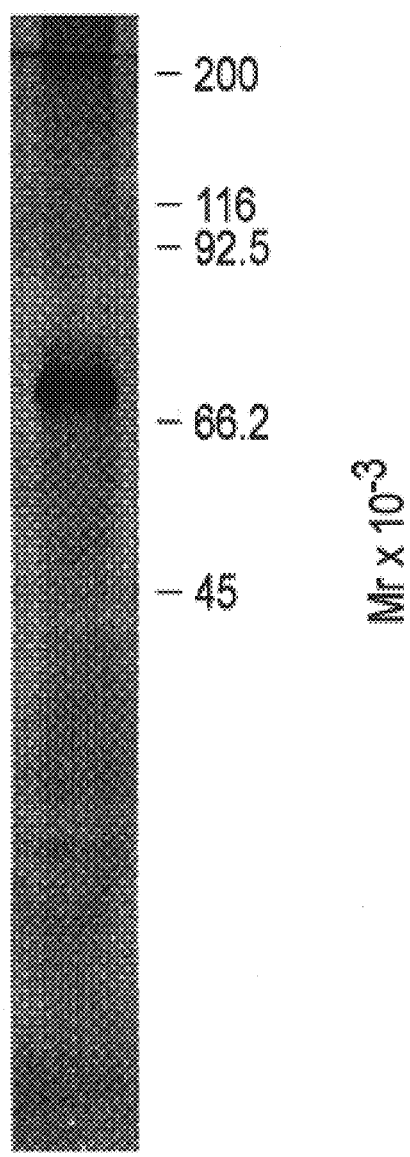
FIGS. 1A and 1B. Separation of bovine colostrum GalNAc-transferase on SDS-polyacrylamide electrophoresis. Panel A: The purified bovine colostrum enzyme separated by SDS-PAGE on a 10% polyacrylamide gel and visualized by silver staining. Panel B: In vitro $^{125}$I-labeled, purified bovine colostrum enzyme visualized by autoradiography. Left lane, products from digestion with peptide N-glycosidase F; right lane, enzyme incubated as for peptide N-glycosidase F digestion but without the glycosidase. The migration of molecular weight markers is indicated to the right.

The term "N-acetylgalactosaminyltransferase (GalNAcT)" as used herein refers to enzymes substantially homologous to, and having substantially the same biological activity as, the enzyme coded for by the nucleotide sequence depicted in FIG. 15 [SEQ ID NO:11] and the amino acid sequence depicted in FIG. 16 [SEQ ID NO:9]. This definition is intended to encompass natural allelic variations in the GalNAct sequence, and all references to GalNAcT, and nucleotide and amino acid sequences thereof are intended to encompass such allelic variations, both naturally-occurring and man-made. Cloned genes of the present invention may code for the GalNAcT enzyme of any species of origin, but preferably code for enzymes of mammalian, most preferably bovine, origin.

The production of proteins such as the enzyme GalNAcT from cloned genes by genetic engineering is well known. See, eg., U.S. Pat. No. 4,761,371 to Bell et al. at Col. 6, line 3 to Col. 9 line 65. (The disclosure of all U.S. patent references cited herein is to be incorporated herein by reference.) The discussion which follows is accordingly intended as an overview of this field, and is not intended to reflect the full state of the art.

DNA which encodes the enzyme GalNAcT may be obtained, in view of the instant disclosure, by chemical synthesis, by screening reverse transcripts of mRNA from appropriate cells or cell line cultures, by screening genomic libraries from appropriate cells, or by combinations of these procedures. Screening of mRNA or genomic DNA may be carried out with oligonucleotide probes generated from the GalNAcT gene sequence information provided herein. Probes may be labeled with a detectable group such as a fluorescent group, a radioactive atom or a chemiluminescent group in accordance with known procedures and used in conventional hybridization assays. In the alternative, GalNAcT gene sequences may be obtained by use of the polymerase chain reaction (PCR) procedure, with the PCR oligonucleotide primers being produced from the GalNAcT gene sequence provided herein. See U.S. Pat. No. 4,683,195 to Mullis et al. and U.S. Pat. No. 4,683,202 to Mullis.

The GalNAcT enzyme may be synthesized in host cells transformed with vectors containing DNA encoding the GalNAcT enzyme. A vector is a replicable DNA construct. Vectors are used herein either to amplify DNA encoding the GalNAcT enzyme and/or to express DNA which encodes the GalNAcT enzyme. An expression vector is a replicable DNA construct in which a DNA sequence encoding the GalNAcT enzyme is operably linked to suitable control sequences capable of effecting the expression of the GalNAcT enzyme in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Vectors useful for practicing the present invention include plasmids, viruses (including phage), retroviruses, and integratable DNA fragments (i.e., fragments integratable into the host genome by homologous recombination). An example of a useful vector is a baculovirus expression vector. The vector replicates and functions independently of the host genome, or may, in some instances, integrate into the genome itself. Suitable vectors will contain replicon and control sequences which are derived from species compatible with the intended expression host. Transformed host cells are cells which have been transformed or transfected with the GalNAcT enzyme constructed using recombinant DNA techniques. Transformed host cells ordinarily express the GalNAcT enzyme, but host cells transformed for purposes of cloning or amplifying the GalNAcT enzyme DNA need not express the GalNAcT enzyme. When expressed, the GalNAcT enzyme will typically be located in the host cell membrane.

DNA regions are operably linked when they are functionally related to each other. For example, a promoter is operably linked to a coding sequence if it controls the transcription of the sequence. A ribosome binding site is operably linked to a coding sequence if it is positioned so as to permit translation. Generally, operably linked means contiguous and, in the case of leader sequences, contiguous and in the same translational reading frame.

Cultures of cells derived from multicellular organisms are a desirable host for recombinant GalNAcT enzyme synthesis. In principal, any higher eukaryotic cell culture is workable, whether from vertebrate or invertebrate culture. However, mammalian and insect cells are preferred. Propagation of such cells in cell culture has become a routine procedure. Examples of useful host cell lines are VERO and HeLa cells, Chinese hamster ovary (CHO) cell lines, and WI138, BHK, COS-7, CV, MDBK and Sf9 cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translation control sequences in expression vectors to be used in transforming vertebrate cells are often provided by viral sources. For example, commonly used promoters are derived from polyoma, Adenovirus 2, and Simian Virus 40 (SV40). The early and late promoters of SV40 are useful because both are obtained easily from the virus as a fragment which also contains the SV40 viral origin of replication. Further, the GalNAcT enzyme promoter, control and/or signal sequences, may also be used, provided such control sequences are compatible with the host cell chosen.

An origin of replication may be provided either by construction of the vector to include an exogenous origin, such as may be derived from SV40 or other viral source, or may be provided by the host cell chromosomal replication mechanism. If the vector is integrated into the host cell chromosome, the latter may be sufficient.

GalNAcT enzyme made from cloned genes in accordance with the present invention may be used for designing new compounds containing oligosaccharides for a variety of healthcare and industrial applications. For example, host cells may be transformed with a vector of the present invention, GalNAcT enzyme expressed in that host, the cells lysed, and the enzyme isolated from the lyzed cells. The enzyme can then be used in vitro to begin the initial reaction in the O-linked oligosaccharide biosynthesis of the transfer of an N-acetylgalactosamine residue from the nucleotide sugar UDP-N-acetylgalactosamine to a serine or threonine residue on the protein acceptor.

Cloned genes and vectors of the present invention are useful in molecular biology to transform cells which do not ordinarily express the GalNAcT enzyme to thereafter express this enzyme. Such cells are useful as intermediates for producing the enzyme. Such cells are also useful for the in vivo biosynthesis of an O-linked oligosaccharide to a protein acceptor.

Milk (and colostrum) contains a number of glycosyltransferase activities (e.g. Prieels et al., 1975; Paulson et al., 1977; Bushway et al., 1979; Parodi et al., 1984). Previous work has shown that bovine colostrum contains what appears to be a soluble form of N-acetylgalactosaminyl transferase (GalNAcT) (Elhammer and Kornfeld, 1986) but did not provide a procedure for the purification of sufficient amounts of GalNAcT for N-terminal sequencing. The following procedure describes the purification of GalNAcT from bovine colostrum. Following collection of sufficient samples, the amino acid sequence of the enzyme is determined by N-terminal sequencing. This information is then used to isolate a cDNA clone encoding a full-length (membrane bound) transferase which upon expression in the insect cell line Sf9 resulted in the synthesis of a fully active enzyme. The acceptor specificity of the enzyme is then determined using a semiquantitative analysis of the amino acids surrounding known glycosylation sites in 16 different proteins followed by in vitro glycosylation studies of synthetic peptides. This work has demonstrated that certain amino acid residues are overrepresented in glycosylated peptide segments and that residues in specific positions surrounding glycosylated serine and threonine residues may have a more marked influence on acceptor efficiency than other amino acid moieties.

The examples which follow are illustrative of specific embodiments of the invention, and various uses thereof. They are set forth for explanatory purposes only, and are not to be taken as limiting the invention.

Materials

The following materials are used in the examples. [($\alpha$-$^{32}$P]dATP (300 Ci/mmol), UDP-[1-$^3$H]N-acetylgalactosamine (8.3 Ci/mmol) and Na[$^{125}$I] (15.2 mCi/$\mu$g) are purchased from Amersham. [$\alpha$-$^{33}$P]dATP is from NEN/Dupont and $^{35}$S-methionine is from ICN (Trans S-35 label, 1 mCi/ml),. Bovine colostrum is obtained from a local farmer. UDP-N-acetylgalactosamine, UDP, PMSF, chymostatin, leupeptin, antipain, pepstatin, aprotinin, bovine submaxillary mucin, Nonidet P-40 (NP-40), Triton X-100, taurodeoxycholate, Sephadex G-100 Superfine, rabbit anti-chicken IgG antibodies, ATP, myelin basic protein, subtilisin, rhodanese and cytochrome C (reduced and carboxymethylated as described by Heinrikson, R. L., 1973) are from Sigma. DEAE-Sephacel, Sepharose 6B and Protein A-Sepharose are from Pharmacia. IODOGEN is from Pierce. Peptide, N-glycosidase F is from Oxford Glycosystems. Geneamp Kit (for PCR) is obtained from Perkin Elmer/Cetus. A bovine small intestine cDNA library cloned in a $\lambda$gt10 vector is purchased from Clontech (catalog # BL1010a). The TA cloning vector pCR1000 is from Invitrogen. Sequenase version 2.0 is from U.S. Biochemical Corp. The baculoGold transfection kit is from PharMingen. 1 cc Bond Elut C$_{18}$ columns were from Varian. Serum-free Grace's insect medium, Insect Express, was from BioWhitaker. The vector pVt-Bac was a gift from Dr. Thierry Vernet at the Biotechnology Research Institute, National Research Council of Canada. *Patella vulgata* $\alpha$-N-acetylgalactosaminidase is from V-Labs, Inc. Restriction enzymes and all other reagents are from standard sources.

In addition, the following buffers are used. Buffer A: 25 mM Imidazole, pH 7.2, 6 mM MnCl$_2$, 30 mM NaCl; buffer B: 25 mM imidazole, pH 7.2, 1 M NaCl, 1% Triton X-100, 20 mM EDTA; buffer C: 25 mM Imidazole, pH 7.2, 30 mM MnCl$_2$, 20 mM NaCl; buffer D: 25 mM Imidazole pH 7.2, 0.5 M NaCl, 20 mM EDTA; buffer E: 25 mM Imidazole, pH 7.2, 10 mM MmCl$_2$, 20% glycerol; buffer F: 25 mM Imidazole, pH 7.2, 30 mM MnCl$_2$, 100 mM NaCl; buffer G: 25 mM Imidazole, pH 7.2, 80 mM NaCl, 0.1% taurodeoxycholate, 10% glycerol; buffer H: 25 mM Imidazole, pH 7.2, 100 mM NaCl, 0.1% Triton X-100, 10% glycerol.

EXAMPLE 1

Isolation of N-acetylgalactosaminyltransferase from Bovine Colostrum

The first four steps in the purification of the transferase are identical to the procedure described by Elhammer and Kornfeld (1986) (which is herein incorporated by reference) except that the samples loaded on the affinity columns are adjusted to 1 mM ATP (in addition to the reported buffer, salt and UDP concentrations) to compensate for an apparently higher pyrophosphatase activity(ies) in the colostrum used. Equilibration, loading, washing and elution buffer volumes are adjusted (scaled up) for the larger columns used. All steps in the purification procedure are performed at +4° C. and enzyme activity is assayed with the following standard assay throughout the purification.

The standard assay for UDP-GalNAc:polypeptide, N-acetylgalactosaminyltransferase activity during purification contained the following components in a final volume of 80 $\mu$l: 50 mM Imidazole pH 7.2, 10 mM MnCl$_2$, 0.5% Triton X-100, 15 $\mu$M UDP-GalNAc, UDP[1-$^3$H-] GalNAc (27,000 cpm/assay), 0.15 mg/ml apomucin and varying amounts of enzyme (see individual experiments). The reaction mixture is incubated at 37° C. for 5–10 minutes (see individual experiments) and the reaction product is TCA precipitated and radioactivity measured as described. Assays for activity in lysates from *Spodoptera frugiperda* cell line 9 (hereinafter referred to as Sf9 cells) are carried out as described by Thomsen et al., (1990).

Step 1: Separation of lipid globules and particles

Crude frozen colostrum obtained from a local farmer is thawed and centrifuged at 15,000 g for 30 minutes. The resulting yellowish lipid layer is removed and discarded. The colostrum is then dialyzed against 20 volumes of buffer A for 16 hours with two buffer changes. The dialyzed material is centrifuged at 100,000 g for 60 minutes. The upper lipid layer is removed and discarded and the clear supernatant is carefully collected. The pellet and fluffy layer at the bottom is discarded.

Step 2: DEAE-Sephacel chromatography

The supernatant from the 100,000 g centrifugation is loaded directly on a DEAE-Sephacel column equilibrated in buffer A. For optimum results, the bed volume of this column should be approximately equal to the amount of 100,000 g supernatant loaded (or ~750 ml/L crude colostrum). The run-through fractions are assayed for GalNAcT, and the fractions with activity are collected and pooled. Typically more than 90% of the applied activity can be recovered after passage through the column.

Step 3: Apomucin affinity chromatography I

The affinity chromatography steps are carried out on apomucin-Sepharose columns with a bed volume of ~60 ml. Apomucin (deglycosylated mucin) is prepared from bovine submaxillary mucin by the method of Hagopian and Eylar with minor modifications. The carbohydrate content of the apomucin preparation is determined by the method of Reinhold. CNBr-activated Sepharose is prepared from Sepharose 6B essentially as described by Cautrecasas. The apomucin is coupled to the activated Sepharose in 0.1 M sodium carbonate buffer pH 9.2 at 4° C. overnight. The protein concentration during the reaction is 2.5 mg/ml. All subsequent steps are carried out as in Affinity Chromatography, Principles and Methods (1979), pp. 15–18, Pharmacia Fine Chemicals, Piscataway, N.J. The coupling efficiency is nearly 100% and the final apomucin-Sepharose contained ~5 mg of bound apomucin/ml sedimented gel.

The columns are run by gravity at a pressure of ~30 cm $H_2O$ during loading and ~60 cm $H_2O$ during washing, elution and regeneration. Before loading, the column is washed with 400 ml buffer B (regeneration buffer) followed by 500 ml buffer C and 150 ml buffer C containing 0.25 mM UDP. Prior to loading the column the sample (~200U enzyme activity per 50 ml column in the first affinity step) is supplemented with $MnCl_2$ and UDP to final concentrations of 30 mM and 1.25 mM, respectively. The column is washed with 4 column volumes of buffer C containing 0.25 mM UDP and six 40 ml fractions are collected. The column is then eluted with buffer D. Due to the specific elution pattern of these columns the eluate is routinely collected as follows: fractions 1 and 2: 25 ml each, normally contains no, or very little activity; fractions 3 and 4: 50 ml each contains the bulk of the activity; fractions 3 and 4: 50 ml each, contains the bulk of the activity; fractions 5 through 7: 25 ml each, contains in some cases smaller amounts of activity. The individual fractions are dialyzed against 4 liters of buffer E (2 changes) immediately after elution, and assayed for enzyme activity. Typically only fractions 3 and 4 are used in the subsequent purification.

Step 4: Apomucin affinity chromatography II

In this step the same type column is used as in the previous one. Before loading, the column is first washed with 400 ml buffer B followed by 500 ml buffer F and 150 ml buffer F, containing 0.25 mM UDP. Prior to running the column, dialyzed fractions 3 and 4 from step 3 are supplemented with 1 M $MnCl_2$, 4 M NaCl and UDP to achieve final concentrations of 30 mM, 100 mM and 1.25 mM respectively. Approximately 600U enzyme activity per run could be located during this step. After loading the sample, the column is washed with 2 column volumes of buffer F followed by two column volumes of buffer F containing 0.5 M NaCl and finally with two column volumes of buffer F containing 1 M NaCl. All the wash buffers contained 0.25 mM UDP. The washes are collected in 40 ml fractions. Elution is then carried out in the same manner as in step 3 but with buffer D containing only 100 mM NaCl. The eluted fractions are dialyzed and assayed for transferase activity as described for step 3.

Step 5: Gel filtration chromatography on Sephadex G-100 superfine

The dialyzed fractions from three step 4 runs are pooled, 1/50 volume 5% taurodeoxycholate is added, and the material is concentrated to 2.5 ml on an Amicon YM-10 filter under 40 psi pressure. Half of this material, 1.25 ml, is loaded on a Sephadex G-100 Superfine column (20–50 μm bead size; 1.5×100 cm) equilibrated in buffer G having 300 mM NaCl. The column is run at a pressure of 30 cm $H_2O$, which resulted in a flow of approx. 2.3 ml/hour and fractions (100 total) are collected at 40 min. intervals and assayed for activity. The fractions comprising the activity peak are pooled and concentrated as described above but without any further addition of detergent. Analytical gel filtration to determine the molecular weight of the transferase is carried out using the same procedure but with a smaller column (0.9×100 cm) and collecting 1.06 ml fractions. The recoveries from this step using the conditions described above typically ranged from 80–90%.

Figure 1B:
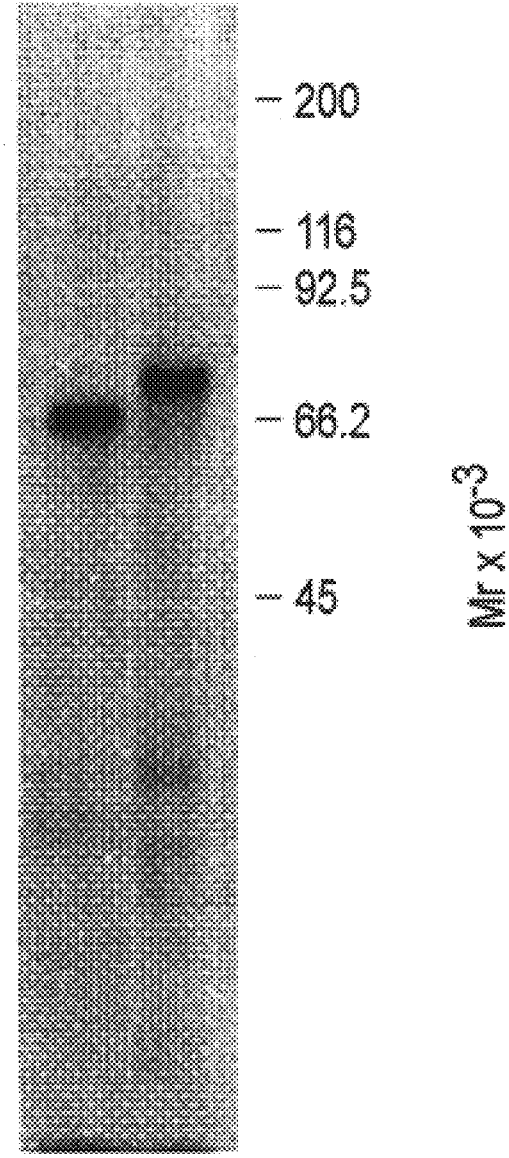

The purified GalNAcT preparation contains only one polypeptide, with a molecular mass of approximately 70 kDa, detectable with silver staining (FIG. 1A). A portion of the purified preparation is labeled in vitro with 125I and separated on SDS-PAGE before and after digestion with peptide N-glycosidase F. FIG. 1B shows that this treatment results in an approximately 6 kDa shift in the apparent molecular mass of the protein.

EXAMPLE 2

N-terminal Sequencing of the Purified Molecule

N-terminal sequencing of the purified bovine colostrum GalNAcT is done by automated Edman degradation in an Applied Biosystems Sequencer (Model 470) fitted with an on-line HPLC analyzer (Model 120-A) for phenylthiohydantoins. Quantitation of the latter is afforded by the Nelson Analytical Turbochrom chromatography data system connected in parallel with the recorder to the output from the HPLC system. The 34 amino acid sequence is shown in FIG. 2A [SEQ ID NO:1].

EXAMPLE 3

Isolation and Characterization of cDNA Clones Encoding Bovine GalNAc-Transferase Oligonucleotide primers are synthesized based on the partial N-terminal amino acid sequence of the purified bovine colostrum enzyme with an Applied Biosystems DNA Synthesizer, model 380B. The oligonucleotide (oligos A–E) [SEQ ID NOS:2–6, respectively,] sequence of the primers and probes used in the Polymerase Chain Reaction (hereinafter referred to as PCR) and later in a Southern Blot analysis are shown in FIG. 2A below the GalNAcT amino acid sequence. The degeneracy of oligonucleotides A, B and C are 512, 64 and 64, respectively. The PCR is carried out in 0.1 ml of solution containing 50 mM KCl, 10 mM Tris-HCL pH 8.3, 1.5 mM MgCl$_2$, 0.2 mM each of the four dNTP's, 11 µM of each oligonucleotide, either 5 µl of the bovine intestine cDNA library or 10 µg of plasmid or λ DNA and 2.5 units of Taq polymerase. The reaction is covered with 0.1 ml of mineral oil and subjected to a temperature step cycle. When degenerate oligonucleotides are used the steps are 94° C. (1 min), 37° C. (2 min), 72° C. (3 min) for a total of 35 cycles. For nondegenerate oligonucleotides the steps are 94° C. (1 min), 55° C. (2 min), 72° C. (3 min) for a total of 25 cycles. Standard DNA manipulations are performed as described in Sambrook, J., Fritsch, E. F., and Maniatis, T. (1989) *Molecular Cloning*.

The cDNA encoding the GalNAcT gene is cloned using the following approach. Oligonucleotides A [SEQ ID NO:2] and C [SEQ ID NO:4] are used as opposing primers in a PCR reaction. A bovine small intestine cDNA library cloned into a λgt10 vector is used as the template for the reaction. On the basis of the amino acid sequence, the predicted size of the amplified PCR product is 93 bp. The products of the PCR reaction are analyzed by Southern blot analysis using oligonucleotide B [SEQ ID NO:3] as a probe (FIG. 2A). Although the PCR reaction yields a number of ethidium bromide staining bands, only a single band of approximately 90 bp hybridizes to the probe. This fragment is gel purified and cloned into the TA cloning vector pCR1000, to yield plasmid pCR1000-93I. Determination of the DNA sequence (FIG. 3) of the pCR1000-93I insert reveals that the deduced amino sequence perfectly matches amino acids 4–34 in the N-terminal sequence of the purified transferase [SEQ ID NO:1] (compare FIG. 2A).

In an attempt to PCR amplify and clone the GalNAcT gene from the bovine λgt10 library, oligonucleotide primers D–G [SEQ ID NOS:5–8, respectively] (FIG. 2A and B) are synthesized. Oligonucleotides D [SEQ ID NO:5] and E [SEQ ID NO:6] are derived from the sequence of the pCR1000-93I insert and F [SEQ ID NO:7] and G [SEQ ID NO:8] are primers that directly flank either side of the EcoRI cloning site of λgt10 (FIG. 2B). PCR reactions are run using the bovine cDNA library as template with oligonucleotides D+F or D+G as primers. The resulting PCR products are analyzed by Southern blot analysis using oligonucleotide E [SEQ ID NO:6] as a probe.

No hybridizing bands are seen in PCR reactions when the D+F primers are used, but the D+G combination yield a single hybridizing fragment of approximately 600 bp.

Figure 3B:
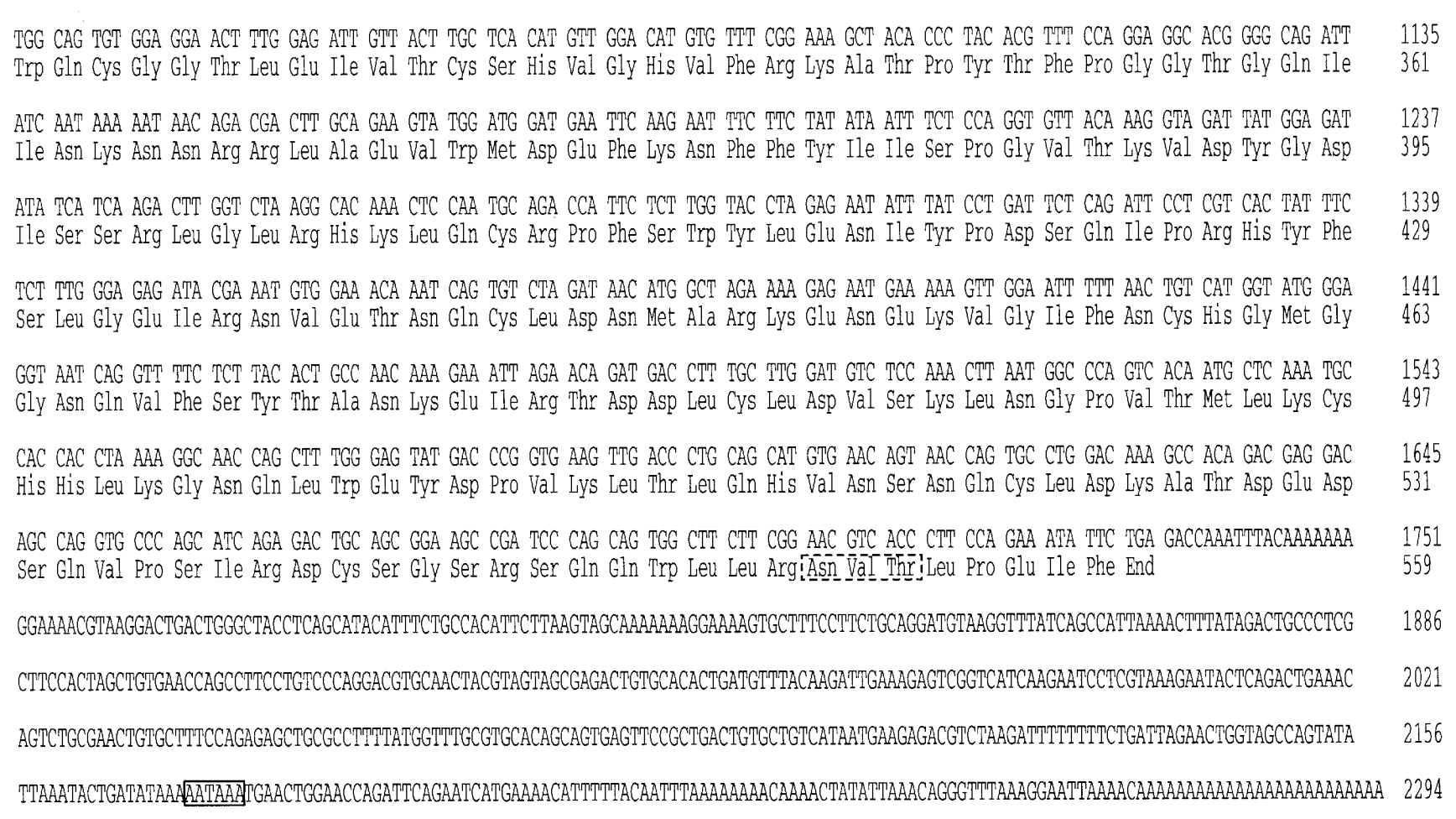

This fragment is gel purified and cloned into the TA cloning vector to yield PCR1000-600 and the sequence of this insert is determined (FIG. 3). The 621 bp insert contains a 207 amino acid open reading frame with the first 23 amino acids of that open reading frame being a perfect match to amino acids 12–34 of the purified protein (FIG. 2A) [SEQ ID NO:1].

Assuming that the 621 bp fragment contains a portion of the GalNAcT gene, this fragment is labeled with [α-$^{32}$P] dATP by nick translation (Goldin et al., 1981) and is used as a probe to screen the bovine cDNA library. The cDNA library (containing 2.5 ×10$^6$ independent clones) is screened by plaque hybridization using the above labeled DNA fragment as a probe. Seven positive plaques are obtained from the primary screen and each isolate is plaque purified three times. Five of the seven isolates are found to contain inserts of 600 bp or smaller while the two remaining isolates contain inserts of approximately 1600 and 2300 bp. The two larger inserts are PCR amplified and cloned (using oligonucleotides F and G as primers) into the TA cloning vector to yield pCR1000-52A (1600 bp insert) and pCR1000-91B (2300 bp insert). The size of the I inserts are analyzed on 1% agarose gels following restriction digest with EcoRI or by PCR using oligonucleotides F and G as primers.

EXAMPLE 4

DNA Sequence Analysis of PCR Inserts and Predicted Amino Acid Sequence

Figure 2C:
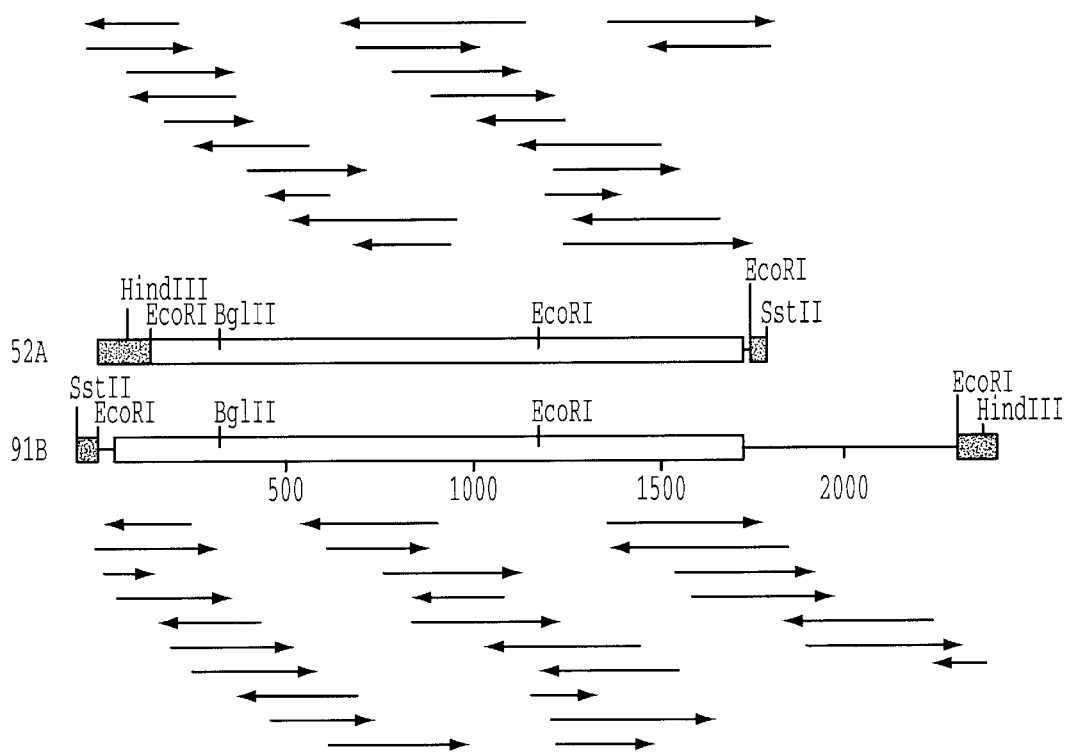

The inserts in pCR1000-93I, pCR1000-600, pCR1000-91B (2294 bp) and pCR1000-52A (1582 bp) are sequenced by the dideoxy chain termination method (Sanger et al., 1977) using Sequenase version 2.0 with [α-$^{33}$P]dATP. Double stranded DNA sequencing (Ausubel et al. 1987) is done with 20-mer oligonucleotide primers, synthesized according to the sequence of the cDNA insert. The sequencing strategy is shown in FIG. 2C. Sequence analysis is performed using the Sequence Analysis software package of the University of Wisconsin Genetics Computer Group (Devereux et al., 1984).

As can be seen in FIG. 3, the first ATG codon of the sequence obtained from the 91B clone is present at nucleotide 53. The translated sequence from the ATG predicts a polypeptide of 559 amino acids [SEQ ID NO:9] with a predicted $M_r$=64,173 which is in good agreement with the $M_r$ for the purified bovine GalNAcT protein (FIG. 1A). The sequence of the 52A clone demonstrated that it is a truncated version of the 91B clone in that the sequence of this clone starts at nucleotide 162 and ends at nucleotide 1744 of the larger 91B clone. The 52A insert covers nearly all of the open reading frame sequences (missing codons for the first 37 amino acids) found in the 91B clone. The nucleotide sequence of the 52A clone is identical to the 91B clone with the exception that nucleotide 358 is a G in the 52A clone instead of an A. This base change is in the wobble position (AGA to AGG) of codon 102 so it does not alter the arginine at that position. The 3'-untranslated region of the 91B clone is 562 bp in length, contains a consensus polyadenylation signal (nucleotides 2176-2182) and a track of 25 A residues at the end of the clone (FIG. 3), indicating that the 91B clone contains all the 3' terminal sequences of the GalNAcT mRNA [SEQ ID NO:10].

Figure 4A:
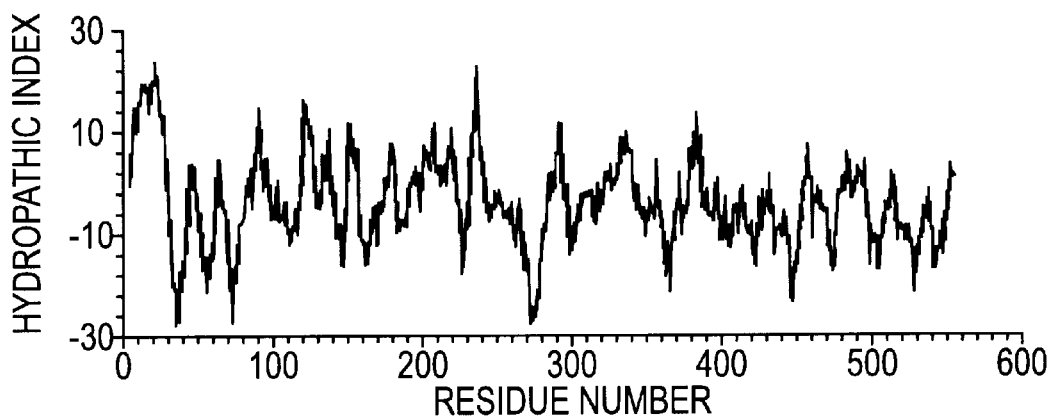
FIGS. 4A and 4B. Predicted transmembrane domain and O-linked glycosylation sites for the cloned GalNAc-transferase. The amino acid sequence of the cloned molecule was analyzed for putative transmembrane segment(s) as described by Kyte and Doolittle (1982) (Panel A) and for O-linked glycosylation sites as outlined by Elhammer et al. (1993) (Panel B).
Figure 4B:
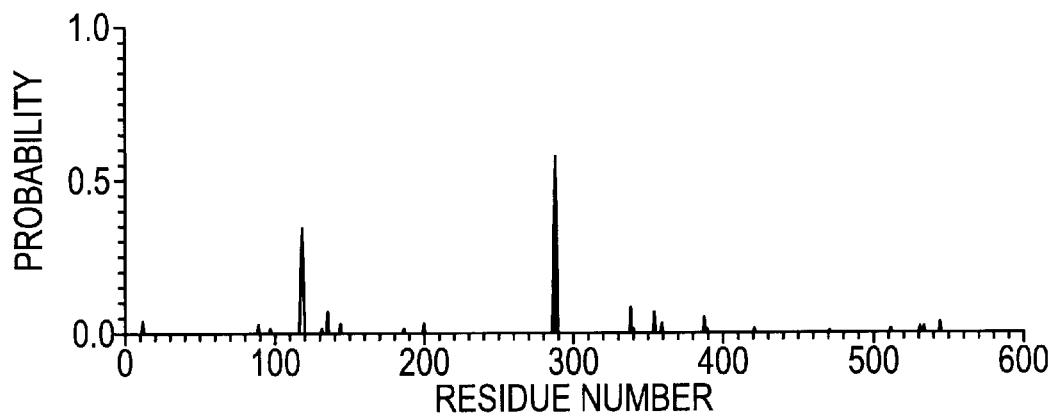

Comparisons of the nucleotide and predicted amino acid sequences of the cloned molecule with the sequences in the GenBank data base and the Swissprot protein sequence data base yielded no significant similarities. Inspection of the predicted amino acid sequence shows that the cloned molecule has the characteristics of a type II membrane protein with the same general domain structure as other cloned gylcosyltransferases (Paulson and Colley, 1989). Also similar is the insignificant sequence homology with other glycosyltransferases as well as with other previously reported sequences. A Kyte-Doolittle hydropathicity analysis (Kyte and Doolittle, 1982) of the molecule resulted in a predicted transmembrane domain between residues #9 and 28 (FIG. 4A); secondary structure analysis suggests that this domain of the molecule has an α-helical conformation (Garnier et al., 1978). Further, the predicted amino acid sequence contains three sites for N-linked glycosylation, asparagines #95, 141 and 552; as well as four predicted (Elhammer et al., 1993) sites for O-linked glycosylation, serine 119 and threonines 117, 118 and 288 (FIG. 4B).

EXAMPLE 5

RNA Isolation and Northern Hybridization

Figure 5A:
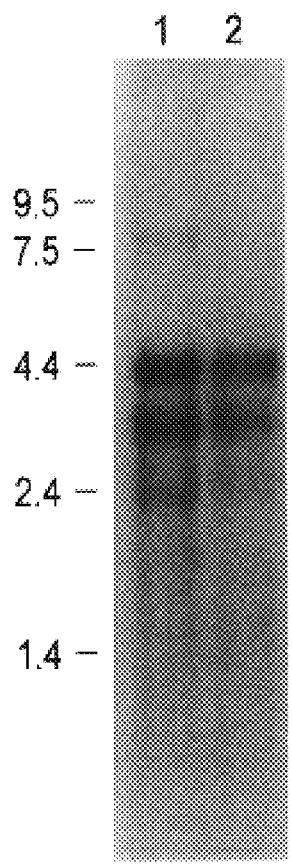
FIGS. 5A and 5B. Northern blot analysis. Two μg of poly A⁺ mRNA isolated from bovine mammary tissue, MDBK cells and 8 different human tissues were probed with the $^{32}$P-labeled, 600 bp insert isolated from the pCR1000-600 (see FIG. 3). (A) lanes 1 and 2 contain mRNA from MDBK cells and bovine mammary tissue, respectively. (B) lanes 1 through 8 contain mRNA isolated from human heart, brain, placenta, lung, liver, skeletal muscle, kidney, and pancreas, respectively.
Figure 5B:
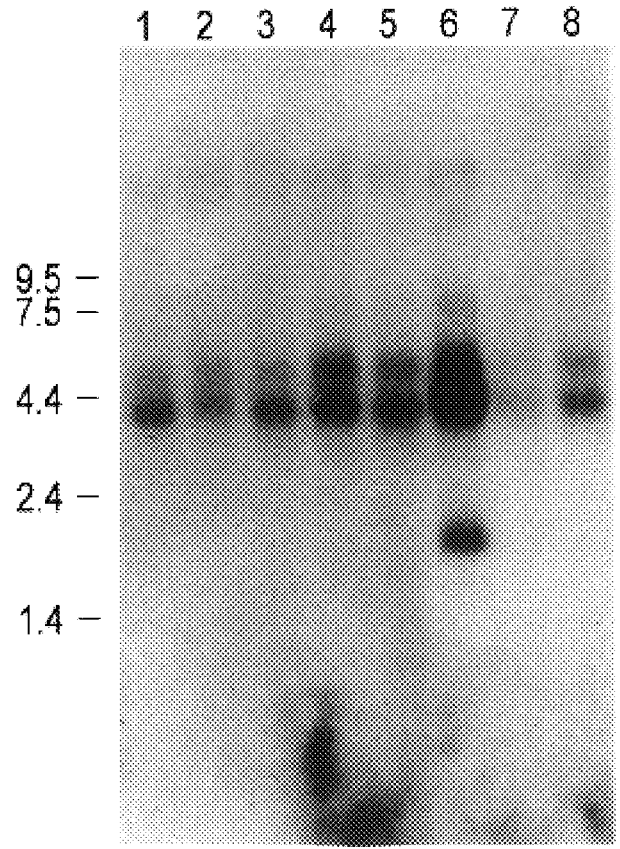

Expression of the GalNAcT mRNA from Madin-Darby bovine kidney cells (hereinafter referred to as MDBK cells)

cells, bovine mammary tissue and various human tissues is analyzed by Northern blot analysis using the 600 bp insert of pCR1000-600 as a hybridization probe. Total RNA and poly A+RNA is prepared from bovine mammary tissue and from MDBK using the Invitrogen Fastrack kit, following the manufacturers procedure. Two µg of poly A$^+$ RNA are denatured by glyoxylation and Northern blot analysis is performed as previously described (Homa et al., 1986). A human multiple tissue Northern blot (Clontech (Cat # 7760-1)) is prehybridized in 50% formamide, 5× SSC, 1× Denhart's, 1% SDS, 100 µg per ml denatured salmon testes DNA, at 42° C. for 2 h and then hybridized overnight at 42° C. with the $^{32}$P-labeled 600 bp insert isolated from the pCR1000-600. Filters are washed three times for 15 min in 0.1× SSC, 0.1% SDS at 55° C. As shown in FIG. 5, at least two different sized GalNAcT mRNA's are detected from all the samples. The size of the bovine messages are approximately 4.1 and 3.2 kb, while all the human tissues express messages of 4.8 and 3.9 kb. In addition, a third mRNA of approximately 1.5 kb is detected in the skeletal muscle sample.

EXAMPLE 6

Expression of the pCR1000-91B Insert in Sf9 Cells

The putative GalNAcT coding region, pCR1000-91B, is digested with SstII and HindIII (both enzymes cut only in pCR1000 sequences that flank the insert; FIG. 2C) and these sites are blunted using T4 DNA polymerase so that it can be cloned into a baculovirus expression vector. BamHI linkers are then ligated onto the blunted ends and the resulting sample is ligated into the BamHI site of the baculovirus expression vector pAC373 (Summers and Smith, 1986). The resulting isolates are screened for proper orientation of the GalNAcT open reading frame with respect to the baculovirus polyhedron promoter, to yield pAC373-GalNAcT. Cotransfection of Sf9 cells with pAC373-GalNAcT and linearized baculovirus DNA from PharMingen's baculoGold transfection kit is performed using calcium phosphate precipitation (Summers & Smith, 1986). The baculovirus DNA provided in the PharMingen transfection kit contains a lethal mutation that can be corrected by homologous recombination with sequences contained in the pAC373 vector. Therefore, following transfection, only recombinant viruses will grow on Sf9 cells. Transfections are done in duplicate and the resulting virus samples are referred to as GalNAcT 2-1A and GalNAcT 2-1B. Cells are harvested 48 hours post infection and lysed in a detergent containing buffer. Following sedimentation of undissolved material, the cleared lysates are assayed for GalNAcT activity. Lysates from uninfected cells or from cells infected with either a baculovirus containing an unrelated gene, CMV-POL (human cytomegalovirus DNA polymerase gene), or two separate baculovirus isolates of the GalNAcT gene, GalNAcT 2-1A and GalNAcT 2-1B, are assayed.

Figure 6:
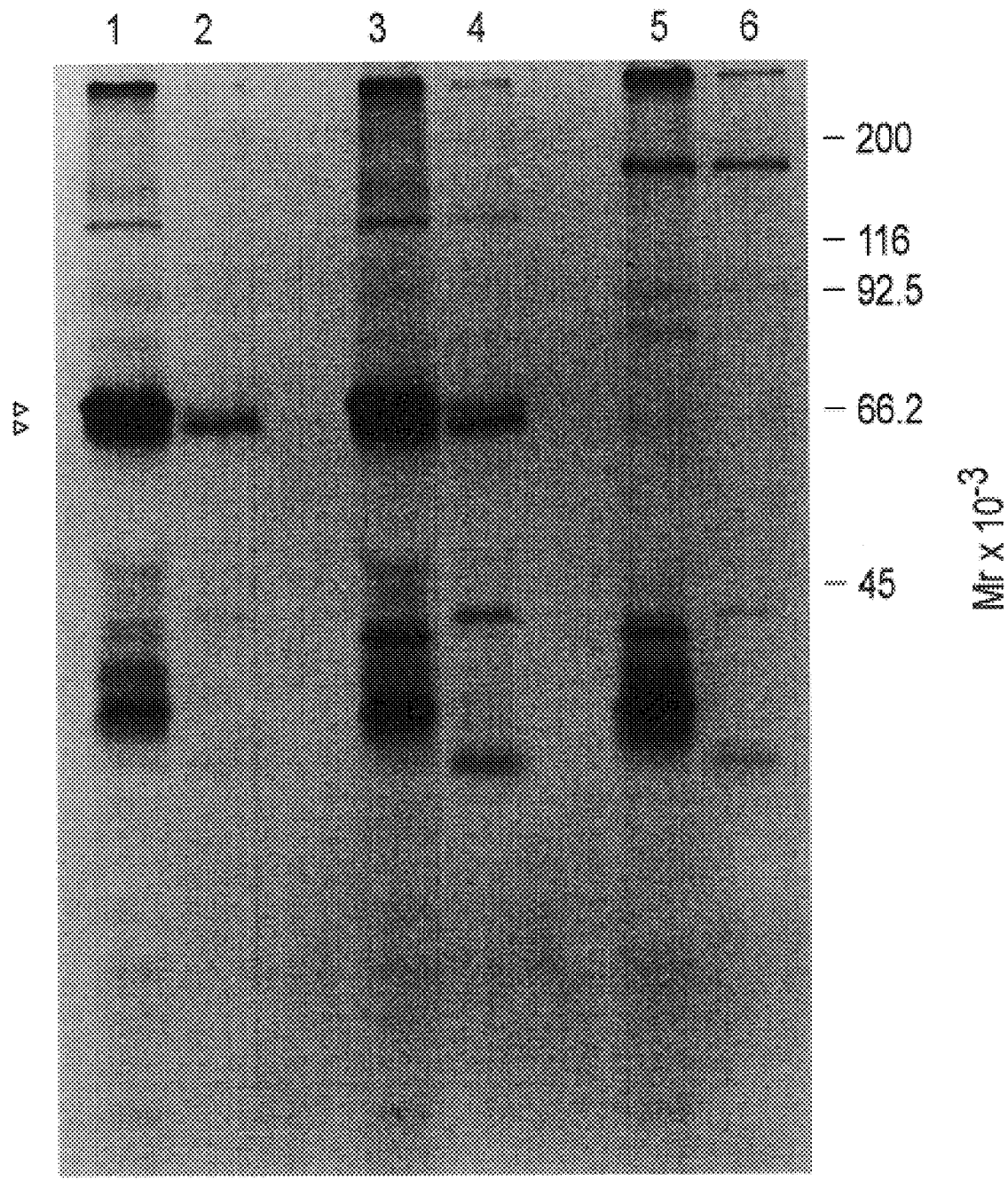
FIG. 6. Immunoprecipitation of in vivo $^{35}$S-methionine labeled GalNAc-transferase expressed in baculovirus infected Sf9 cells. The cloned GalNAc-transferase DNA was expressed in Sf9 cells using a baculovirus vector. The infected cells were switched to culture medium containing $^{35}$S-methionine 24 hours post-infection and harvested after another 24 hours. The cells were lysed in a detergent containing buffer and the labeled transferase was immunoprecipitated from the cell lysates and the corresponding culture media. The washed immunoprecipitates were separated by SDS-PAGE on a 10% polyacrylamide gel. Lanes 1, 3 and 5 contain radioactivity precipitated from cell lysates of cells infected with virus containing the constructs GalNAcT 2-1.A, GalNAcT 2-1.B and CMV Pol-1, respectively. Lanes 2, 4 and 6 contains radioactivity immunoprecipitated from the corresponding culture media. The two molecular mass forms of the immunoprecipitated protein is indicated by the arrow heads. The migration of molecular weight markers is indicated to the right.
Figure 7A:
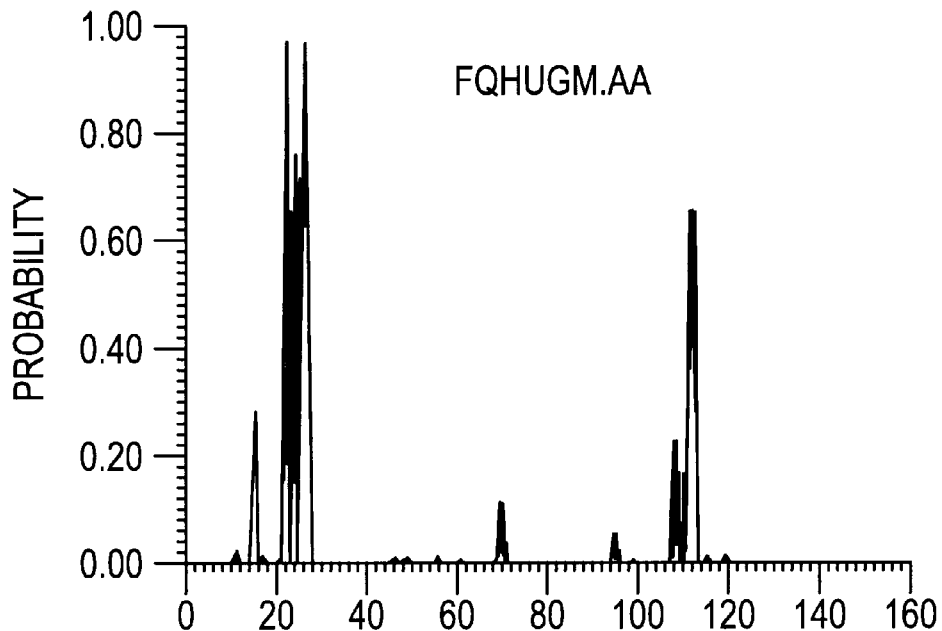
FIGS. 7A–7D. Probabilities of glycosylation. Probabilities were calculated from the amino acid sequence, using Eq 1 and the specificity parameters from Table 5. A: Human granulocyte-macrophage colony-stimulating factor. B: Human choriogonadotropin β-chain. C: Subtilisin BPN'. D: Bovine cytochrome C.
Figure 7B:
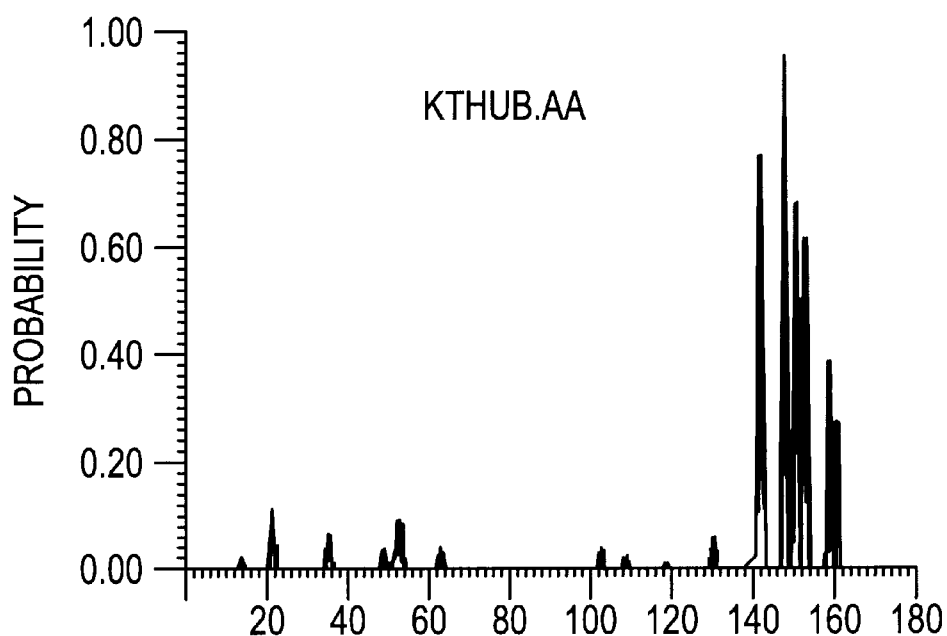
Figure 7C:
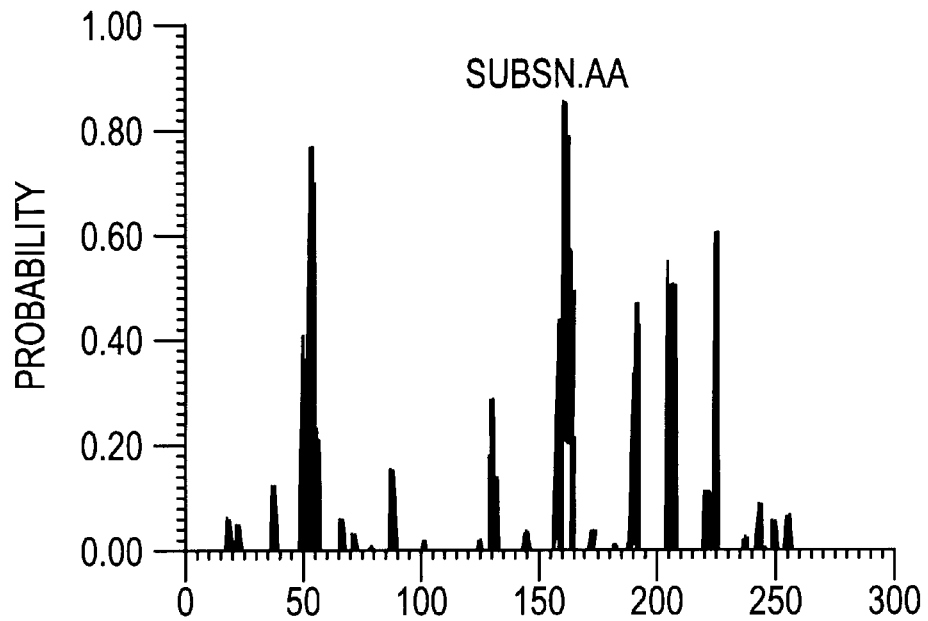
Figure 7D:
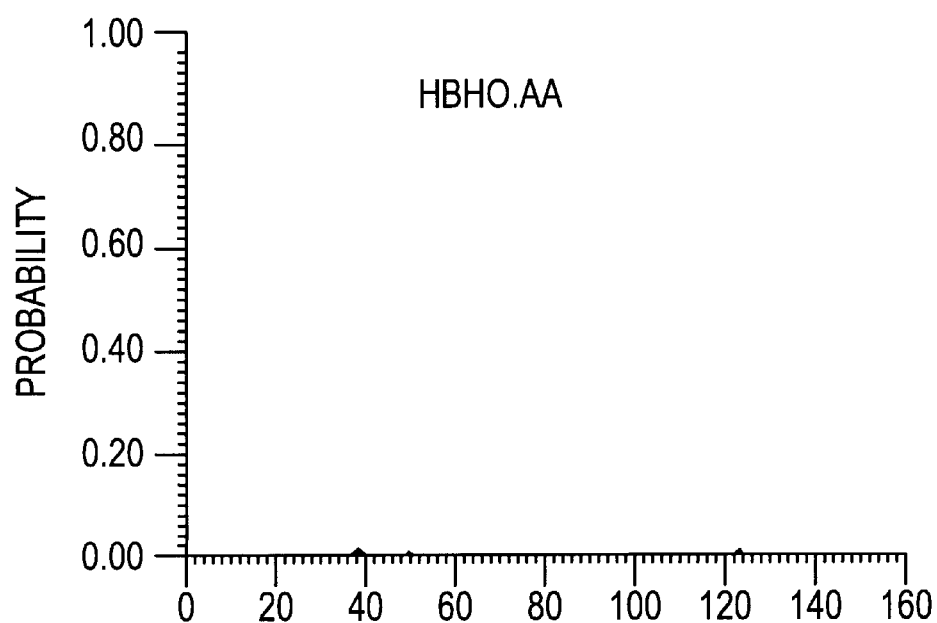

Expression of this construct in Sf9 cells results in an almost 100 fold increase (compared to cells expressing an unrelated protein or uninfected cells) in intracellular GalNAcT activity (Table 1). The marked increase in a protein(s) with a molecular mass similar to that predicted from the amino acid sequence further supports this conclusion (FIG. 6). Increased transferase activity (approximately 4 times) is also detected in the culture medium from the infected cells. Without wishing to be bound to any particular theory, we believe it likely that this represents the intact or a proteolytic fragment(s) of the molecule leaking from dead or dying cells; the total activity in the medium is never more than 4% of the total activity in the cells.

EXAMPLE 7

Immunoprecipitation and SDS-PAGE ANALYSIS OF GalNAc-Transferase

The baculovirus expressed protein is further examined by immunoprecipitation and SDS-PAGE analysis. Baculovirus infected cells are labeled from 24 to 48 hours postinfection with [$^{35}$S]methionine. GalNAcT is immunoprecipitated from lysates and culture media of the labeled cells using a chicken polyclonal antibody raised against the purified bovine colostrum enzyme. A chicken is injected with 100 µg purified enzyme axillary, intramuscularly (with Freund's complete adjuvant). One month later the chicken is boosted with another 50 µg antigen subcutaneously (with Freund's incomplete adjuvant); a second booster, 50 µg enzyme axillary, intra-muscularly, is administered after an additional 21 days. Test bleeds are done two weeks after each booster. After the second test bleed (which upon analysis is found to contain anti-GalNAcT antibodies) eggs are collected each day and used as a source for antibodies. IgG is isolated from egg yolk as described by Jensenius et al., 1981.

Immunoprecipitation of the in vivo $^{35}$S-methionine labeled enzyme, is done from crude cell lysates. Infected cells are labeled between 24–48 hours postinfection with 50 µCi/ml $^{35}$S-methionine in medium that contains one tenth the normal methionine concentration. Approximately 1.5× 10$^6$ labeled, infected cells are dissolved in 670 µl PBS containing 0.5% Triton X-100, 0.5% taurodeoxycholate, 0.05% SDS, 0.1 TIU/ml of Aprotinin and 10 µg/ml each of leupeptin, antipain, chymostatin and pepstatin. Following incubation on ice for >2 hours, any undissolved debris is sedimented at 10,000 × g for 20 minutes and the supernatant is collected. Immunoprecipitation is carried out by the addition of 4 µl (approximately 20 µg chicken IgG) of chicken anti GalNacT antibodies; purified IgG isolated from egg yolk is used for all immunoprecipitation experiments. Following incubation at 4° C. over night, the antigen-antibody complexes are isolated by over night adsorption to 22 µl (volume of sedimented gel) of protein A-Sepharose coated with rabbit anti-chicken IgG antibodies. The coated protein A-Sepharose is prepared by incubating 330 µl sedimented protein A-Sepharose with 2.3 mg rabbit anti-chicken IgG antibodies (an affinity purified IgG fraction) in 1 ml of PBS over night; the coated protein A-Sepharose is washed three times with 1 ml PBS containing 0.5% Triton X-100, 0.5% taurodeoxycholate, 0.05% SDS. Following adsorption of the antigen, the immunosorbent is sedimented by centrifugation and washed extensively essentially as described by Dunphy et al. (1985). The washed antigen-antibody-immunosorbent complexes are suspended in 50 µl SDS-PAGE sample buffer (Laemmli, 1970) and heated for five minutes on a boiling water bath to release the bound antigen. Following sedimentation of the protein A-Sepharose the antigen containing supernatants are aspirated and loaded on SDS-PAGE. SDS-PAGE, and fluorography of the dried gels is done as described previously (Davis et al., 1986) (FIG. 6).

The results from separation of the precipitated material on SDS-PAGE is shown in FIG. 6. Two closely spaced proteins with molecular masses of approximately 67 and 63.5 kDA are detected in both lysates and media from cells infected with viruses containing the GalNAcT gene (FIG. 6). This is close to the molecular mass predicted for the cloned protein and is also comparable to the molecular mass of the purified bovine colostrum enzyme (FIG. 1). The endogenously expressed enzyme is only barely detectable in this experiment but appears to have a similar molecular mass (FIG. 6, lanes 5 and 6); phosphor screen autoradiography of the gel shows that approximately 75 times more radioactivity is incorporated in the cloned enzyme as compared to the endogenous one (Data not shown). The additional lower molecular weight bands seen on the gel probably represents nonspecifically precipitated material since the same bands are found in the control samples (FIG. 6, lanes 5 and 6).

The amino acid sequence [SEQ ID NO:9] predicted for the larger clone isolated provides a plausible explanation for the water solubility of the bovine colostrum GalNAcT. This enzyme apparently lacks the N-terminal 40 amino acids of the membrane bound molecule, a segment which includes both the cytoplasmic and membrane spanning domains. The Kyte-Doolittle hydropathicity plot from the cloned enzyme (FIG. 4A) shows only one sequence segment, residues #9 through 28, with a high membrane spanning probability. It is not clear, at present, if the soluble bovine colostrum enzyme is the result of proteolytic cleavage of a membrane bound molecule or if it represents a bona fide secretory protein. Soluble, enzymatically active forms of a β1–4 galactosyltransferase and a α2-6 sialyltransferase have been reported, both of which appear to be the result of proteolytic cleavage of membrane bound proteins (Paulson and Colley, 1989 and references therein). In addition, the translation products from the different mRNA species related to both these molecules appears in most tissues to be membrane bound molecules (Joziasse, 1992). By analogy it appears likely that the two mRNA's observed in our Northern blotting experiments (FIG. 5) both code for membrane bound enzymes and thus that the soluble bovine colostrum enzyme (again in analogy with β1–4 galactosyltransferase and α2-6 sialyltransferase) must represent a proteolytic fragment of a membrane bound enzyme. On the other hand, work reported on the different transcripts synthesized for rat kidney α2-6 sialyltransferase suggest that some of these molecules contain start codons which when translated would yield proteins without cytoplasmic and membrane anchoring domains (Svenson et al., 1990; Wang et al., 1990; Wen et al., 1992). Clearly, further experiments are needed to positively answer this question.

The larger sizes of the two GalNAcT messages (as compared to the cloned DNA) are presumably related to untranslated sequences larger than those recovered in the isolated clones, in the 5' and/or 3' ends of the native molecules. Messenger RNA molecules from previously characterized cloned glycosyltransferases frequently contain extensive 5' and 3' untranslated sequences (e.g. Weinstein et al., 1987; Larsen et al., 1989; Russo et al., 1990; Scocca et al., 1990; Sarkar et al., 1991; Nagata et al., 1992). There is also a precedence for more than one mRNA species for at least 4 glycosyltransferases; the genes coding for these enzymes appear to be under control of more than one promoter (reviewed by Joziasse, 1992). In addition, a GalNAcT has been described which catalyzes the synthesis of a specific oncofetal epitope on fibronectin (Matsuura et al., 1988; Matsuura et al., 1989). This observation is consistent with the existence of more than one form of the enzyme.

Expression of the cloned sequence in Sf9 cells resulted in a large increase in intracellular transferase activity, thus establishing the identity of the cloned sequence with a GalNAc-to-Ser/Thr transferase. The marked increase in a protein(s) with a molecular mass similar to that predicted from the amino acid sequence further supports this conclusion (FIG. 6). A closer examination of the protein(s) immunoprecipitated in this experiment reveals two closely spaced polypeptide bands with an approximately 3.5 kDa difference in molecular mass. The exact identity of these two proteins is not known at present; they may represent different glycoforms of the enzyme or, perhaps more likely, the lower molecular mass form may be a proteolytic fragment, similar to the enzyme purified from bovine colostrum. The latter possibility is supported by two observations: 1), the mass difference between the two molecules is roughly equal to that of the sequence (40 amino acids) missing in bovine colostrum enzyme and 2), while the immunoprecipitates from cell lysates contains predominantly the higher molecular mass form of the enzyme, the culture medium appears to be enriched in the lower mass form. High-speed centrifugation of the culture medium failed to sediment more than approximately 30% of the enzymatic activity (Data not shown). The smaller molecular mass of the insect cell produced molecule as compared to the predicted mass of a membrane bound bovine enzyme (the molecular mass of the soluble colostrum enzyme plus approximately 4 kDa for the transmembrane and cytoplasmic domains), may be the result of differences in glycosylation of the two molecules.

Insect cells typically synthesize truncated, non-sialylated N- and O-linked oligosaccharides (e.g. Hsieh and Robbins, 1984; Domingo and Throwbridge, 1988; Kuroda et al., 1990; Thomsen et al., 1990; Wathen et al., 1991; Chen and Bahl, 1991); this results in a reduced molecular mass of insect cell produced glycoproteins on SDS-PAGE. The identity of higher molecular mass bands, approximately 120–180 kDa, on the gel is not clear. We have observed these bands previously in immunoprecipitates (by our anti-GalNAc-transferase antibody) from in vivo labeled mammalian and insect cells (Elhammer, unpublished observations). They may represent unspecifically precipitated material, another protein(s) containing an epitope(s) recognized by our polyclonal antibody or aggregated GalNAcT. The latter possibility appears less likely however, since immunoprecipitates of purified GalNAcT contains only one protein band. The fact that the intensity and molecular mass of these bands appears to vary (while the GalNAc-transferase band remains constant) between different experiments and cell types suggest that they represent unspecifically adsorbed contaminants (compare lanes 1–4 and 5–6 in this experiment).

EXAMPLE 8

Construction and Expression in Sf9 cells of a Soluble GalNAc-transferase (GalNAcTs)

In order to express a secreted form of the bovine GalNAc-transferase, the sequences coding for the cytoplasmic and membrane spanning domains of the full-length cDNA were replaced with sequences that code for the honeybee melittin signal peptide (FIG. 12). The honeybee melittin signal sequence was chosen since the intended expression system for the construct was baculovirus/Sf9 cells. It has been demonstrated that use of an insect derived signal peptide often results in increased secretion (as compared to a signal peptide of heterologous origin) of the recombinant molecule when expressed in Sf9 cells (Tessier et al., 1991). The fusion site for the signal peptide was chosen based on the N-terminal sequence of the soluble colostrum enzyme.

The plasmid pAC373-GalNAcT (Homa et al., 1993) which contains the full length GalNAc-transferase gene under the control of the baculovirus polyhedron promoter was digested with XbaI and BglII, which generated a 150 bp fragment, and with BglII and XhoI, which generated a 9700 bp vector fragment. Both fragments were gel purified. The XbaI site used is located 7 amino acids from the N-terminus of the soluble colostrum enzyme, in a portion of the molecule corresponding to what is referred to as the "stem region" in other glycosyltransferases (reviewed by Shaper & Shaper, 1992). Soluble forms of several glycosyltransferases are generated by proteolytic cleavages in this region. Consequently, it is believed to be unimportant for catalytic activity (Joziasse, 1992; Shaper & Shaper, 1992).

pVT-BAC (Tessier et al, 1991), which contains the coding sequences of the honeybee melittin signal peptide, was digested with SmaI and a 12 bp XbaI linker was ligated onto the SmaI site. The sample was then digested with XbaI and XhoI and the 2100 bp fragment generated by this digest was gel purified. The three gel purified fragments were added to the same tube and ligated. The resulting plasmid contains a GalNAc-transferase gene under the control of the baculovirus polyhedron promoter in which the first 47 amino acids (141 nucleotides) have been replaced with 21 amino acids (63 nucleotides) of the honeybee melittin signal peptide plus five (5) amino acids (15 nucleotides) that link the two domains together (FIG. 13) [SEQ ID NO:18]. This construct, pAC373-GalNAcTs-Mel, was then used to prepare a recombinant baculovirus that expresses a secreted form of GalNAc-transferase, GalNacTs, using the BaculoGold transfection kit (Summers & Smith, 1986; Homa et al, 1993)(FIG. 17)[SEQ ID NO:19].

GalNAcTs was routinely expressed in one liter batches. Approximately 1×10$^9$ cells in one liter Grace's serum-free insect medium (Insect Express) were infected with 5 pfu/cell of GalNAcTs-Mel. The infected cells were cultured in shaker flasks for 65 hours before harvest. Expression of the construct GalNAcTs-Mel in Sf9 cells resulted in 130-fold increase in GalNAc-transferase activity in the culture medium, as compared to uninfected cells (Table 2) or cells infected with an unrelated molecule (α6-3). This is more than 35 times the amount recovered in the medium of cells expressing the full length molecule (Homa & Elhammer, unpublished observations). A significant portion (36%) of the total enzymatic activity resulting from expression of the soluble molecule was, however, retained inside the cells; the reason for this is not clear at present.

EXAMPLE 9

Isolation and Characterization of GalNAcTs

Purification of the soluble molecule was accomplished in one step, by chromatography on apomucin-Sepharose. The procedure used for the purification of the recombinant enzyme was a modification of the second affinity chromatography step in the purification of the bovine colostrum enzyme (Elhammer & Kornfeld, 1986). The affinity column used for purification of the recombinant enzyme was prepared as described (Elhammer & Kornfeld, 1986). Total bed volume was approximately 200 ml; ligand density was approximately 3.5 mg/ml gel. Before each separation run the column was washed with 1000 ml Buffer B and equilibrated with 1000 ml Buffer F followed by 420 ml Buffer F containing 0.25 mM UDP. Crude conditioned cell culture medium was fractionated on this column in 1 liter batches as follows.

The medium was first dialyzed against 25 mM Imidazole, pH 7.2, 100 mM NaCl, 30 mM MnCl$_2$ with three buffer changes. Following centrifugation at 12,000× g for 20 minutes to remove precipitated material (no enzyme activity was lost in this step), the dialyzed medium was supplemented with UDP to 1.25 mM and loaded directly on the affinity column; the column run-through was collected in five 200 ml fractions. The column was then washed sequentially with 500 ml buffer F, 250 ml Buffer F containing 0.2% Triton X-100, 250 ml Buffer F and 250 ml Buffer F containing 1.0 M NaCl. All wash buffers contained 0.25 mM UDP and washes were collected in 250 ml fractions. The bound enzyme was eluted from the column with 720 ml Buffer D and collected in seven 80 ml fractions. Run-through, wash, and eluted fractions were all dialyzed against Buffer E containing 300 mM NaCl (three changes) prior to assay for GalNAc-transferase activity. The recovery of enzyme activity on the column was invariably over 90%. The following concentration of the eluted enzyme, however, led to significant losses in activity. In fact this step accounted for the largest losses in the preparation procedure. Dialyzing the enzyme into a buffer containing 300 mM NaCl prior to concentration was an absolute necessity to avoid even higher losses in this step. The enzyme isolated from bovine colostrum shows a similar behavior in this regard (Elhammer & Kornfeld, 1986). The purified preparation was concentrated by ultrafiltration on a YM-10 membrane at 45 psi pressure.

The purified, concentrated preparation, together with an aliquot of the crude conditioned cell culture medium, was analyzed on SDS-PAGE essentially as described by Laemmli (1970). The crude medium sample was precipitated as described by Wessel and Flugge (1984) prior to electrophoresis; precipitate corresponding to approximately 250 µl medium was loaded. NH$_2$-terminal sequencing of the purified molecule was done as described in Example 2. Interestingly, this purification procedure yielded a homogenous preparation only if expression of the molecule was carried out in serum-free medium. Preparations from serum containing medium appeared homogenous on SDS-PAGE but N-terminal sequencing and separation on capillary electrophoresis revealed that they, in addition to GalNAc-transferase, also contained considerable amounts of bovine fetuin (Data not shown). Consequently the purified enzyme characterized herein was isolated from material produced in serum-free medium.

The amino acid composition of the purified GalNacTs was determined by automated ion-exchange chromatography on a Beckman amino acid analyzer (Beckman 6300) and was found to correspond with the composition predicted from the nucleic acid sequence shown in FIG. 3 [SEQ ID NO:9]. Samples were hydrolyzed for 24 hours in vacuo at 110° C. in 6N HCl. Dried hydrolysates were dissolved in buffer at pH 2.2 (NaS; Beckman) prior to application to the analyzer. Quantitation of the latter was afforded by the Nelson Analytical Turbochrom chromatography data system connected in parallel with the recorder to the output of the dual-channel spectrophotometer. NH$_2$-terminal sequencing of the purified, concentrated enzyme demonstrated that the melittin leader sequence was cleaved from the molecule at the predicted site (FIG. 12). Furthermore, only one sequence was detected in the preparation, consistent with an essentially pure enzyme preparation. The purity of the enzyme was also investigated on SDS-PAGE. As can be seen in FIG. 14, only one band, with a molecular mass of approximately 61 kDa, could be detected by Coomassie Blue staining. Silver staining also failed to detect more that one protein band on the gel and separation of the purified enzyme on capillary electrophoresis resulted in only one UV absorbing peak eluting at a position consistent with the molecular mass of approximately 61 kDa (Data not shown).

EXAMPLE 10

Statistical Analysis of the Peptide Acceptor For GalNAc-Transferase

The efficient production of the cloned molecule using the baculovirus expression system facilitated preparation of GalNAc-transferase in amounts sufficient for detailed biochemical and enzymatic studies to determine the acceptor substrate specificity of GalNAc-transferase from a database of in vivo substrates and from the in vitro glycosylation of proteins and peptides. These studies have been facilitated by the availability of information regarding the presence of glycosylated serine and threonine residues in proteins obtained during protein sequencing. This information is registered in the NBRF protein sequence repository. Cursory inspection of the amino acid sequences surrounding these reactive Ser and Thr residues revealed that the enzyme must have a broad specificity and that there is no unique, readily identifiable amino acid sequence associated with enzymatic specificity. Indeed, the enzyme is even capable of glycosylating N-terminal and C-terminal Ser or Thr residues, which indicates that the specificity cannot be limited to one or two specific subsites flanking the reactive hydroxyamino acid.

Recently, a statistical method for analyzing the broad specificity of enzymes which act on protein segments through extended multisite attachment has been developed and applied with some success to determine the specificity of the HIV-1 protease (Poorman et al. 1991). The number of reported sequences surrounding glycosylated Ser and Thr residues was large enough to warrant their analysis by this statistical method. This approach was used to outline the crucial features of the peptide acceptor for GalNAc-transferase. The validity of this information was then determined in a series of experiments involving in vitro glycosylation of both synthetic and naturally occurring substrates. The results indicate that both serine and threonine residues can be glycosylated by the same enzyme and that the broad specificity of GalNAc-transferase is the consequence of an extended binding site.

A search of the NBRF protein database yields several hundred definite or probable Thr and Ser O-glycosylation sites. From these, only those with reasonably unambiguous assignments are chosen and all proteoglycans are excluded since they contain primarily glycosaminoglycan chains where the anchoring sugar is xylose and not GalNAc. Also included into the reference set are the O-glycosylation sites identified in some recently analyzed glycoproteins. In the case of proteins listed for several different species, homologous proteins are included only when the glycosylation sites themselves show no homology. The complete reference set consists of the 196 glycosylated peptide segments (shown in Table 1 in Elhammer et al., 1993). The glycosylated peptides are listed as enneapeptide (ennea Greek, nine) segments, with the reactive Ser or Thr in the central position, designated as P0. Accordingly, the amino acid side chains toward the N-terminus are designated as the subsites P1 to P4 and those toward the C-terminus as subsites P1' to P4'. A length of nine residues is chosen as a starting point, with the option that, depending on the results on the selectivity of the subsites, the portion of the peptides subject to analysis may be extended or truncated. The sequences show that besides the obvious need for Ser or Thr in P0, no other subsite has an absolute requirement for any given amino acid. This then suggests that specificity of the enzyme may be the result of the cooperation of several subsites, none of them essential, but all of them contributing to catalytic efficiency.

In order to explore whether the cooperative-subsite model is a valid description of GalNAc-transferase, the standard set of peptides is analyzed according to the method applied with some success to the specificity of the HIV-1 protease (Poorman et al. 1991).

In brief, the frequencies of individual amino acids at each subsite are compared (Table 3) to those expected on the basis of their abundance in a reference set of globular proteins (Nakashima et al. 1986). Table 4 shows that Ser, Thr, and Pro are significantly surabundant in almost all positions. Specificity parameters, $s_{i,j}$—defined as the observed abundances divided by the abundances expected for globular proteins—are calculated from these data; they are listed in Table 5. It has been shown (Poorman et al. 1991) that if the enzyme has independent subsites then the probability, h, that any Ser or Thr-containing enneapeptide will react with the enzyme can be calculated from the equation:

$$h = \frac{RP}{RP + \frac{1}{PS}} \quad \text{Eq. 1}$$

where PS is the abundance of glycosylatable peptides in all proteins and RP is the cumulative probability calculated as the product of all relevant $s_{i,j}$ values:

$$RP = \prod_{i=1}^{9} s_{i,j} \quad \text{Eq. 2}$$

Using this algorithm, a Ser or Thr-containing peptide may be predicted to be a substrate for the enzyme if the probability, h, is higher than a certain cutoff value, $h_c$. In order to achieve the best compromise between overpredictions and underpredictions, PS and $h_c$ are iteratively optimized using the proteins in the Kabsch-Sander database (Kabsch and Sander 1983), as described (Poorman et al. 1991). It is found that the best compromise is reached with $PS=\frac{1}{56} h_c=0.19$, resulting in a 21.4% underprediction in the reference data set. Thus, a given peptide is predicted to be a glycosyl acceptor, if $$h = \frac{\prod_{i=1}^{9} s_{i,j}}{56 + \prod_{i=1}^{9} s_{i,j}} \geq 0.19 = h_c$$

Overprediction is expected to be variable and in some cases may be rather high since glycosylation of a fully folded protein presumably requires not only the proper local primary structure but also accessibility from the aqueous environment. For example, applying the predictive algorithm to human granulocyte-macrophage colony-stimulating factor (fqhugm.aa, FIG. 7A), it is found that the four experimentally observed O-glycosylation sites are correctly predicted at sequence positions 22, 24, 26, and 27 (Kaushansky et al. 1992) but four additional sites are also predicted: $Ser_{15}$ (h=0.29), $Thr_{108}$ (h=0.24), $Thr_{111}$ (h=0.66), and $Ser_{112}$ (h=0.66). Similarly, human choriogonadotropin P chain (kthub.aa, FIG. 7B) yields one underprediction, $Ser_{138}$ (h=0.01) and one overprediction at $Thr_{160}$ (h=0.28). The probability pattern of these two proteins is shown in FIG. 7. It is interesting to note that the calculated probabilities for these two proteins are not distributed uniformly between the two extremes. Rather, a small number of residues are associated with very high probabilities whereas the rest of the sequence indicates uniformly low probabilities. Furthermore, the residues with high probabilities are clustered into one or two distinct segments where the clustering of Ser and Thr residues may perhaps be a necessary but certainly not a sufficient criterion for creating a highly glycosylated protein segment.

Taken together, these observations suggest that glycosylation is determined as much by the specificity of the enzyme toward a given sequence of amino acids surrounding the reactive residue as by the exposure of this peptide chain to the aqueous environment. This inference is further strengthened by the distribution of potential glycosylation sites in the Kabsch/Sander proteins, none of which are glycosylated in vivo. For example, subtilisin BPN' (subsn.aa, FIG. 7C) which is produced by a microbial system incapable of O-linked oligosaccharide biosynthesis, contains a number of randomly distributed potential glycosylation sites, while very few nonglycosylated mammalian proteins contain any potential glycosylation sites. It is perhaps more typical to find no potential glycosylation sites at all, as in the case of horse hemoglobin (hbho.aa) or that of bovine cytochrome C (ccpg.aa, FIG. 7D).

Figure 8A:
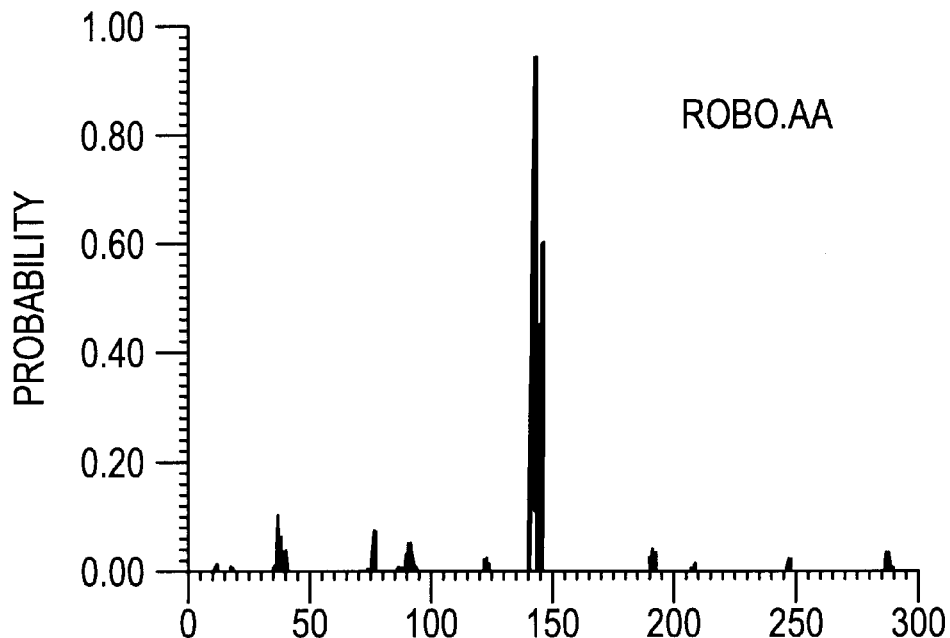
FIGS. 8A–8D. Probabilities of glycosylation. Probabilities were calculated from the amino acid sequence, using Eq 1 and the specificity parameters from Table 5. A: Bovine rhodanese. B: Chimeric protein constructed from the first two domains of human CD4 and the last three domains of *Pseudomonas exotoxin*. C: Human LDL receptor protein. D: Human Alzheimer amyloid protein precursor.
Figure 8B:
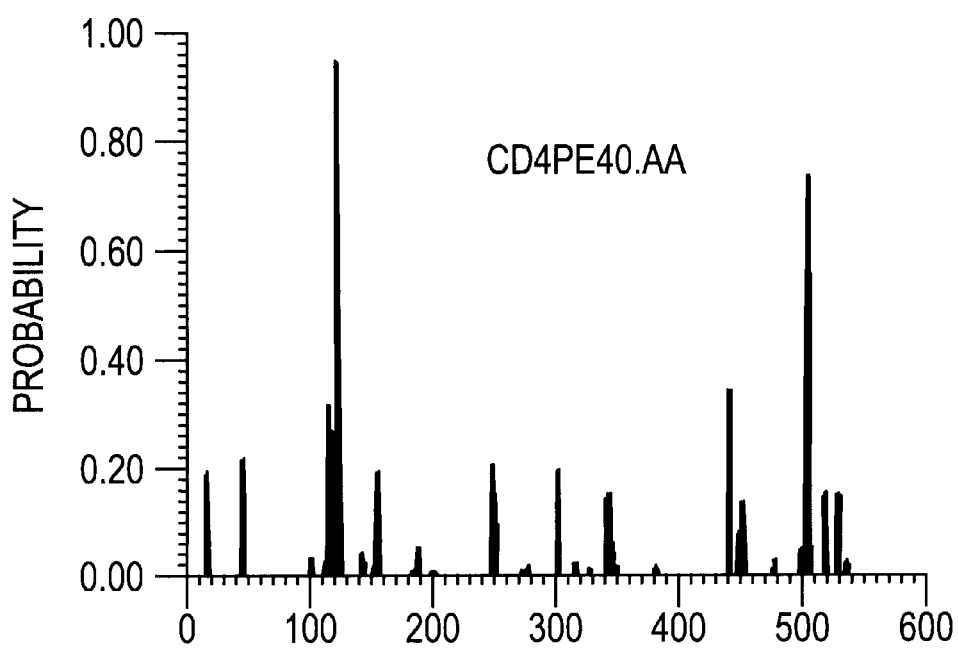
Figure 8C:
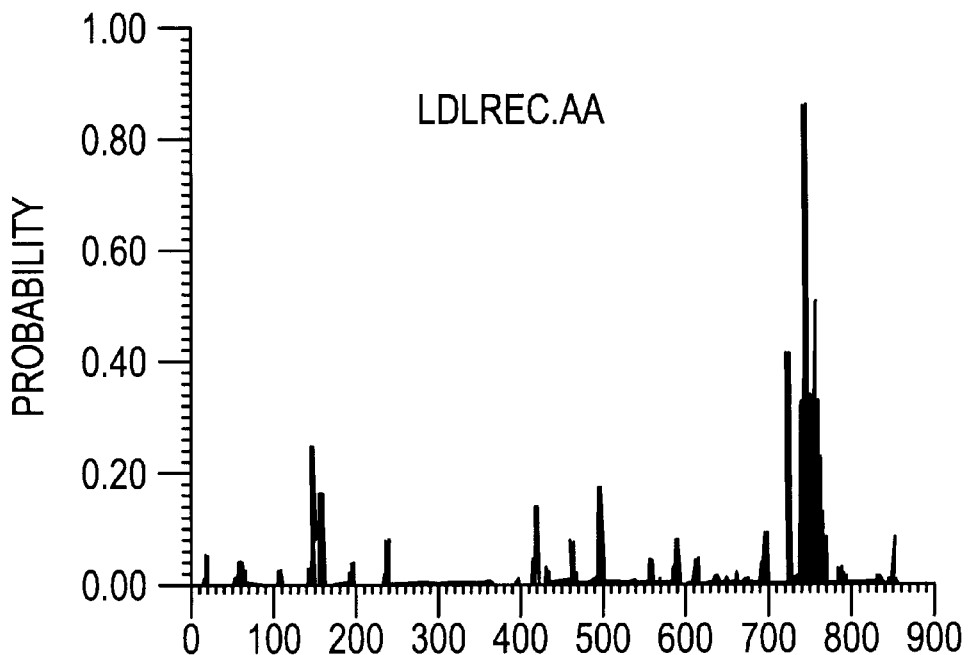
Figure 8D:
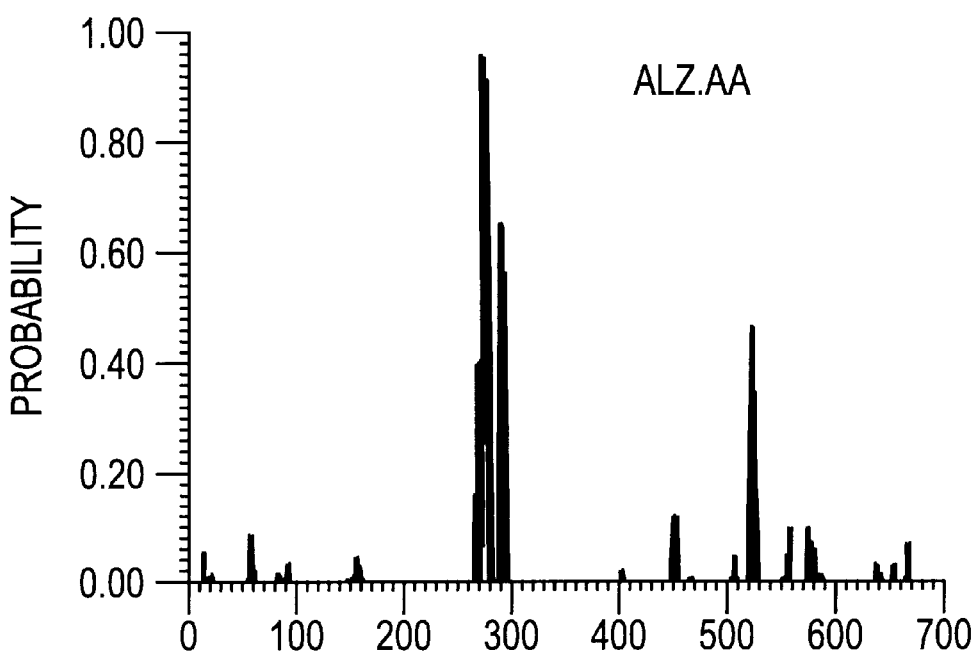

It appears as if the sequence of mammalian proteins which are not destined to be glycosylated are in fact selected against containing potential glycosylation sites. On the other hand, according to current understanding of the intracellular topology of the GalNAc-to-serine/threonine transferase, the amino acid sequence of a cytoplasmic protein would not be selected against having potential glycosylation sites for the anchoring of mucin type oligosaccharides. For example, it is found that bovine rhodanese (robo.aa, FIG. 8A) does contain three strong glycosylation sites at $Thr_{141}$ (h=0.95), $Ser_{142}$ (h=0.49), $Ser_{145}$ (h=0.61), see FIG. 8. Since this region of the protein consists of a fully exposed segment linking the two homologous domains of the enzyme, exposure of native or mildly denatured rhodanese to GalNAc-transferase should result in glycosylation of the molecule. Similarly, the chimeric protein, CD4PE40, constructed from two domains of the human CD4 protein and three domains of the *Pseudomonas exotoxin*, shows two prominent potential glycosylation sites, both at regions linking individual domains, see FIG. 8B. In the same vein, one would predict that subtilisin could also be extensively glycosylated, if not in the native form then at least after mild denaturation.

The potential of the predictive method is perhaps best illustrated by its application to the LDL receptor (ldlrec.aa, FIG. 8C) and the Alzheimer precursor protein (alz.aa, FIG. 8D), which have both been shown to be extensively O-glycosylated, each in a known, narrow segment of the polypeptide. As shown in FIG. 8, the present method not only correctly identifies these regions of glycosylation but also specifically predicts which Ser and Thr residues may be modified.

The above analysis allows one to hypothesize about the salient features of the enzyme active site responsible for the specificity of glycosylation. Table 4 indicates that high selectivity is expressed at all subsites, but only toward Ser, Thr, and Pro. The selectivity of a given subsite depends on how many times more frequent are at that site the surabundant residues than all the other amino acids. Also, selectivity is higher when the surabundant residue is one which occurs with low frequency in globular proteins. To quantitate the selectivity, one defines a specificity parameter for the subsite i, $S_i$, as the number of surabundant residues found at that site, divided by the number of these same residues expected at that site from random distribution. This ratio is then multiplied by the fraction of surabundant residues at that site. The values of $S_i$, reported in Table 3, suggest that the binding site extends at least from P3 to P4' and perhaps even P4 is included in the substrate-enzyme interactions.

Besides the three specific amino acids, no other amino acid is found in surabundance at any site, although Gly, Ala, Val, and Met are permitted to occur randomly, as indicated by their $s_{i,j} \approx 1$, see Table 5. Perhaps more important is the fact that Asp, Asn, Arg, Tyr, Leu, Phe, Lys, Cys, and Trp occur only at very low frequencies and their presence at any site strongly decreases the probability of glycosylation. In other words, neither strongly hydrophobic nor strongly hydrophilic residues (see consensus hydrophobicity scale, Eisenberg 1984) are recognized by the glycosyltransferase. If a single intrinsic property of the amino acid side chains— such as hydrophobicity, size, surface, electric charge, etc—is responsible for the specific interaction with the active site, then $s_{i,j}$ should depend critically on that property. Attempts to correlate the $s_{i,j}$ distribution with a variety of parameters possibly characterizing the individual amino acids met with little success. Most importantly, no correlation has been found with a parameter predicting β-turns, although such a correlation has been inferred for xylosyltransferase (M. A. Bourdon et al., 1987).

The question of whether any positive or negative cooperativity could exist between specific amino acid side chains at any two subsites has also been explored. For this purpose, in a series of trials the amino acids in the reference peptide set are randomized within each subsite in turn. Any positive or negative cooperativity between subsites should disappear in the randomized set and one would observe a significant change in the distribution of h values. Only random fluctuations are in fact observed, thereby indicating the absence of any strong cooperativity. In other words, the subsites behave as if they are independent of the presence of specific amino acids at any other subsite.

The possibility still remained that the enzyme would recognize a specific secondary structure of the target enneapeptide and that this secondary structure would be induced not by the cooperative action of several constituent amino acids but by their intrinsic tendency to form a given secondary structure. In order to test this possibility, the potential glycosylation sites predicted for proteins in the Kabsch-Sander (Kabsch and Sander, 1983) database is used since no secondary structural information is available at the present time for any O-glycosylated proteins. For this analysis, the 50 potential sites with the highest h values are selected. As shown in Table 6, these potential glycosylation sites are very strongly selected against α-helical conformation. The preferred conformations appear to be a random coil, a sharp bend, or β-strand from P4 to P0 followed by a turn. Thus, there seems to be no unique secondary structure recognized by the enzyme but, rather, extended conformations seem to be preferred. Stated in other terms, the enzyme does not require a preformed secondary structure but imposes one upon binding of the substrate. The hydration index of the amino acids in the potential glycosylation sites, also shown in Table 6, indicates that most peptides are reasonably exposed to the aqueous environment.

EXAMPLE 11

Transfer of N-acetylgalactosamine to Native Protein Acceptors by GalNAc-Transferase The above conclusions and the predictions of the specificity algorithm are validated experimentally by studying the ability of bovine colostrum GalNAc-transferase to transfer N-acetylgalactosamine to a variety of acceptors, both native proteins and synthetic acceptor peptides. The transfer of N-acetylgalactosamine to protein acceptors is assayed as described by Elhammer and Kornfeld, 1986, with minor modifications. The concentration of UDP-GalNAc is saturating in all assays; a $K_m$ of 8 μM is reported for bovine colostrum GalNAc-transferase (Elhammer and Kornfeld, 1986).

The reaction products are characterized using alkaline sodium borohydride treatment essentially as described by Carlson (1968). Digestion with Patella vulgata α-N-acetylgalactosaminidase (approximately 1 unit/ml) is done in 25 mM citrate buffer pH 4.0 in a final volume of 30 μl for 24 hours. Released radioactive sugars are separated on descending paper chromatography in pyridine-ethyl acetate-glacial acetic acid-water (5:5:1:3; v:v:v:v).

Table 7 shows that, as predicted, both bovine rhodanese and, to a lesser extent, the bacterial protein subtilisin do indeed function as acceptors for the enzyme, although neither of them reacts unless reduced and carboxymethylated prior to exposure to the enzyme. Conversely, bovine cytochrome C which contains one Ser and eight Thr residues but no predicted potential sites, is not an acceptor for the enzyme, whether in the native, or in the reduced and carboxymethylated state. Myelin basic protein, a molecule which previously has been shown to be an efficient acceptor for GalNAc-transferase (Hagopian et al., 1971) is included as a positive control in this experiment.

The experiments with native protein acceptors demonstrate that proteins which do not contain O-linked oligosaccharides in situ but do contain exposed sequences with the predicted features of an acceptor, can function as acceptors for GalNAc-transferase in vitro. It should be noted, nevertheless, that neither subtilisin nor rhodanese showed any acceptor activity without prior reduction and carboxymethylation. Although the most probable of the predicted sites in rhodanese, $Thr_{141}$, is located in an exposed segment on the molecule, inspection of the three-dimensional structure of rhodanese revealed that the hydroxyl group of this amino acid is oriented not toward the surrounding solvent but toward the hydrophobic core. This then probably accounts for the need for mild denaturation for acceptor activity. Rhodanese contains two additional predicted acceptor sites, $Ser_{142}$ and $Ser_{145}$, (FIG. 8). However, due to the low rates of transfer to serine residues under our standard assay conditions, transfer to these sites should not contribute significantly to the total transfer in the assay. The lower rate of transfer to reduced and carboxymethylated rhodanese, compared to that of myelin basic protein, may be related to incomplete exposure of the acceptor sites even by the reduction and carboxymethylation procedure, and/or differences in rate constants between the acceptor sequences on the two molecules. Myelin basic protein contains one site predicted with high probability and three additional low probability sites. The molecule can reportedly be glycosylated with 1.2 to 1.5 N-acetylgalactosamines per molecule (Cruz and Moscarello, 1983).

The bacterial protein subtilisin contains four predicted serine sites with probabilities higher than 0.6 (FIG. 8). Three of the serines have a high exposure index in the native protein (Kabsch and Sander, 1983), but the three-dimensional structure of the protein indicates that the hydroxyls are located in a restrained environment. Again, this could account for the need for reduction and carboxymethylation for acceptor activity. The 35 times slower transfer rate to denatured subtilisin, as compared to myelin basic protein, indicates again a slower transfer to serines than to threonines, under the conditions used. Factors such as those discussed for rhodanese may also contribute to the low levels of transfer. Finally, cytochrome C, which does not contain any predicted acceptor site, is completely inactive as an acceptor, whether in the native or in the reduced and carboxymethylated form.

EXAMPLE 12

Figure 9B:
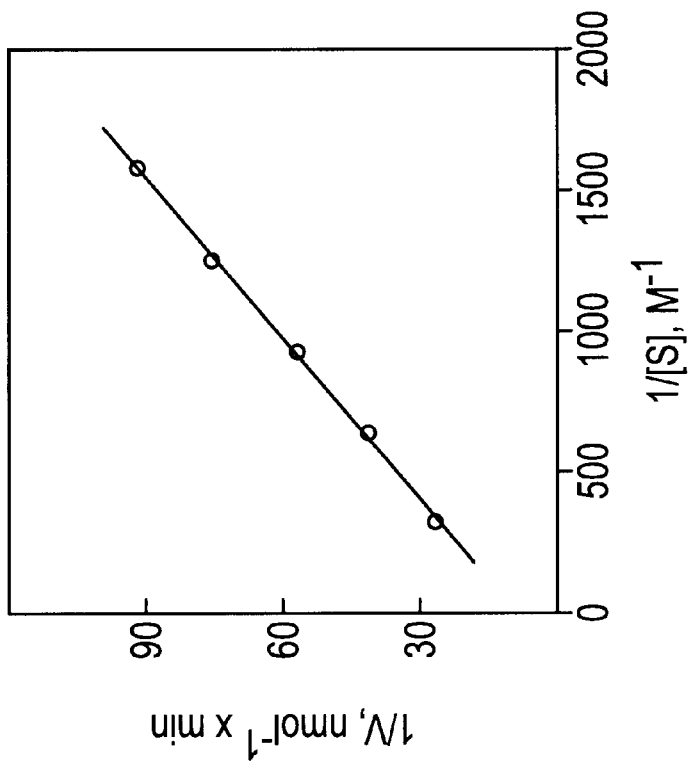
FIGS. 9A and 9B. Lineweaver-Burk plots of GalNAc-transferase reaction velocities. The transfer of $^3$H-acetylgalactosamine to the acceptor peptides by bovine colostrum GalNAc-transferase was assayed as outlined in Materials and Methods. A representative experiment for each peptide is shown. The substrates were (A): RTPPP [SEQ ID NO:12]; and (B): PPASTSAPG [SEQ ID NO:14].
Figure 9A:
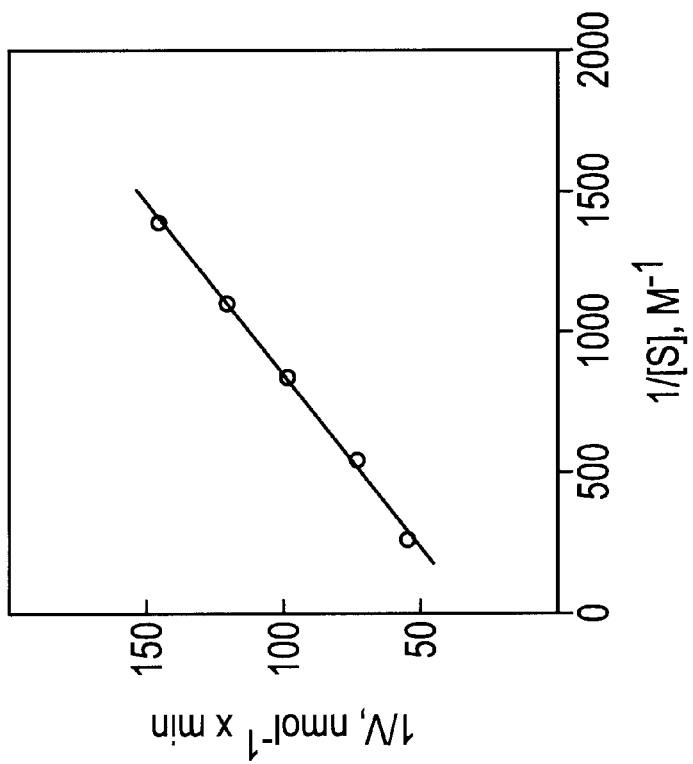
Figure 10A:
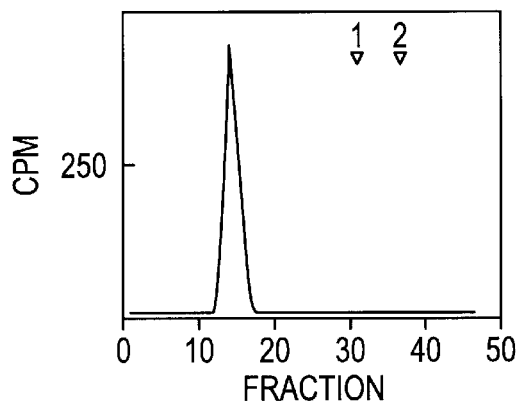
FIGS. 10A–10F. Characterization of the reaction products from in vitro glycosylation of PPASTSAPG [SEQ ID NO:14] and PPASSSAPG [SEQ ID NO:15]. Products from glycosylation of the acceptor peptides PPASTSAPG [SEQ ID NO:14] (Panels A,B and C) and PPASSSAPG [SEQ ID NO:15] (Panels D, E and F) were isolated by BioGel P-2 chromatography and separated on descending paper chromatography in pyridine-ethyl acetate-glacial acetic acid-water (5:5:1:3, v:v:v:v). Panels A and D: the untreated glycosylated peptides; Panels B and E: products from digestion with *Patella vulgata* α-N-acetylgalactosaminidase; Panels C and F: products from mild alkaline sodium borohydride treatment. The migration distances of standards are indicated by arrows. 1: Galβ1–3GalNAc-ol; 2: GalNAc-ol.
Figure 10D:
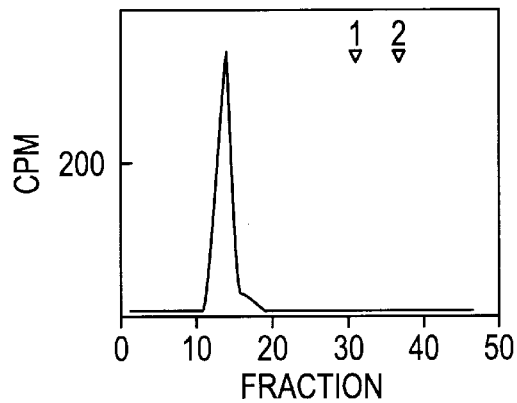
Figure 10B:
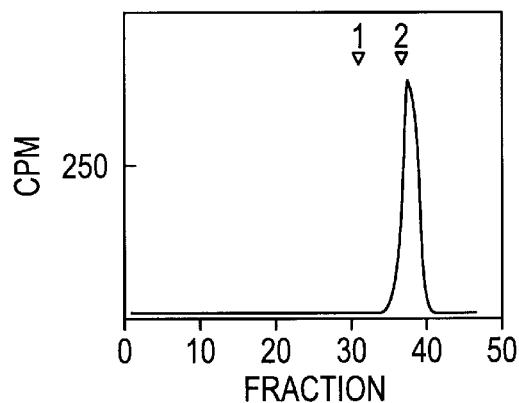
Figure 10E:
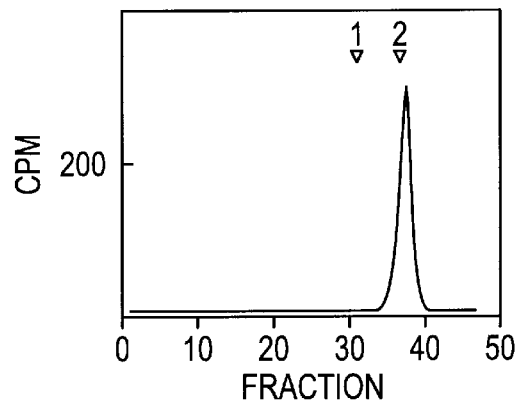
Figure 10C:
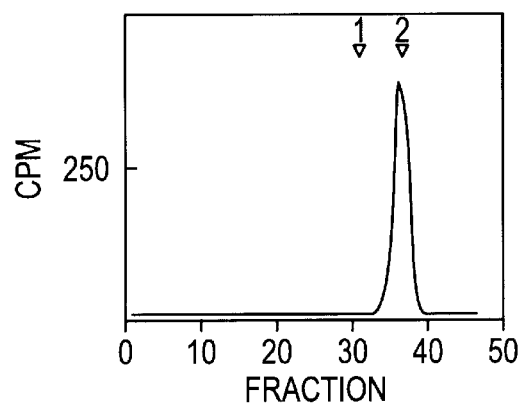
Figure 10F:
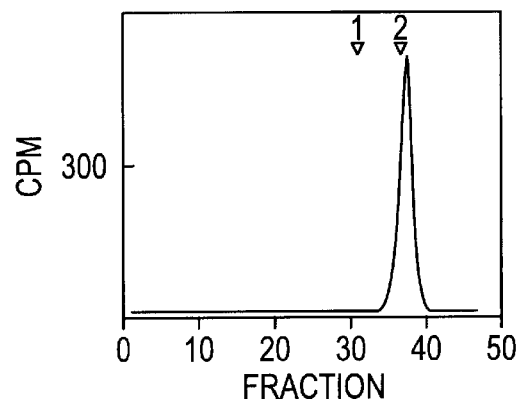

Transfer of N-acetylgalactosamine to Synthetic Acceptor Peptides by GalNAc-Transferase The ability of GalNAc-transferase to glycosylate a series of synthetic acceptor peptides is shown in FIG. 9 and Table 8. The synthetic acceptor peptides Arg-Thr-Pro-Pro-Pro (RTPPP) [SEQ ID NO:12], Arg-Ser-Pro-Pro-Pro (RSPPP) [SEQ ID NO:13], Pro-Pro-Ala-Ser-Thr-Ser-Ala-Pro-Gly (PPASTSAPG) [SEQ ID NO:14], Pro-Pro-Ala-Ser-Ser-Ser-Ala-Pro-Gly (PPASSSAPG) [SEQ ID NO:15] and Pro-Pro-Ala-D-Ser-Thr-D-Ser-Ala-Pro-Gly (PPAdSTdSAPG) are synthesized by solid phase methodology on an Applied Biosystems Inc 430A peptide synthesizer (ABI, Foster City, Calif.) using double couple cycles with standard t-Boc chemistry on a 0.5 mmol scale. The t-Boc-amino acids and the PAM resin solid supports are supplied by ABI. The completed peptides are removed from the supporting resin, concurrently with the side chain-protecting groups, by a standard HF cleavage procedure using anisole as a cation scavenger (10% v/v). The crude peptides are purified by preparative reverse phase chromatography on a C18 Vydac column (2.5×30 cm) using a water/acetonitrile gradient, each phase containing 0.1% TFA. Each purified peptide is characterized by FAB/MS and shows a single symmetrical peak on analytical HPLC.

Sequence analysis for the identification of the glycosylated amino acid(s) in the acceptor peptides PPASTSAPG [SEQ ID NO:14] and PPASSSAPG [SEQ ID NO:15] is performed using an Applied Biosystems (ABI) 470A sequencer equipped with an on-line ABI 120A PTH analyzer. PTH derivatives are dissolved in 120 µl 20% acetonitrile in water; 50 µl of this solution is injected onto the HPLC and the remainder diverted to a fraction collector. Cartridge filters are prepared with 1.5 mg polybrene using the ABI program 03RPRE. Samples are sequenced using the ABI program 03RPTH. Peptides are dissolved in 60 µl of 50% acetic acid and loaded onto the filter in two 30 µl aliquots.

The experiments shown in FIG. 10 demonstrate that the incorporated radioactivity in the acceptor peptides PPASTSAPG [SEQ ID NO:14] and PPASSSAPG [SEQ ID NO:15] is in the form of N-acetylgalactosamine. Digestion of the two glycosylated peptides with Patella vulgata α-N-acetylgalactosaminidase releases only GalNAc and alkaline sodium borohydride treatment results in the release GalNAc-ol both from PPASTSAPG [SEQ ID NO:14] and PPASSSAPG [SEQ ID NO:15].

Figure 11A:
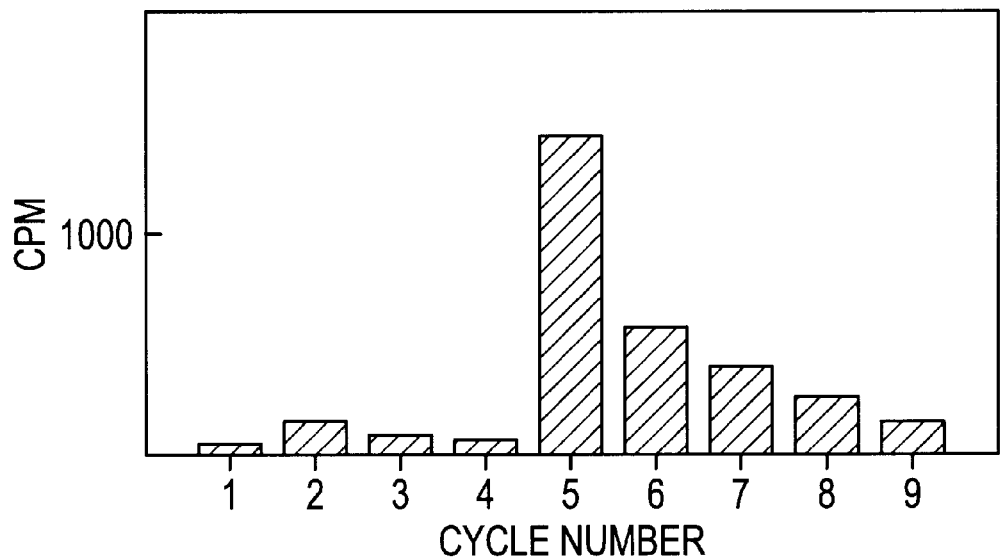
FIGS. 11A and 11B. Determination of acceptor peptide amino acids conjugated with radioactive N-acetylgalactosamine after glycosylation with bovine colostrum GalNAc-transferase. Glycosylated acceptor peptides were isolated from assay mixtures by BioGelP-2 chromatography and subjected to automated Edman degradation as described in Materials and Methods. The radioactivity eluted in each sequencing cycle was determined by scintillation counting. A and B show fractions collected from sequencing of glycosylated PPASTSAPG [SEQ ID NO:14] and PPASSSAPG [SEQ ID NO:15], respectively.
Figure 11B:
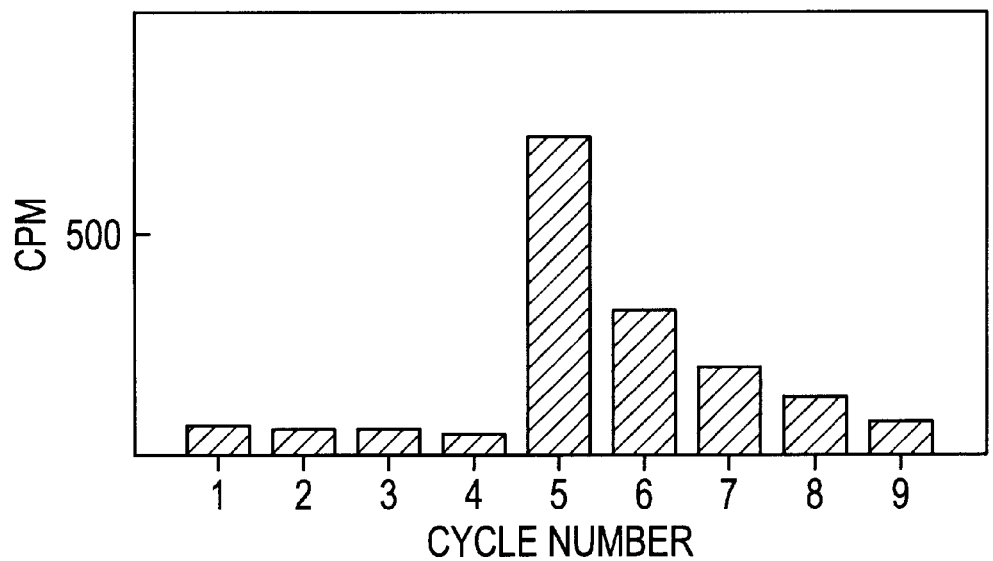

The glycosylated amino acids in the peptides PPASTSAPG [SEQ ID NO:14] and PPASSSAPG [SEQ ID NO:15] are identified by sequencing of the reaction products from the corresponding assay. FIG. 11 shows that for both glycosylated peptides the majority of the sugar-linked radioactivity is associated with residue #5, the central amino acid, be it threonine, as in PPASTSAPG [SEQ ID NO:14], or serine, as in PPASSSAPG [SEQ ID NO:15]. The measurable amounts of radioactivity associated with the residues following residue 5 are presumably due to the large load of peptide in the sequencer necessitated by the low specific radioactivity of the sample. Nevertheless, since the radioactivities associated with residues 7 and 8 extrapolate smoothly to that of residue 6, it is most likely that, within our experimental error, residue 6 is not labelled.

The transfer of N-acetylgalactosamine to peptide acceptors is assayed by two different assays. The concentration of UDP-GalNAc is saturating in all assays; a Km of 8 µM is reported for bovine colostrum GalNAc-transferase (Elhammer and Kornfeld, 1986). For the determination of kinetic parameters the reaction mixture contains 50 mM Imidazole, pH 7.2, 10 mM $MnCl_2$, 0.5% Triton X-100, 150 µM UDP-GalNAc, approximately 120,000 cpm of UDP-[1-$^3$H]-GalNAc, varying concentrations of acceptor (see individual experiments) and approximately 5 mU of enzyme in a final volume of 40 µl; standard incubation time is 20 minutes. The reaction is terminated by placing the samples in a boiling water bath for 1.5 minutes. The reaction product (glycosylated peptide) is separated from unreacted UDP-GalNAc by chromatography on Dowex-2 columns (0.5 ml bed volume) equilibrated in water; the run-through fraction (2.5 ml) containing the glycosylated peptide is collected, supplemented with scintillation fluid and counted for radioactivity. For the determination of the low levels of transfer to serine, the assay conditions are as follows: 50 mM Imidazole, pH 7.2, 10 mM MnCl$_2$, 0.5% Triton X-100, 150 μM UDP-GalNAc, approximately 260,000 cpm UDP-[$^3$H]-GalNAc and 3.2 mM acceptor peptide (the concentration of RSPPP is 3.7 mM). The assays are incubated for 20 minutes (PPASTSAPG) [SEQ ID NO:14] or 8 hours (PPASSSAPG [SEQ ID NO:15], PPAdSSdSAPG and RSPPP [SEQ ID NO:13]). Following incubation, the enzyme is inactivated by placing the samples on a boiling water bath for 1.5 minutes. The samples are then allowed to cool and the reaction products are separated from unreacted UDP-GalNAc and free GalNAc by chromatography on a Biogel P-2 column (1×50 cm) equilibrated in 7% isopropanol; thirty 1.3 ml fractions are collected.

The peptide PPASTSAPG [SEQ ID NO:14] is designed to contain a single Thr, at P0. The proline residues at P4, P3 and P3' provide maximum probabilities at those positions; serine residues at P1 and P1' result in good probabilities without much steric constraint. Finally, the alanine residues at P2 and P2' and the glycine at P4 are indifferent as to the probability of glycosylation but allow for flexibility of the peptide backbone. The aggregate probability of the peptide is still optimal: h=0.985 and the peptide is predicted by the algorithm to be an ideal acceptor. Tables 8 and 9 show that this peptide is the most efficient of the acceptors tested and comparative assays show that its reactivity is very close to that of bovine apomucin (data not shown). Furthermore, the kinetic parameters for the two peptides, determined under our conditions, are quite comparable to those of the purified porcine submaxillary GalNAc-transferase-catalyzed glycosylation of peptides whose structure is derived from sites identified in porcine submaxillary mucin (Wang et al., 1992).

The peptide RTPPP [SEQ ID NO:12], derived from the major acceptor sequence in myelin basic protein (Hagopian et al.,1971), has a $K_m$ lower than that of PPASTSAPG [SEQ ID NO:14] but also a much lower $V_{max}$ and, hence, its catalytic efficiency is only half of that of PPASTSAPG [SEQ ID NO:14]. The activities of the two corresponding peptides containing serine instead of threonines are measurable but too low for determining the kinetic parameters under the conditions used. Clearly, however, bovine colostrum GalNAc-transferase is capable of transferring GalNAc to the serine of these peptides, albeit—under our in vitro conditions—approximately 35 times slower than to threonine (Table 9).

Substitution of the two amino acids flanking the acceptor threonine in PPASTSAPG [SEQ ID NO:14] with D-amino acids results in a 250-fold drop in the rate of transfer, clearly demonstrating that the active site of the enzyme recognizes a peptide segment which extends beyond the acceptor amino acid itself. Indeed, the finite residual activity of the D-Ser peptide indicates that none of the recognition subsites is essential and that the P3, P4, and P3' residues are able to compensate partly for the loss of the specific P1 and P1' residues. Interestingly, the peptide Arg-Ser-Pro-Pro-Pro (RSPPP) [SEQ ID NO:13], the myelin basic protein acceptor sequence where the acceptor Thr is replaced by Ser, is also glycosylated, albeit three times slower than PPAdSSd-SAPG. Again, at least in vitro, the enzyme seems to prefer threonine-containing acceptors.

In contrast to the enzyme recently purified from porcine submaxillary gland (Wang et al., 1992), however, the bovine colostrum GalNAc-transferase is definitely capable of glycosylating both threonine and serine residues. In this context it should be noted that in experiments reported by O'Connel et al. (1992), bovine colostrum GalNAc-transferase failed to glycosylate serine in a peptide derived from human erythropoietin. This phenomenon may be related to the specific acceptor peptide used, even though a serine in this position is glycosylated in vivo. Alternatively, given the considerably slower rate of transfer to serine residues by bovine colostrum GalNAc-transferase in vitro, the short incubation times used may have been insufficient to produce measurable amounts of product. Under our in vitro conditions, the transfer to the serine of PPASSSAPG [SEQ ID NO:15] is approximately 35-fold slower than to the threonine of PPASTSAPG [SEQ ID NO:14]. This observation immediately raises the question whether serine is an acceptor at all for in situ glycosylations.

It is likely that Ser is indeed an in vivo acceptor, for the following reasons: 1) numerous reports identify unambiguously O-glycosylated serine residues in glycoproteins; 2) preliminary experiments indicate that the Ser- and Thr-glycosylating activities have similar pH optima and that both are independent of calcium concentrations in the assays; 3) the affinity matrix for isolation of the enzyme is bovine apomucin immobilized on Sepharose. This ligand contains comparable numbers of serine and threonine residues and should consequently not distinguish between the two activities (compare below); 4) a mere 35-fold difference in rate is quite usual and is, in fact, rather small as a range of specificity for multisubstrate enzymes. Slight changes in experimental conditions may well obviate, or even reverse the reactivities observed under our conditions. It is unlikely that the serine transferase activity of the enzyme preparation would be caused by a contaminating serine transferase since: a) the enzyme is pure as judged by SDS-PAGE/silver staining as well as by N-terminal sequencing; b) an antibody raised against the purified transferase precipitates both Ser- and Thr-glycosylating activities; c) assay of samples of crude, partially purified, and pure enzyme yielded the same ratio of Ser- and Thr-transferase activities.

The specificity of GalNAc-transferase is adequately described by a cumulative specificity model, where the independent contribution of several subsites can produce a range of reactivities toward peptide segments. Additional important features of the acceptor peptide segments are exposure on the surface of the protein substrate and an extended conformation. The acceptor amino acid is surrounded preferentially by Ser, Thr, Pro, Ala and Gly residues, but in no specific order. Both serine and threonine are acceptor amino acids, at least for the bovine colostrum enzyme.

EXAMPLE 13

Transfer of N-acetylgalactosamine to Synthetic Acceptor Peptides by Soluble GalNAc-Transferase The ability of GalNAcTs to glycosylate a series of synthetic acceptor peptides was also studied. Assays for the determination of kinetic parameters for peptide acceptors were carried out as described by Elhammer et al. (1993) but using a modification of the method described by O'Connel and Tabak (1993) for isolation of the acceptor peptides: One ml Bond Elut columns containing 100 mg packing material were used. Before loading the assay samples, the columns were washed with 2 ml methanol followed by 2 ml 0.1% TFA (in water). The assay samples (40 μl) were diluted to 1 ml with 0.1% TFA and loaded on the columns. Unbound radioactivity was than washed out with 4 ml 0.1% TFA, after which the glycosylated acceptor peptides were eluted with 1.5 ml 35% acetonitrile, 0.1% TFA (in water), directly into scintillation vials. Calculation of kinetic parameters was done from double reciprocal plots (1/v versus 1/S) using standard procedures. Determination of kinetic parameters for the cloned soluble GalNAc-transferase resulted in the following numbers: The Km for UDP-GalNAc is approximately 1.7 ,M and the Km:s for the threonine containing acceptor peptide PPASTSAPG [SEQ ID NO:14] and the serine containing acceptor peptide PPDAASAAPLR [SEQ ID NO:17] are approximately 6.5 and 3.6 mM, respectively. Transfer by GalNAcTs to another serine containing acceptor peptide PPASSSAPG [SEQ ID NO:15] is approximately 70 times slower than to PPASTSAPG [SEQ ID NO:14] (Data not shown). The specific activity of the purified enzyme preparation, using bovine apomucin as acceptor, is approximately 2,160 U/mg protein (Table 4).

The enzymatic properties of the purified GalNacTs appear to be similar to the those determined for the enzymes purified from bovine colostrum and porcine submaxillary gland (Elhammer and Kornfeld, 1986; Elhammer et al., 1993; Wang et al., 1992; Wang et al., 1993). The Km for the acceptor peptide PPASTSAPG [SEQ ID NO:14] is almost identical for the colostrum enzyme and the baculo expressed molecule, 6.0 vs. 6.5 mM. The serine containing acceptor peptide PPDAASAAPLR [SEQ ID NO:17] (O'Connel et al. 1992; Wang et al., 1993), also has a Km in the low mM range, 3.5 mM, in assays with GalNAcTs. This is similar to the Km determined for this acceptor using the GalNac-transferase purified from porcine submaxillary glands, 4.5 mM (Wang et al., 1993). A Km for PPDAASAAPLR [SEQ ID NO:17] using the bovine colostrum enzyme, has not been determined. Instead, it has been reported that this peptide is not an acceptor for the colostrum enzyme (O'Connel et al., 1993). Both GalNAcTs and the bovine colostrum enzyme glycosylate the peptide PPASSSAGP [SEQ ID NO:15] are at least 35 times slower than PPASTSAPG [SEQ ID NO:14] (Elhammer et al., 1993). The Km for UDP-GalNAc in assays using GalNAcTs is lower than those determined for the bovine colostrum and the porcine submaxillary gland enzymes, 1.7 $\mu$M vs. 8 $\mu$M and 6 $\mu$M, respectively (Table V; Elhammer & Kornfeld, 1986; Wang et al., 1992). The reason for this is not clear at present. The amino acid sequence of the bovine colostrum and the cloned molecules should be identical except for five amino acids in the $NH_2$-terminal end of the molecule; the colostrum enzyme sequence also contains an additional two amino acids at the $NH_2$-terminus. A possible explanation is that differences in post-translational processing, in particular glycosylation, of the Sf9 produced vs. the bovine molecule may, to some extent, influence the kinetic characteristics of the two molecules.

As discussed above, the oligosaccharide structures on the insect produced molecule are most likely of high mannose and/or truncated high mannose type, while results from endoglycosidase digestion experiments suggest that the colostrum enzyme contains complex type oligosaccharides (Elhammer & Kornfeld, 1986). It is likely that the N-linked oligosaccharide structures on the porcine enzyme also would be of the types normally synthesized by mammalian cells; peptide: N-glycosidase F digestion experiments suggest that this molecule contains 9 kDa of N-linked oligosaccharides (Wang et al., 1992). Further experiments will however be needed to clarify this question. Taken together the experimental data suggest that the recombinant, soluble enzyme has in vitro enzymatic characteristics quite similar to those determined for the native (colostrum) enzyme. The availability of this molecule should facilitate further studies on the enzymatic properties of GalNAc-transferase as well as experiments on in vitro synthesis of O-linked glycoconjugates.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments illustrated herein, but is only limited by the following claims.

TABLE 1

Expression of baculovirus isolates of the GalNAc-transferase

| Construct | Specific activity, Units/mg protein | Relative rate |
|---|---|---|
| Uninfected cells | 0.16 | 1 |
| CMW Pol-1 | 0.13 | 0.8 |
| GalNAcT 2-1.A | 13.9 | 87 |
| GalNAcT 2-1.B | 11.9 | 74 |

TABLE 2

Expression of baculovirus isolates of soluble GalNAc-transferase

| | Total activity (U[a]) | |
|---|---|---|
| Construct | Cell lysate | Culture medium |
| Uninfected cells | 0.15 | 0.44 |
| α6-3 | 0.12 | 0.40 |
| GalNAcT 2-1A | 16.22 | 1.61 |
| GalNAcT-Mel | 32.15 | 57.80 |

[a]1 unit equals one mole N-acetylgalactosamine transferred to apomucin per minute, under assay conditions.

The GalNAc-transferase constructs GalNAcT 2–1A and GalNAcTs-Mel together with a construct coding for an unrelated molecule, α6–3 (a γ-aminobutyric acid receptor subunit), were expressed in Sf9 cells. Cells (1X10[6]) were infected with recombinant virus containing GalNAcTs-Mel (5 pfu/cell). The cells were harvestd 65 hours post infrction, lysed in a detergent containing buffer and the GalNac-transferase activity was determined in the cell lysates and the corresponding culture media; lysate and culture medium from uninfected cells were assayed as control. The numbers have been adjusted for differences in protein content in the cell lysates; the volume of the culture media was 5 ml.

TABLE 3

Glycosylation sites. Abundance of amino acids at subsites

| AMINO ACID | % S.D. AVERAGE | # EXPECTED IN 196 A.A. | # FOUND IN 196 RESIDUES | | | | | | | |
|---|---|---|---|---|---|---|---|---|---|---|
| | | | P4 | P3 | P2 | P1 | P0 | P1' | P2' | P3' | P4' |
| D | 5.7 +/- 2.2 | 11.17 +/- 4.31 | 6 | 2 | 3 | 2 | 0 | 2 | 6 | 3 | 6 |
| N | 4.4 +/- 2.0 | 8.62 +/- 3.92 | 5 | 4 | 6 | 3 | 0 | 4 | 7 | 3 | 4 |
| E | 6.4 +/- 2.9 | 12.54 +/- 5.68 | 10 | 10 | 8 | 5 | 0 | 15 | 13 | 7 | 11 |
| Q | 3.9 +/- 1.7 | 7.64 +/- 3.33 | 4 | 7 | 6 | 5 | 0 | 5 | 8 | 6 | 7 |
| S | 6.6 +/- 2.7 | 12.94 +/- 5.29 | 21 | 29 | 25 | 28 | 90 | 35 | 33 | 21 | 24 |

TABLE 3-continued

Glycosylation sites. Abundance of amino acids at subsites

| AMINO ACID | % S.D. AVERAGE | # EXPECTED IN 196 A.A. | # FOUND IN 196 RESIDUES | | | | | | | | |
|---|---|---|---|---|---|---|---|---|---|---|---|
| | | | P4 | P3 | P2 | P1 | P0 | P1' | P2' | P3' | P4' |
| G | 7.8 +/- 3.0 | 15.29 +/- 5.88 | 15 | 12 | 11 | 13 | 0 | 16 | 14 | 9 | 15 |
| H | 2.2 +/- 1.3 | 4.31 +/- 2.55 | 2 | 6 | 4 | 2 | 0 | 2 | 3 | 3 | 5 |
| R | 4.8 +/- 2.5 | 9.41 +/- 4.90 | 3 | 2 | 3 | 7 | 0 | 3 | 7 | 3 | 4 |
| T | 5.8 +/- 2.3 | 11.37 +/- 4.51 | 20 | 21 | 26 | 27 | 106 | 31 | 21 | 28 | 27 |
| A | 8.7 +/- 3.7 | 17.05 +/- 7.25 | 20 | 16 | 20 | 24 | 0 | 22 | 20 | 17 | 16 |
| P | 4.5 +/- 2.0 | 8.82 +/- 3.92 | 24 | 30 | 25 | 30 | 0 | 24 | 25 | 49 | 25 |
| Y | 3.3 +/- 1.9 | 6.47 +/- 3.72 | 2 | 3 | 5 | 2 | 0 | 1 | 2 | 3 | 2 |
| V | 7.0 +/- 2.5 | 13.72 +/- 4.90 | 12 | 12 | 12 | 15 | 0 | 10 | 11 | 12 | 13 |
| M | 2.1 +/- 1.3 | 4.12 +/- 2.55 | 6 | 4 | 6 | 4 | 0 | 3 | 2 | 5 | 3 |
| I | 5.2 +/- 2.3 | 10.19 +/- 4.51 | 6 | 5 | 9 | 9 | 0 | 8 | 6 | 6 | 5 |
| L | 8.2 +/- 3.2 | 16.07 +/- 6.27 | 11 | 10 | 11 | 11 | 0 | 6 | 8 | 7 | 9 |
| F | 3.9 +/- 1.9 | 7.64 +/- 3.72 | 2 | 4 | 3 | 4 | 0 | 1 | 0 | 3 | 3 |
| K | 6.8 +/- 3.3 | 13.33 +/- 6.47 | 5 | 4 | 4 | 1 | 0 | 4 | 5 | 2 | 5 |
| C | 1.6 +/- 1.5 | 3.14 +/- 2.94 | 1 | 0 | 0 | 1 | 0 | 2 | 1 | 1 | 1 |
| W | 1.2 +/- 1.0 | 2.35 +/- 1.96 | 1 | 1 | 1 | 2 | 0 | 0 | 1 | 1 | 1 |
| NUMBER OF SIGNIFICANTLY ABUNDANT RESIDUES | | | 24 | 80 | 76 | 85 | 196 | 90 | 79 | 77 | 76 |
| SELECTIVITY OF SUBSITES, $S_i$ | | | 0.4 | 1.1 | 0.9 | 1.1 | 8.1 | 1.3 | 1.0 | 1.6 | 0.9 |

TABLE 4

Glycosylation. Surabundant amino acids surrounding the reactive Ser or Thr Surabundance at a given subsite for a given amino acid is expressed as the number of that amino acid found at the site in excess to that expected from random distribution, divided by the S.D. of the expected distribution. The excess of surabundant residues is equal to or higher than twice: the S.D. of the expected residue

| AMINO ACID | P4 | P3 | P2 | P1 | P0 | P1+ | P2' | P3' | P4' |
|---|---|---|---|---|---|---|---|---|---|
| S | (1.5) | 3.0 | 2.3 | 2.8 | 14.6 | 4.2 | 3.8 | (1.5) | 2.1 |
| T | (1.9) | 2.1 | 3.2 | 3.5 | 21.0 | 4.4 | 2.1 | 3.7 | 3.5 |
| P | 3.9 | 5.4 | 4.1 | 5.4 | | 3.9 | 4.1 | 10.3 | 4.1 |

TABLE 5

Glycosylation specificity parameters, $s_{i,j}$

| AMINO ACID | P4 | P3 | P2 | P1 | P0 | P1' | P2' | P3' | P4' |
|---|---|---|---|---|---|---|---|---|---|
| D | 0.54 | 0.18 | 0.27 | 0.18 | 0.00 | 0.18 | 0.54 | 0.27 | 0.54 |
| N | 0.58 | 0.46 | 0.70 | 0.35 | 0.00 | 0.46 | 0.81 | 0.35 | 0.46 |
| E | 0.80 | 0.80 | 0.64 | 0.40 | 0.00 | 1.20 | 1.04 | 0.56 | 0.88 |
| Q | 0.52 | 0.92 | 0.78 | 0.65 | 0.00 | 1.05 | 1.05 | 0.78 | 0.92 |
| S | 1.62 | 2.24 | 1.93 | 2.16 | 6.96 | 2.71 | 2.55 | 1.62 | 1.86 |
| G | 0.98 | 0.78 | 0.72 | 0.85 | 0.00 | 1.05 | 0.92 | 0.59 | 0.98 |
| H | 0.46 | 1.39 | 0.93 | 0.46 | 0.00 | 0.46 | 0.70 | 0.70 | 1.16 |
| R | 0.32 | 0.21 | 0.32 | 0.74 | 0.00 | 0.32 | 0.74 | 0.32 | 0.43 |
| T | 1.76 | 1.85 | 2.29 | 2.38 | 9.32 | 2.73 | 1.85 | 2.46 | 2.38 |
| A | 1.17 | 0.94 | 1.17 | 1.41 | 0.00 | 1.29 | 1.17 | 1.00 | 0.94 |
| P | 2.72 | 3.40 | 2.83 | 3.40 | 0.00 | 2.72 | 2.83 | 5.56 | 2.83 |
| Y | 0.31 | 0.46 | 0.77 | 0.31 | 0.00 | 0.15 | 0.31 | 0.46 | 0.31 |
| V | 0.87 | 0.87 | 0.87 | 1.09 | 0.00 | 0.73 | 0.80 | 0.87 | 0.95 |
| M | 1.46 | 0.97 | 1.46 | 0.97 | 0.00 | 0.73 | 0.49 | 1.21 | 0.73 |
| I | 0.59 | 0.49 | 0.88 | 0.88 | 0.00 | 0.78 | 0.59 | 0.59 | 0.49 |
| L | 0.68 | 0.62 | 0.68 | 0.68 | 0.00 | 0.37 | 0.50 | 0.44 | 0.56 |
| F | 0.26 | 0.52 | 0.39 | 0.52 | 0.00 | 0.13 | 0.01 | 0.39 | 0.39 |
| K | 0.38 | 0.30 | 0.30 | 0.08 | 0.00 | 0.30 | 0.38 | 0.15 | 0.38 |
| C | 0.32 | 0.03 | 0.03 | 0.32 | 0.00 | 0.64 | 0.32 | 0.32 | 0.32 |
| W | 0.43 | 0.43 | 0.43 | 0.85 | 0.00 | 0.04 | 0.43 | 0.43 | 0.43 |

TABLE 6

Distribution of mean hydration and secondary structure index in the fifty peptides of the Kabsch-Sander database with the highest probability of O-glycosylation
NUMBER OF RESIDUES IN DATABASE = 10747
NUMBER OF ENNEAPEPTIDES IN DATABASE = 10235

| SS INDEX | | TOTAL | P4 | P3 | P2 | P1 | P0 | P1' | P2' | P3' | P4' | EXPECTED |
|---|---|---|---|---|---|---|---|---|---|---|---|---|
| B | β-bridge | 204 | 3 | 0 | 0 | 1 | 1 | 1 | 1 | 1 | 3 | 1.0 |
| E | β-strand | 2091 | 18 | 14 | 18 | 15 | 13 | 11 | 7 | 6 | 4 | 10.2 |
| G | $3_{10}$-helix | 308 | 0 | 0 | 0 | 0 | 0 | 0 | 0 | 0 | 0 | 1.5 |
| H | α-helix | 2743 | 2 | 2 | 2 | 2 | 2 | 2 | 2 | 2 | 3 | 13.4 |
| I | π-helix | 0 | 0 | 0 | 0 | 0 | 0 | 0 | 0 | 0 | 0 | 0 |
| S | bend | 1377 | 7 | 14 | 13 | 12 | 13 | 13 | 15 | 15 | 14 | 6.7 |
| T | turn | 1349 | 4 | 3 | 3 | 6 | 5 | 3 | 6 | 10 | 9 | 6.6 |
| n | none | 2675 | 16 | 17 | 14 | 14 | 16 | 20 | 19 | 16 | 17 | 13.1 |

| HYD. INDEX | TOTAL | P4 | P3 | P2 | P1 | P0 | P1' | P2' | P3' | P4' |
|---|---|---|---|---|---|---|---|---|---|---|
| 0 | 2068 | 11 | 7 | 4 | 7 | 5 | 7 | 4 | 3 | 8 |
| 1 | 1208 | 5 | 6 | 4 | 4 | 4 | 5 | 1 | 7 | 6 |
| 2 | 944 | 3 | 9 | 7 | 4 | 3 | 6 | 6 | 5 | 5 |
| 3 | 797 | 7 | 4 | 7 | 7 | 5 | 7 | 8 | 4 | 6 |
| 4 | 725 | 5 | 2 | 5 | 4 | 1 | 5 | 3 | 4 | 1 |
| 5 | 752 | 6 | 3 | 1 | 2 | 4 | 3 | 1 | 4 | 7 |
| 6 | 685 | 4 | 3 | 7 | 7 | 4 | 1 | 4 | 4 | 2 |
| 7 | 594 | 2 | 2 | 5 | 1 | 6 | 4 | 4 | 3 | 1 |
| 8 | 534 | 2 | 4 | 3 | 4 | 5 | 2 | 4 | 3 | 4 |
| 9 | 511 | 3 | 4 | 0 | 0 | s | 4 | 5 | 2 | 3 |

TABLE 6-continued

| 10 | 1929 | 2 | 6 | 7 | 10 | 8 | 6 | 10 | 11 | 7 |
|---|---|---|---|---|---|---|---|---|---|---|
| MEAN HYD. | | 4.5 | 3.7 | 4.4 | 4.7 | 4.8 | 5.6 | 4.4 | 5.7 | 5.2 | 4.4 |

TABLE 7

Transfer of N-acetylgalactosamine to protein acceptors
The transfer of N-acetylgalactosamine to protein acceptors was assayed under standard conditions (see Material and Methods). The acceptor concentration was 65 μM, the enzyme concentration approximately 65 mU/ml and assay time was 60 minutes. The transfer to both native and reduced-carboxymethylated acceptors was assayed.

| | Product formed nmol/min/mg | |
|---|---|---|
| Acceptor | Native | Reduced and carboxymethylated |
| Myelin basic protein | 22.2 | 21.3[a] |
| Bovine rhodanese | <0.1 | 3.3 |
| Subtilisin | <0.1 | 0.6 |
| Bovine cytochrome C | <0.1 | <0.1 |

[a]Myelin basic protein was not reduced and carboxymethylated in this experiment.

TABLE 8

Determination of kinetic parameters for acceptor peptides
Assays were carried out as described in Materials and Methods. Assay time was 20 minutes. The values are given as means ± S.E. (n = 3)

| Acceptor | $K_m$ mM | $10^3 \times V_{max}^a$ $s^{-1}$ | $V_{max}/K_m$ $M^{-1}$ $s^{-1}$ |
|---|---|---|---|
| RTPPP [SEQ ID NO:12] | 3.3 ± 0.6 | 604 ± 83 | 183 |
| PPASTSAPG [SEQ ID NO:14] | 6.0 ± 0.3 | 1,808 ± 357 | 301 |
| PPASSSAPG [SEQ ID NO:15] | n.a. | n.a. | ≈8.5[b] |
| RSPPP [SEQ ID NO:13] | n.a. | n.a. | ≈0.4[b] |
| PPAdSTdSAPG | n.a. | n.a. | ≈1.2[b] | n.a., Not applicable
[a]Calculations based on a 70 kDa molecular mass of the enzyme.
[b]Calculated assuming that $S_0 \ll K_m$

TABLE 9

Comparison of different synthetic peptides as acceptors for bovine colostrum GalNAc-transferase
Assays were done as described in Materials and Methods. The products were separated by Biogel P-2 chromatography. Assay times were 20 minutes for PPASTSAPG [SEQ ID NO:14] and 8 hours for PPASSSAPG [SEQ ID NO:15], PPAdSTdSAPG and RSPPP [SEQ ID NO:13].

| Acceptor | Product formed, nmol/min/mg | Relative rate |
|---|---|---|
| PPASTSAPG | 503.3 | 1 |
| PPASSSAPG | 14.3 | 1/35 |
| PPAdSTdSAPG | 2.0 | 1/252 |
| RSPPP | 0.67 | 1/751 |

We claim:

1. A process for altering the glycosylation of a protein produced by a eukaryotic cell, said process comprising the steps of:
   introducing into said cell at least one gene, wherein said gene is introduced into said cell by transfection with a vector comprising cDNA which codes for the enzyme N-acetylgalactosaminyltransferase; wherein said cDNA has the nucleotide sequence in SEQ ID NO. 11 and
   expressing a sufficient amount of said enzyme in said cell to thereby alter the glycosylation of said protein in said cell.

2. A process according to claim 1 wherein said cell is selected from the group consisting of Chinese hamster ovary cells, mouse L cells, mouse A9 cells, baby hamster kidney cells, C127 cells, PC8 cells, Sf9 cells, Drosophila cells and other insect and mammalian cells.

3. A process according to claim 2 wherein said vector is selected from the group consisting of pAC373, pECE, pMSG, pAV009/A+, and pMT 101/A−.

4. A process according to claim 3 wherein said vector is pAC373.

5. A process according to claim 1 including the further step of recovering the protein for which glycosylation was altered.

6. A cDNA sequence encoding the enzyme N-acetylgalactosaminyltransferase comprising the nucleotide sequence in SEQ ID NO. 11.

7. A recombinant DNA molecule comprising a DNA sequence encoding the enzyme N-acetylgalactosaminyltransferase wherein said enzyme is comprised of the amino acid sequence in SEQ ID NO. 9.

8. The recombinant DNA molecule of claim 7 comprising the nucleotide sequence as set forth in FIG. 15 of this specification.

9. A recombinant DNA molecule comprising the recombinant DNA molecule of claim 7 wherein the sequences coding for the cytoplasmic and membrane spanning domains of the full-length cDNA have been deleted.

10. A recombinant DNA molecule comprising a DNA sequence encoding the enzyme N-acetylgalactosaminyltransferase wherein said enzyme is comprised of the amino acid sequence as set forth in SEQ ID NO. 19.

11. The recombinant DNA molecule of claim 10 wherein the sequences coding for the cytoplasmic and membrane spanning domains of the full-length cDNA have been substantially deleted.

* * * * *

UNITED STATES PATENT AND TRADEMARK OFFICE
CERTIFICATE OF CORRECTION

PATENT NO.: 6,096,512
DATED: August 1, 2000
INVENTOR(S): Elhammer et al.

It is certified that error appears in the above-identified patent and that said Letters Patent is hereby corrected as shown below:

Column 14, line 36, please delete "125I" and insert --$^{125}$I--;

Column 15, line 4, please delete "11$\mu$M" and insert --1$\mu$M--;

Column 15, line 5, please delete "10$\mu$g" and insert --10ng--;

Column 16, line 3, please delete "l" and insert --$\lambda$--;

Column 31, line 2, please delete ",M" and insert --$\mu$M--;

Column 32, line 48, please delete "infrction" and insert --infection--;

Column 33, line 38, please delete "P1+" and insert --P1'--;

Column 34, line 66, please delete "s" and insert --5--;

Column 36, line 5, please delete "=" after "means" and insert --±--.

Signed and Sealed this

Twenty-second Day of May, 2001

*Attest:*

NICHOLAS P. GODICI

*Attesting Officer*     *Acting Director of the United States Patent and Trademark Office*